US012760377B2

(12) United States Patent
Cohen et al.

(10) Patent No.: US 12,760,377 B2
(45) Date of Patent: Oct. 13, 2026

(54) USE OF PROTEIN ASSEMBLIES TO RECORD CELLULAR EVENTS

(71) Applicant: President and Fellows of Harvard College, Cambridge, MA (US)

(72) Inventors: Adam Ezra Cohen, Cambridge, MA (US); Dingchang Lin, Cambridge, MA (US); Xiuyuan E. Li, Cambridge, MA (US); Doyeon Kim, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 887 days.

(21) Appl. No.: 18/046,076

(22) Filed: Oct. 12, 2022

(65) Prior Publication Data

US 2023/0151437 A1 May 18, 2023

Related U.S. Application Data

(60) Provisional application No. 63/254,820, filed on Oct. 12, 2021.

(51) Int. Cl.
*C12Q 1/6897* (2018.01)
*C12N 9/12* (2006.01)

(52) U.S. Cl.
CPC ......... *C12Q 1/6897* (2013.01); *C12N 9/1205* (2013.01)

(58) Field of Classification Search
None
See application file for complete search history.

(56) References Cited

PUBLICATIONS

Gene ID: 7846, TUBA1A tubulin alpha 1a [*Homo sapiens* (human)], https://www.ncbi.nlm.nih.gov/gene/7846, [retrieved Dec. 1, 2025] (Year: 2025).*
Gene ID: 203068, TUBA1A tubulin beta class I [*Homo sapiens* (human)], https://www.ncbi.nlm.nih.gov/gene/203068 [retrieved Dec. 1, 2025] (Year: 2025).*
Linghu et al., Spatial multiplexing of fluorescent reporters for imaging signaling network dynamics. Cell (2020), 183: 1682-1698 (Year: 2020).*
Barnett et al., Deciphering the molecular mechanism responsible for GCaMP6m's Ca2+-dependent change in fluorescence. PLoS One (2017), 12(2): e0170934 (Year: 2017).*
Li et al., Engineering a genetically encoded magnetic protein crystal. Nano Letters (2019), 19: 6955-6963 (Year: 2019).*
Kahn et al., APC2 controls dendrite development by promoting microtubule dynamics. Nature Communications (2018), 9:2773, pp. 1-17 (Year: 2018).*
Hoogenraad et al., GRIP1 controls dendrite morphogenesis by regulating EphB receptor trafficking. Nat. Neurosci. (2005): 8, 906-915 (Year: 2005).*
Henderson et al, Structure and mechanism of the photoactivatable green fluorescent protein. JACS (2009), 131: 4176-4177 (Year: 2009).*
Singh et al., Genetically encoded multispectral labeling of proteins with polyfluorophores on a DNA backbone. JACS (2013), 135: 6184-6191 (Year: 2013).*
Goodson et al., Methods for expressing and analyzing GFP-tubulin and GFP-microtubule-associated proteins. Cold Spring Harb Protoc (2010); doi:10.1101/pdb.top85 (Year: 2010).*
Askary et al., The lives of cells, recorded. Nature Reviews Genetics (2025), 26: 203-222 (Year: 2025).*
Condello et al., Multicolor time-stamp reveals the dynamics and toxicity of amyloid deposition. Scientific Reports (2011), 1:19, pp. 1012 (Year: 2011).*
Desai and Mitchison, Microtubule polymerization dynamics. Annu Rev. Cell Dev. Biol. (1997), 13: 83-117 (Year: 1997).*
Abdelfattah et al., Bright and photostable chemigenetic indicators for extended in vivo voltage imaging. Science. Aug. 16, 2019;365(6454):699-704. doi: 10.1126/science.aav6416. Epub Aug. 1, 2019.
Amemiya et al., Role of protein kinase Cβ in phorbol ester-induced c-fos gene expression in neurons of normotensive and spontaneously hypertensive rat brains. Brain Res. Apr. 8, 2005;1040(1-2):129-36. doi: 10.1016/j.brainres.2005.01.073.
Barmada et al., Visualization of Prion Infection in Transgenic Mice Expressing Green Fluorescent Protein-Tagged Prion Protein. J Neurosci. Jun. 15, 2005;25(24):5824-32. doi: 10.1523/JNEUROSCI.1192-05.2005.
Baskaran et al., An in cellulo-derived structure of PAK4 in complex with its inhibitor Inka1. Nat Commun. Nov. 26, 2015;6:8681. doi: 10.1038/ncomms9681.
Das et al., Tet-On Systems For Doxycycline-inducible Gene Expression. Curr Gene Ther. 2016;16(3):156-67. doi: 10.2174/1566523216666160524144041.
Denardo et al., Genetic strategies to access activated neurons. Curr Opin Neurobiol. Aug. 2017;45:121-129. doi: 10.1016/j.conb.2017.05.014. Epub May 31, 2017.
Denardo et al., Temporal evolution of cortical ensembles promoting remote memory retrieval. Nat Neurosci. Mar. 2019;22(3):460-469. doi: 10.1038/s41593-018-0318-7. Epub Jan. 28, 2019.
Deo et al., The HaloTag as a general scaffold for far-red tunable chemigenetic indicators. Nat Chem Biol. Jun. 2021;17(6):718-723. and supplemental information. doi: 10.1038/s41589-021-00775-w. Epub Apr. 1, 2021.
Gammie et al., cFOS and pCREB activation and maternal aggression in mice. Brain Res. Apr. 20, 2001;898(2):232-41. doi: 10.1016/s0006-8993(01)02189-8.

(Continued)

*Primary Examiner* — Catherine Konopka
(74) *Attorney, Agent, or Firm* — Wolf, Greenfield & Sacks, P.C.

(57) ABSTRACT

The present disclosure provides methods for profiling cellular events in a cell over time using protein assemblies. Methods for profiling the effect of a stimulus, such as a candidate therapeutic agent, are also provided by the present disclosure. Proteins, polynucleotides (e.g., vectors), and pairs of polynucleotides for use in the methods described herein, as well as systems and kits comprising such proteins, polynucleotides, and pairs of polynucleotides, are also provided herein.

27 Claims, 49 Drawing Sheets
(27 of 49 Drawing Sheet(s) Filed in Color)

Specification includes a Sequence Listing.

(56) References Cited

PUBLICATIONS

Gil et al., Optogenetic control of protein binding using light-switchable nanobodies. Nat Commun. Aug. 13, 2020;11(1):4044. doi: 10.1038/s41467-020-17836-8.

Glaser et al., Statistical Analysis of Molecular Signal Recording. PLOS Comput Biol. 2013;9(7):e1003145. doi: 10.1371/journal.pcbi.1003145. Epub Jul. 18, 2013.

Grimm et al., A general method to fine-tune fluorophores for live-cell and in vivo imaging. Nat Methods. Oct. 2017;14(10):987-994. doi: 10.1038/nmeth.4403. Epub Sep. 4, 2017.

Grimm et al., A general method to improve fluorophores for live-cell and single-molecule microscopy. Nat Methods. Mar. 2015;12(3):244-50, 3 p following 250. doi: 10.1038/nmeth.3256. Epub Jan. 19, 2015.

Grimm et al., A general method to optimize and functionalize red-shifted rhodamine dyes. Nat Methods. Aug. 2020;17(8):815-821. doi: 10.1038/s41592-020-0909-6. Epub Jul. 27, 2020.

Guglielmi et al., Optogenetic Control of Protein Function: From Intracellular Processes to Tissue Morphogenesis. Trends Cell Biol. Nov. 2016;26(11):864-874. doi: 10.1016/j.tcb.2016.09.006. Epub Oct. 7, 2016.

Haller et al., Patterns of violent aggression-induced brain c-fos expression in male mice selected for aggressiveness. Physiol Behav. Jun. 15, 2006;88(1-2):173-82. doi: 10.1016/j.physbeh.2006.03.030. Epub May 9, 2006.

Hertel et al., Monitoring of post-translational modification dynamics with genetically encoded fluorescent reporters. Biopolymers. Feb. 2014;101(2):180-7. doi: 10.1002/bip.22254.

Iwamoto et al., A general chemical method to regulate protein stability in the mammalian central nervous system. Chem Biol. Sep. 24, 2010;17(9):981-8. doi: 10.1016/j.chembiol.2010.07.009.

Josselyn et al., Memory engrams: Recalling the past and imagining the future. Science. Jan. 3, 2020;367(6473):eaaw4325. doi: 10.1126/science.aaw4325.

Kennedy et al., Rapid blue-light-mediated induction of protein interactions in living cells. Nat Methods. Dec. 2010;7(12):973-5. doi: 10.1038/nmeth.1524. Epub Oct. 31, 2010.

Levine III, Quantification of beta-sheet amyloid fibril structures with thioflavin T. Methods Enzymol. 1999;309:274-84. doi: 10.1016/s0076-6879(99)09020-5.

Li et al., Spatiotemporal constraints on optogenetic inactivation in cortical circuits. eLife. Nov. 18, 2019;8:e48622. doi: 10.7554/eLife.48622.

Linghu et al., Recording of cellular physiological histories along optically readable self-assembling protein chains. bioRxiv. 2021. 42 pages. doi: 10.1101/2021.10.13.464006.

Liu et al., Engineering genetically-encoded tools for optogenetic control of protein activity. Curr Opin Chem Biol. Oct. 2017;40:17-23. doi: 10.1016/j.cbpa.2017.05.001. Epub May 17, 2017.

Mahringer et al., Expression of c-Fos and Arc in hippocampal region CA1 marks neurons that exhibit learning-related activity changes. bioRxiv. 2019. 24 pages. doi:10.1101/644526.

Mehta et al., Single-fluorophore biosensors for sensitive and multiplexed detection of signalling activities. Nat Cell Biol. Oct. 2018;20(10):1215-1225. doi: 10.1038/s41556-018-0200-6. Epub Sep. 24, 2018.

Miyamae et al., A Method for Conditional Regulation of Protein Stability in Native or Near-Native Form. Cell Chem Biol. Dec. 17, 2020;27(12):1573-1581.e3. doi: 10.1016/j.chembiol.2020.09.004. Epub Oct. 1, 2020.

Nguyen et al., In-Cell Engineering of Protein Crystals with Nanoporous Structures for Promoting Cascade Reactions. ACS Appl Nano Mater. 2021; 4(2): 1672-1681. doi: 10.1021/acsanm.0c03129.

O'Neill et al., Neuronal Calcium Recording with an Engineered TEV Protease. ACS Chem Biol. May 18, 2018;13(5):1159-1164. doi: 10.1021/acschembio.8b00130. Epub May 2, 2018.

Pélissier et al., GFP Tagging of Sieve Element Occlusion (SEO) Proteins Results in Green Fluorescent Forisomes. Plant Cell Physiol. Nov. 2008;49(11):1699-710. doi: 10.1093/pcp/pcn141. Epub Sep. 10, 2008.

Pisanello et al., Dynamic illumination of spatially restricted or large brain vols. via a single tapered optical assembly. Nat Neurosci. Aug. 2017;20(8):1180-1188. doi: 10.1038/nn.4591. Epub Jun. 19, 2017.

Pond et al., R-body-producing bacteria. Microbiol Rev. Mar. 1989;53(1):25-67. doi: 10.1128/mr.53.1.25-67.1989.

Renier et al., Mapping of Brain Activity by Automated vol. Analysis of Immediate Early Genes. Cell. Jun. 16, 2016;165(7):1789-1802. doi: 10.1016/j.cell.2016.05.007. Epub May 26, 2016.

Rodriques et al., Recording the age of RNA with deamination. bioRxiv. Posted Feb. 10, 2020. 18 pages. doi: 10.1101/2020.02.08.939983.

Rodriques et al., RNA timestamps identify the age of single molecules in RNA sequencing. Nat Biotechnol. Mar. 2021;39(3):320-325. doi: 10.1038/s41587-020-0704-z. Epub Oct. 19, 2020.

Sanchez et al., Directed evolution improves the catalytic efficiency of TEV protease. Nat Methods. Feb. 2020;17(2):167-174. doi: 10.1038/s41592-019-0665-7. Epub Dec. 9, 2019.

Sanchez et al., Transcriptional readout of neuronal activity via an engineered Ca2+-activated protease. Proc Natl Acad Sci U S A. Dec. 15, 2020;117(52):33186-33196. doi: 10.1073/pnas.2006521117. Online ahead of print.

Shen et al., De novo design of self-assembling helical protein filaments. Science. Nov. 9, 2018;362(6415):705-709. doi: 10.1126/science.aau3775.

Shukla et al., Molecular farming of fluorescent virus-based nanoparticles for optical imaging in plants, human cells and mouse models. Biomater Sci. May 1, 2014;2(5):784-797. doi: 10.1039/c3bm60277j. Epub Mar. 12, 2014.

Specht et al., A Critical and Comparative Review of Fluorescent Tools for Live-Cell Imaging. Annu Rev Physiol. Feb. 10, 2017;79:93-117. doi: 10.1146/annurev-physiol-022516-034055. Epub Nov. 16, 2016.

St-Onge et al., Temporal control of gene expression in transgenic mice by a tetracycline-responsive promoter. Proc Natl Acad Sci U S A. Sep. 27, 1994;91(20):9302-6. doi: 10.1073/pnas.91.20.9302.

Sun et al., Functionally Distinct Neuronal Ensembles within the Memory Engram. Cell. Apr. 16, 2020;181(2):410-423.e17. doi: 10.1016/j.cell.2020.02.055. Epub Mar. 17, 2020.

Sun et al., Synthesis of bioactive protein hydrogels by genetically encoded SpyTag-SpyCatcher chemistry. Proc Natl Acad Sci U S A. Aug. 5, 2014;111(31):11269-74. doi: 10.1073/pnas.1401291111. Epub Jul. 21, 2014.

Ting et al., Genetically encoded fluorescent reporters of protein tyrosine kinase activities in living cells. Proc Natl Acad Sci U S A. Dec. 18, 2001;98(26):15003-8. doi: 10.1073/pnas.211564598.

Tsutsui et al., A Diffraction-Quality Protein Crystal Processed as an Autophagic Cargo. Mol Cell. Apr. 2, 2015;58(1):186-93. doi: 10.1016/j.molcel.2015.02.007. Epub Mar. 12, 2015.

Ueda et al., Whole-Brain Profiling of Cells and Circuits in Mammals by Tissue Clearing and Light-Sheet Microscopy. Neuron. May 6, 2020;106(3):369-387. doi: 10.1016/j.neuron.2020.03.004.

Vetere et al., Chemogenetic Interrogation of a Brain-wide Fear Memory Network in Mice. Neuron. Apr. 19, 2017;94(2):363-374.e4. doi: 10.1016/j.neuron.2017.03.037.

Wu et al., The Temporal Pattern of cfos Activation in Hypothalamic, Cortical, and Brainstem Nuclei in Response to Fasting and Refeeding in Male Mice. Endocrinology. Mar. 2014;155(3):840-53. doi: 10.1210/en.2013-1831. Epub Jan. 9, 2014.

Zakeri et al., Peptide tag forming a rapid covalent bond to a protein, through engineering a bacterial adhesin. Proc Natl Acad Sci U S A. Mar. 20, 2012;109(12):E690-7. doi: 10.1073/pnas.1115485109. Epub Feb. 24, 2012.

Zamft et al., Measuring Cation Dependent DNA Polymerase Fidelity Landscapes by Deep Sequencing. PloS One. 2012;7(8):e43876. doi: 10.1371/journal.pone.0043876. Epub Aug. 22, 2012.

Zhang et al., Optogenetic control with a photocleavable protein, PhoCl. Nat Methods. Apr. 2017;14(4):391-394. doi: 10.1038/nmeth.4222. Epub Mar. 13, 2017.

(56) References Cited

PUBLICATIONS

Zhou et al., Optical control of cell signaling by single-chain photoswitchable kinases. Science. Feb. 24, 2017;355(6327):836-842. doi: 10.1126/science.aah3605.

* cited by examiner

| | $JF_{503}$ | $JF_{525}$ | $JF_{552}$ | $JFX_{608}$ | $JF_{669}$ |
|---|---|---|---|---|---|
| $\lambda_{abs}$ (nm) | 503 | 525 | 552 | 608 | 669 |
| $\varepsilon$ ($M^{-1}cm^{-1}$) | 83,000 | 94,000 | 95,000 | 111,000 | 112,000 |
| $\lambda_{em}$ (nm) | 529 | 549 | 575 | 628 | 682 |
| $\Phi_f$ | 0.87 | 0.91 | 0.83 | 0.74 | 0.37 |

USE OF PROTEIN ASSEMBLIES TO RECORD CELLULAR EVENTS

RELATED APPLICATIONS

This application claims priority under 35 U.S.C. § 119(e) to U.S. Provisional Application, U.S. Ser. No. 63/254,820, filed Oct. 12, 2021, which is incorporated herein by reference.

GOVERNMENT SUPPORT

This invention was made with government support under N00014-18-1-2858 awarded by U.S. Office of Naval Research (NAVY/ONR). The government has certain rights in this invention.

REFERENCE TO AN ELECTRONIC SEQUENCE LISTING

The contents of the electronic sequence listing (H082470397US01-SEQ-TNG.xml; Size: 5,242 bytes; and Date of Creation: Oct. 12, 2022) is incorporated by reference herein.

BACKGROUND OF THE INVENTION

A longstanding goal in biology is to map the dynamics of gene expression throughout a tissue or organism. Such maps could reveal mechanisms of spatial and temporal patterning, e.g., in brain activity, embryonic development, or disease progression. Fluorescent protein-based markers are a very powerful tool for mapping gene expression. However, optical imaging of fluorescent reporters typically faces a tradeoff between temporal and spatial information: vast numbers of cells can be imaged in fixed tissue,[26] but recording dynamic information (e.g., cellular events that may occur transiently during cell growth) requires live-tissue optical access, in which the field of view is limited by light scatter and optical instrumentation. These challenges are particularly evident when trying to image markers of neurological activity (e.g., brain activity), such as activity-responsive immediate early genes (IEGs), where relevant dynamics are broadly distributed throughout the brain.[63]

Imaging in fixed tissue can report organ-wide patterns of gene expression, but typically at only one[1,2] or at most two[3] timepoints. Time-lapse in vivo microscopy can report longitudinal gene expression dynamics,[4] but only in a small optically accessible region, limited by light-scatter and optical instrumentation; and in vivo imaging typically requires surgery and/or immobilization of the animal. The possibility of encoding organ-wide dynamics in DNA or RNA sequences has been explored,[5,6] but despite progress[7], such ideas have not yet been realized. Accordingly, tools to record the dynamics of cellular events in large numbers of cells, without constraints from in vivo imaging, are needed, and such tools could transform the ability to study cellular events over time in various cell types and tissues, including in the nervous system and other tissues.

SUMMARY OF THE INVENTION

The present disclosure provides methods, systems, compositions, polynucleotides, proteins (e.g., protein assembly monomers and protein assemblies), cells, and kits for recording the history of cellular events (e.g., neural activation) in a cell. Growing intracellular protein assemblies were engineered that can incorporate diverse fluorescent markers during growth to store linear ticker tape-like histories. An embedded visualizable tag (e.g., a HALOTAG® reporter) incorporates user-supplied dyes, leading to colored stripes whose boundaries map assembly growth to wall-clock time. Various strategies for linking visualizable modifications of the protein assemblies to the occurrence of a cellular event of interest are described herein to record the history of cellular events (e.g., neural activity) in a cell. In some embodiments, high-resolution multispectral imaging on fixed cell samples is used to read the cells' histories (i.e., the protein assemblies are imaged inside the cells). Recordings of cellular events were demonstrated in ensembles of cultured cells with single-cell accuracy. The protein-based assemblies described herein may achieve massively parallel recordings of multiple cellular events and may be useful for profiling the effect of a stimulus (e.g., a candidate therapeutic agent) on cellular events over time.

Thus, in one aspect, the present disclosure provides methods for profiling one or more cellular events over time in a cell. The methods described herein utilize cells that have been engineered to produce growing intracellular protein assemblies that incorporate markers (e.g., colored bands, which may be fluorescent) at particular times during growth. Protein assembly growth can thus be mapped and correlated to wall-clock time (i.e., the actual time elapsed as recorded on a clock or other time-keeping device), facilitating the study of the timing of particular cellular events. The protein assemblies are further engineered such that they undergo a modification or change during cellular events of interest that is also visualizable. Thus, in the methods disclosed herein, a cell transfected, transduced, electroporated, or injected with a first polynucleotide encoding a protein assembly monomer and a second polynucleotide encoding a protein assembly monomer is incubated for a period of time. The protein assembly monomer expressed from one polynucleotide may be engineered in such a way that a cellular event leads to expression of the protein monomer or a visualizable change or modification to the protein monomer. In certain embodiments, the protein monomer expressed from the other polynucleotide is modified to introduce markings that correlate with time onto the protein assembly. The protein assemblies may then be visualized to determine if, and at what time points, a cellular event has occurred. Various strategies for marking time in the protein assemblies (e.g., dye-based strategies and optogenetic strategies) and for modifying the protein assemblies during occurrences of a cellular event (e.g., utilizing fluorescent proteins, proteases, post-translational modifications by particular cellular enzymes, etc.) are described herein. Such strategies may be used in the methods disclosed herein in isolation, or may be combined (e.g., to profile multiple different cellular events over time in a cell simultaneously).

In some embodiments, the present disclosure provides a method of profiling one or more cellular events in a cell over time comprising incubating a cell for a period of time, wherein the cell comprises: (i) a first polynucleotide encoding a first protein assembly monomer under control of a first promoter; and (ii) a second polynucleotide encoding a second protein assembly monomer under control of a second promoter, wherein a cellular event leads to expression of the first and/or second protein monomer or a visualizable change or modification of the first and/or second protein monomer in a protein assembly. Any cellular event that can be connected to expression of a protein assembly monomer, or a visualizable change or modification to a protein assembly monomer, may be profiled using the methods described herein. For example, expression of one or more genes or proteins of interest within a cell may be profiled. In some embodiments, enzymatic activity (e.g., kinase activity, phosphatase activity, ubiquitylation, sumoylation, nitrosylation, glycosylation, lipidation, acylation, farnesylation, alkylation, amidation, carboxylation, hydroxylation, succinylation, sulfation, or any other post-translational modification mediated by an enzyme) may be profiled in a cell. Metabolic activity in a cell (e.g., the presence or absence of a metabolite of interest, or a change in concentration of a metabolite of interest) may also be profiled in a cell. In some embodiments, a change in concentration of an ion may be profiled in a cell. The change in concentration of an ion may be associated with a neurological event (e.g., transmission of a signal by the nervous system). In some embodiments, a change in concentration of a small molecule, or the presence or absence of a small molecule (a signaling molecule, for example) may be profiled. In some embodiments, any process related to cell differentiation, cell growth, or cell division may be profiled. In certain embodiments, the cellular event comprises neuronal activity (e.g., transmission of a nerve signal) or activity in cardiac muscle. In certain embodiments, the cellular event comprises cell differentiation, cell growth, or cell division.

In some embodiments, the present disclosure provides methods for profiling a cellular event over time comprising:

a) incubating a cell, wherein the cell comprises:
    - a first polynucleotide encoding a protein assembly monomer fused to a visualizable tag under control of a first promoter; and
    - a second polynucleotide encoding a protein assembly monomer fused to a visualizable protein under control of a second promoter, wherein activation of the second promoter is associated with an occurrence of the cellular event being profiled;

for a period of time $t_1$ in the presence of a first fluorescent dye that binds to the visualizable tag, thereby allowing the protein assembly monomers expressed by the first and second polynucleotides to assemble into a protein assembly;

b) further incubating the cell for a period of time $t_2$ in the presence of a second fluorescent dye that binds to the visualizable tag, thereby allowing the protein assembly monomers expressed by the first and second polynucleotides to further assemble onto the protein assembly; and c) imaging the protein assembly.

In some embodiments, the protein assembly is imaged in the cell. In some embodiments, the protein assembly is imaged to determine the location of the protein assembly monomer fused to the visualizable protein relative to the locations of the first and the second fluorescent dyes bound to the visualizable tag, thereby determining the times at which the cellular event occurs.

In some embodiments, the present disclosure provides methods for profiling a cellular event over time comprising:

a) incubating a cell, wherein the cell comprises:
    - a first polynucleotide encoding a protein assembly monomer fused to a light-gated tag under control of a first promoter; and
    - a second polynucleotide encoding a protein assembly monomer fused to a visualizable protein under control of a second promoter, wherein activation of the second promoter is associated with an occurrence of the cellular event being profiled;

for a period of time $t_1$ in the absence of illumination that releases the light-gated tag, thereby allowing the protein assembly monomers to assemble into a protein assembly;

b) further incubating the cell for a period of time $t_2$ in the presence of illumination that releases the light-gated tag, thereby allowing the protein assembly monomers to further assemble onto the protein assembly; and c) imaging the protein assembly.

In some embodiments, the protein assembly is imaged in the cell. In some embodiments, the protein assembly is imaged to determine the location of the protein assembly monomer fused to the visualizable protein relative to the locations of the released light-gated tags, thereby determining the times at which the cellular event occurs. In some embodiments, the light-gated tags are only incorporated into the protein assembly after being exposed to light of a specific wavelength.

In some embodiments, the present disclosure provides methods for profiling a cellular event over time comprising:

a) incubating a cell, wherein the cell comprises:
    - a first polynucleotide encoding a protein assembly monomer fused to a visualizable tag susceptible to protease cleavage under control of a first promoter; and
    - a second polynucleotide encoding a protease under control of a second promoter, wherein the protease cleaves the visualizable tag from the protein assembly monomer during an occurrence of the cellular event;

for a period of time $t_1$ in the presence of a first fluorescent dye that binds to the visualizable tag, thereby allowing the protein assembly monomers expressed by the first and second polynucleotides to assemble into a protein assembly;

b) further incubating the cell for a period of time $t_2$ in the presence of a second fluorescent dye that binds to the visualizable tag, thereby allowing the protein assembly monomers expressed by the first and second polynucleotides to further assemble onto the protein assembly; and c) imaging the protein assembly.

In some embodiments, the protein assembly is imaged in the cell. In some embodiments, the protein assembly is imaged to determine the location of the protein assembly monomers cleaved by the protease relative to the locations of the first and the second fluorescent dyes bound to the visualizable tag, thereby determining the times at which the cellular event occurs.

In some embodiments, the present disclosure provides methods for profiling a cellular event over time comprising:

a) incubating a cell, wherein the cell comprises:
    - a first polynucleotide encoding a protein assembly monomer fused to a visualizable tag under control of a first promoter; and
    - a second polynucleotide encoding a protein assembly monomer fused to a visualizable protein under control of a second promoter, wherein the visualizable protein is visualizable only after being modified due to a cellular event;

for a period of time $t_1$ in the presence of a first fluorescent dye that binds to the visualizable tag, thereby allowing the protein assembly monomers expressed by the first and second polynucleotides to assemble into a protein assembly;

b) further incubating the cell for a period of time $t_2$ in the presence of a second fluorescent dye that binds to the visualizable tag, thereby allowing the protein assembly monomers expressed by the first and second polynucleotides to further assemble onto the protein assembly; and c) imaging the protein assembly.

In some embodiments, the protein assembly is imaged in the cell. In some embodiments, the protein assembly is imaged to determine the location of the protein assembly monomer fused to the visualizable protein relative to the locations of the first and the second fluorescent dyes bound to the visualizable tag, thereby determining the times at which the cellular event occurs.

In some embodiments, the present disclosure provides methods for profiling a cellular event over time comprising:

a) incubating a cell, wherein the cell comprises:
   a first polynucleotide encoding a protein assembly monomer fused to a visualizable tag under control of a first promoter; and
   a second polynucleotide encoding a protein assembly monomer fused to a binding moiety under control of a second promoter, wherein the binding moiety binds a molecule associated with an occurrence of a cellular event being profiled;

for a period of time $t_1$ in the presence of a first fluorescent dye that binds to the visualizable tag, thereby allowing the protein assembly monomers expressed by the first and second polynucleotides to assemble into a protein assembly;

b) further incubating the cell for a period of time $t_2$ in the presence of a second fluorescent dye that binds to the visualizable tag, thereby allowing the protein assembly monomers expressed by the first and second polynucleotides to further assemble onto the protein assembly; and c) analyzing the identity of the molecule bound to the binding moiety to determine whether the cellular event occurred.

Any of the methods described herein may also be useful for profiling the effect of a stimulus, such as a candidate therapeutic agent or other stimulus (e.g., a candidate therapeutic agent, or some other stimulus, such as light, heat, or an electrical impulse), on a cell over time. For example, a cell may be incubated as in the methods described herein, wherein the cell is being treated with or has previously been treated with a stimulus. If a difference in the profile of the cellular event in the treated cell compared to the cell that was not treated is observed, this may indicate that the stimulus modulates the cellular event of interest (or multiple cellular events of interest).

Thus, in some embodiments, the present disclosure provides methods for profiling the effect of a stimulus on a cellular event over time comprising:

a) incubating a cell for a period of time that is being treated with or has been treated with a stimulus, wherein the cell comprises:
   a first polynucleotide encoding a first protein assembly monomer under control of a first promoter;
   a second polynucleotide encoding a second protein assembly monomer under control of a second promoter;

wherein a cellular event leads to expression of the first and/or second protein monomer or a visualizable change or modification of the first and/or second protein monomer in a protein assembly; and wherein a difference in the profile of the cellular event over time in the cell treated with the stimulus relative to a cell not treated with the stimulus indicates that the stimulus modulates the cellular event.

The present disclosure also provides proteins (e.g., any of the protein assemblies described herein), polynucleotides (e.g., vectors), and pairs of polynucleotides for use in the methods provided herein. In some embodiments, each polynucleotide in the pair of polynucleotides encodes a different protein assembly monomer, or the same protein assembly monomer fused to a different visualizable tag, protein, or other fusion partner. Cells comprising any of the polynucleotides provided herein are also provided by the present disclosure. The present disclosure also provides systems comprising any of the proteins and/or polynucleotides described herein. In some embodiments, the systems also comprise a microscope and/or a computer. Kits comprising any of the proteins, polynucleotides (e.g., vectors), or pairs of polynucleotides described herein are also provided by the present disclosure and may be useful for performing any of the methods for profiling cellular events over time described herein.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present disclosure, which can be better understood by reference to one or more of these drawings in combination with the Detailed Description of Certain Embodiments presented herein.

FIG. 1A provides a scheme for intracellular recording of cFos activity with fiducial timestamps. iPAK4 forms the assembly scaffold. HALOTAG®-iPAK4 incorporates HALOTAG® (HT) dyes, as provided herein, permitting labeling of the assembly with fiducial timestamps. Neural activation drives expression of cFos::eGFP-iPAK4, introducing eGFP bands into the assembly. FIG. 1B shows the composition of the protein constructs used to label intracellular protein assemblies. FIG. 1C shows the structures of tagged iPAK4 monomers and the crystal structure with hexagonal pores (from PDB:4XBR), modeled using Protein Imager software.[39] FIG. 1D provides an image of a HEK cell expressing CMV::iPAK4 (95%) and CMV::HT-iPAK4 (5%). The assembly was stained with $JFX_{608}$, the membrane was labeled by expressing GPI-eGFP, and the nucleus was labeled with DAPI. Scale bar 10 μm. FIG. 1E shows growth profiles of iPAK4 assemblies in HEK cells (n=46 assemblies). FIG. 1F shows the population average (black) and standard deviation (shaded area) of the linear-phase assembly growth (light gray lines). Each assembly's linear-phase growth profile was mapped to the interval [0, 1]. FIGS. 1G-1I show statistics of assembly growth, showing (FIG. 1G) assembly length at the transition from initial nucleation to linear growth, (FIG. 1H) linear-phase growth rate, and (FIG. 1I) $R^2$ of the fit of the linear-phase growth to a straight line. In FIGS. 1E-1I, assemblies were randomly selected. Box bounds: 25th and 75th percentile; whiskers: minimum and maximum; squares: mean; center lines: median. All data points are displayed.

FIG. 2A provides a scheme for multi-color labeling of intracellular iPAK4 assemblies. FIG. 2B provides images of iPAK4 assemblies labeled with four dye transitions on each end. Triangles indicate timing of dye addition. JF503, JF669, and $JFX_{608}$ were used. Scale bars 5 μm. FIG. 2C shows a comparison of two ends of a single assembly. Images of the two ends are provided (top). In this case, the assembly split at one of its ends, an occurrence in approximately 10% of assemblies. Quantification of the fluorescence traces in the two ends, with position normalized to the locations of the first $JF_{669}$ addition and the end of the assembly, is also shown (bottom). Scale bar 5 μm. FIG. 2D shows a comparison of dye transition points on the faster and slower-growing assembly ends. The scatter plot shows the positions of the $JFX_{608}$, $JF_{503}$, and $JF_{669}$ transitions normalized relative to the first $JF_{669}$ addition (at position 0) and the end of the assembly (at position 1). The plots show the mean fluorescence profiles of N=22 assemblies. FIG. 2E shows mean fluorescence profiles of assemblies exposed to the same sequence of dyes and then grown for different amounts of time (N=22 fixed at 8 h, 12 fixed at 30 h). The overlap of these profiles indicates negligible monomer exchange over 22 h. FIG. 2F shows an assembly profile with seven dye switches separated by 1 h. Scale bar 5 μm. FIG. 2G shows a comparison of the growth rate on the two ends after one dye switch. The long end and short end correspond to the faster and slower growing end, respectively (N=153 assemblies). The growth rate on the slower-growing end was 0.77±0.05-fold lower than on the faster-growing end (95% C.I.).

FIG. 3A shows an experimental design for testing the precision with which addition of $JFX_{608}$ could be determined relative to timestamps from addition of $JF_{669}$ (at t=0) and $JF_{525}$ (at t=10 h). FIG. 3B provides a histogram of growth rates between the timestamps at t=0 and t=10 h. FIG. 3C shows images of assemblies with $JFX_{608}$ addition at t=2, 4, 6, and 8 h (top) and fluorescence line profiles (bottom). Scale bars 10 μm. FIG. 3D shows fluorescence profiles of N=223 assembly ends with JFX608 addition at different timepoints (top). The profile lengths have been normalized to line up the timestamps at t=0 and 10 h. FIG. 3D also shows mean fluorescence traces in each of the three dye color channels for all times of $JFX_{608}$ addition (bottom). FIG. 3E shows positions of the $JFX_{608}$ onset as a function of dye addition time (top) and standard deviation in the inferred timing of $JFX_{608}$ addition for each population of assemblies (bottom). Lower and upper bounds of the box plot: 10th and 90th percentile; lower and upper whiskers: minimum and maximum; squares: mean; center lines: median. All data points are displayed. FIG. 3F shows low-magnification (left) and magnified (right) images of iPAK4 assemblies in HEK cells. Scale bar 100 μm.

FIG. 4A shows genetic constructs for recording time-tagged transcription activation. FIGS. 4B-4C show representative images of assemblies with DOX addition at t=2, 4, or 6 h (top) and fluorescence line profiles (bottom). Scale bars: 10 μm. FIG. 4D shows normalized positions of eGFP onset relative to fiducial timestamps at t=0 and 8 h. The linear fit has a y-intercept of 1.2 h, indicative of the delay between DOX addition and protein synthesis. Lower and upper bounds of the box plot: 10th and 90th percentile; lower and upper whiskers: minimum and maximum; squares: mean; center lines: median. All data points are displayed.

FIG. 5A provides an image of a cultured neuron expressing lentiviral CMV::iPAK4 (90%) and CMV::eGFP-iPAK4 (10%). Scale bar 50 μm. FIG. 5B shows representative patch clamp recordings in neurons with or without an iPAK4 assembly. Spikes were evoked by a current injection of 100 pA. FIG. 5C shows that there were no significant differences between neurons with or without assemblies in membrane resistance (404±73 Mn vs 339±43 MΩ, p=0.43), membrane capacitance (63±6 pF vs 67±9, p=0.67), resting potential (−61.2±1.2 mV vs −60.2±0.8 mV, p=0.48), or rheobase (89±12 pA vs 109±13 pA, p=0.27, N=11 neurons with assemblies, 12 neurons without). Error bars show mean±s.e.m. Two-sided Student's t-test was employed for data comparison. FIG. 5D shows images of an assembly in a neuron expressing lentiviral CMV::iPAK4 (90%) and cFos::eGFP-iPAK4 (10%). The top image shows the assembly after a first phorbol 12-myristate 13-acetate (PMA) addition, and the bottom image shows the same assembly after a second PMA addition. Scale bar 5 μm. FIG. 5E shows genetic constructs for recording time-tagged cFos activation in neurons. FIG. 5F shows an experimental protocol for recording time-tagged cFos activation in neurons. Transitions to $JF_{669}$ at t=0 and to $JF_{552}$ at t=12 h provide fiducial timestamps. cFos was activated via addition of PMA at t=3, 6, or 9 h. FIG. 5G provides representative images of assemblies with PMA addition at t=3, 6, or 9 h (top) and fluorescence line profiles (bottom). Scale bar 5 μm. FIG. 5H shows normalized positions of eGFP onset relative to fiducial timestamps at t=0 and 12 h. Lower and upper bounds of the box plot: 10th and 90th percentile, respectively; lower and upper whiskers: minimum and maximum, respectively; squares: mean; center lines: median. The linear fit has a y-intercept of ca. 1.0 h. All data points are displayed.

FIG. 6A provides images of HEK293T cells expressing CMV::iPAK4 (95%) and CMV::HT-iPAK4 (5%). The assemblies were stained with $JFX_{608}$ and the membrane was labeled by expressing GPI-eGFP. In cells where the assembly length exceeded the cell size, the membrane wrapped around the extended assembly. FIG. 6B shows nucleation and growth of a single eGFP-labeled iPAK4 assembly. HEK293T cells co-expressed CMV::iPAK4 (95%) and CMV::eGFP-iPAK4 (5%). Time-lapse video microscopy was acquired over a 13 h interval starting 10 h after transfection, with one frame every 10 min. Assemblies were tracked using a Radon transform algorithm. The assembly nucleated ~8.5 h after the start of the recording, grew rapidly for the first ~20 min, and then slowed. Assembly nucleation and initial growth were accompanied by a decrease in cytoplasmic eGFP fluorescence. A kymograph showing the assembly profile is also provided (bottom).

FIG. 7B shows a simulation of assembly nucleation and growth. Initially, monomers accumulate, and monomer synthesis is partially compensated by protein degradation. At t=0, the monomer concentration crosses the nucleation threshold, leading to a period of rapid growth until the monomer concentration reaches a level where protein synthesis and removal via assembly growth are balanced. FIG. 7C shows a multi-component kinetic model comprising iPAK4 with a HALOTAG® ligand and bare iPAK4. The labeling ratio of the HT-iPAK4 is proportional to the mole-fraction of each dye at the time of protein translation. FIG. 7D shows simulations of assembly growth profiles with a step-wise replacement of one dye for another. (i) Dye switch after assembly nucleation; (ii) dye switch before assembly nucleation. FIG. 7E shows a representative iPAK4 assembly growth profile (solid dark gray line) and images at key frames (background) after the crystal nucleation. Simulated growth profile (dashed line) and cytosolic iPAK4 concentration (solid light gray line).

FIG. 8A shows representative images of two iPAK4 assemblies with different amounts of eGFP-iPAK4, taken from the same plate. FIG. 8B shows the linear-phase growth rate of iPAK4 assemblies as a function of the fluorescence intensity of eGFP-iPAK4 in the assembly (N=46 assemblies, Pearson r=−0.05; p=0.75). FIG. 8C shows representative images of two iPAK4 assemblies with different amounts of HT-iPAK4, taken from the same plate. FIG. 8D shows the linear-phase growth rate of iPAK4 assemblies as a function of the fluorescence intensity of HT-iPAK4 in the assembly (N=46 assemblies, Pearson r=−0.02; p=0.89).

FIG. 9B shows a control group with the same culture conditions but without lentiviral transduction of iPAK4 constructs. Live cells (calcein-AM), dead cells (EthD-1), and HALOTAG®-iPAK4 stained with $JFX_{608}$ are shown. FIG. 9C provides a statistical comparison of the dead cell population in iPAK4+ and iPAK4− groups. Each point represents one field of view. Two dishes per condition were investigated. No significant difference was found between the two groups. The statistical comparison was performed by student's t-test. Lower and upper bounds of the box plot: 25th and 75th percentile; lower and upper whiskers: minimum and maximum; squares: mean; center lines: median.

FIGS. 10A-10B provide snapshots showing mitosis and cell divisions of a HEK293T cell containing an iPAK4 assembly. FIG. 10C shows a cell expressing iPAK4 and eGFP-iPAK4 but without an iPAK4 assembly. FIG. 10D shows a cell not expressing iPAK4. In all cases mitosis appeared to proceed normally. Hoechst 33342 nuclear stain GFP-iPAK4 are shown. Scale bar 20 μm.

FIG. 11A shows the chemical structures and spectral properties of the free Janelia Fluor: $JF_{503}$, $JF_{525}$, $JF_{552}$, $JFX_{608}$, and $JF_{669}$. FIG. 11B shows the synthesis of $JFX_{608}$-HALOTAG®.

FIG. 12B provides low-magnification images showing representative FOVs after the four dye switches. Scale bars: 200 μm. FIG. 12C provides magnified images showing the representative FOVs after the four dye switches. Scale bars: 50 μm. FIG. 12D provides images of single HT-iPAK4 assemblies labeled with four dye transitions on each end. Scale bars 10 μm. FIG. 12E shows an assembly end-tagged with seven dye transitions at Δt=1 h. Scale bar 5 μm (FIGS. 12D-12E). Each image panel shows a composite image of an assembly (top), the three color channels individually (middle), and the line-profiles through each color channel (bottom). Blue: $JF_{525}$, Yellow: $JFX_{608}$, Red: $JF_{669}$. Scale bars 10 μm.

FIG. 13A shows a mean fluorescence profile of assemblies with dye switches $JF_{525}$ to $JF_{669}$ at t=0 and $JF_{669}$ to $JF_{525}$ at t=10 h (N=200 assemblies, length normalized to 0-1). The half-life of soluble labeled HT-iPAK4 was 4.5 h, set by the rate of incorporation into the growing assembly. The sharpness of the dye transition was 7.5 min, as calculated by the width of the peak in the second derivative of fluorescence vs. position (as shown by arrows). FIGS. 13B-13C show kinetics of HT dye reaction in HEK293T cells. HEK293T cells expressing a nucleus-targeted HT construct (HT-NLS, Addgene #82518) were incubated with 0.1 μM of the indicated dye (FIG. 3B) or 1 μM of the indicated dye (FIG. 3C), and nuclear fluorescence was monitored as a function of time. In FIG. 3B, HT-iPAK4 labeling experiments were performed with 10-fold higher dye concentrations (1 μM).

FIG. 16A shows an experimental protocol for recording the time-tagged response of eGFP-iPAK4 expression triggered by a brief pulse of DOX exposure. Transitions to $JF_{669}$ at t=0 and to $JFX_{608}$ at t=8 h provided fiducial timestamps. Transcription was activated via addition of 2 μg/mL DOX at t=−0.5 h, followed by a thorough wash at t=0 h. FIG. 16B provides three representative examples showing the GFP intensity profiles on the protein ticker tapes. Top: representative images. Bottom: fluorescence line profiles. Scale bars: 10 mm.

FIG. 17A shows genetic constructs for Tet-ON control of the iPAK4 scaffold. FIG. 17B shows an experimental protocol for controlling the onset of iPAK4 expression and assembly growth. DOX was added at day 7 after lentiviral transduction. FIG. 17C provides representative images taken at different days after lentiviral transduction. Scale bar 100 mm.

FIG. 18A shows growth profiles aligned by nucleation time (N=22). FIG. 18B shows mean (black) and standard deviation (shaded area) of growth profiles during the linear growth phase (N=22, light gray lines). FIGS. 18C-18E provide statistics of assembly growth, showing (FIG. 18C) assembly length at the transition from initial nucleation to linear growth. FIG. 18D shows the linear-phase growth rate. FIG. 18E shows $R^2$ of the fit of the linear-phase growth to a straight line. In FIGS. 18C-18E, assemblies were randomly selected. Box bounds: $25^{th}$ and $75^{th}$ percentile; whiskers: minimum and maximum; squares: mean; center lines: median. All data points are displayed. FIG. 18F shows representative iPAK4 assembly growth profile in a cultured neuron (solid dark gray line) and images at key frames (background). Simulated growth profile (dashed line) and cytosolic iPAK4 concentration (solid light gray line) are shown.

FIG. 19B shows distribution of the assembly count per cell in neurons. The assembly count was categorized into 0, 1, and >1 assemblies per cell.

FIG. 20B provides low-magnification images showing representative FOVs after the three dye switches. Scale bars: 100 mm. FIG. 20C provides magnified images showing the representative FOVs after the three dye switches. Scale bars: 20 mm.

FIG. 22A shows primary neuron culture infected by CMV::iPAK4 (95%) and CMV::HT-iPAK4 (5%) lentiviruses with assembly formation in the cells. FIG. 22B shows neuron culture without any lentiviral infection. Staining of live cells (calcein-AM) and dead cells (EthD-1) is shown. The assay was performed at day 6 after lentiviral infection. Many iPAK4 assemblies are present in FIG. 22A (assemblies share the channel with calcein-AM). Scale bars: 200 μm. FIG. 22C provides a statistical comparison of the live-cell and dead-cell populations, and the dead/live cell ratio in iPAK4+ and iPAK4− groups (N=5 fields of view per group).

FIG. 23A provides an example of an assembly inside a neuron. The outline of the neuron is shown with a dotted line. Scale bar 20 μm. FIG. 23B shows examples of individual assemblies showing onset of eGFP fluorescence upon addition of PMA. Scale bars 5 μm.

FIG. 25A shows that a $Ca^{2+}$-dependent protease imparts dark markers on the growing assembly. FIG. 25B shows that kinases irreversibly modulate fluorescence of single-fluorophore or fluorescence resonance energy transfer (FRET) reporters during incorporation into the assembly. In both approaches, HT dyes impart fiducial timestamps.

DEFINITIONS

Figure 1A:
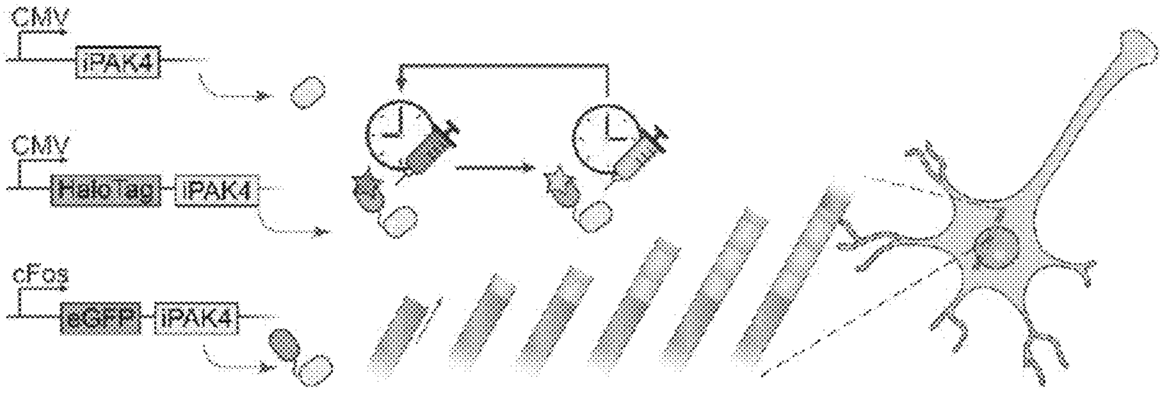
FIGS. 1A-1I show that iPAK4 forms intracellular protein assemblies.

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd ed. 1994); *The Cambridge Dictionary of Science and Technology* (Walker ed., 1988); *The Glossary of Genetics,* 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

A "cell," as used herein, may be present in a population of cells. In some embodiments, a population of cells is composed of a plurality of different cell types. Virtually any cell type can be used in the methods described herein. In some embodiments, the cells are prokaryotic cells. In some embodiments, the cells are eukaryotic cells. In some embodiments, the cells are bacterial cells. In some embodiments, the cells are mammalian cells (e.g., complex cell populations such as naturally occurring tissues). In some embodiments, the cells are human cells. In certain embodiments, the cells are collected from a subject (e.g., a human). Alternatively, the cells are from a cultured population (e.g., a culture derived from a complex population or a culture derived from a single cell type where the cells have differentiated into multiple lineages). In certain embodiments, the cells are from an established cell line. In certain embodiments, the cells are primary cells (e.g., the cells are taken directly from living tissue). In certain embodiments, the cells are HEK cells. In some embodiments, the cells are neurons. In certain embodiments, the cells are primary hippocampal nerve cells. Any cell type may be used in the methods of the present disclosure, including, but are not limited to, stem and progenitor cells (e.g., embryonic stem cells, hematopoietic stem cells, mesenchymal stem cells, neural crest cells, etc.), endothelial cells, muscle cells, myocardial cells, smooth and skeletal muscle cells, mesenchymal cells, epithelial cells, hematopoietic cells, lymphocytes such as T-cells (e.g., Th1 T cells, Th2 T cells, ThO T cells, cytotoxic T cells) and B cells (e.g., pre-B cells), monocytes, dendritic cells, neutrophils, macrophages, natural killer cells, mast cells, adipocytes, immune cells, neurons, hepatocytes, and cells involved with particular organs (e.g., thymus, endocrine glands, pancreas, brain, neurons, glia, astrocytes, dendrocytes, and genetically modified cells thereof). The cells may also be transformed or neoplastic cells of different types (e.g., carcinomas of different cell origins, lymphomas of different cell types, etc.) or cancerous cells of any kind. Cells of different origins (e.g., ectodermal, mesodermal, and endodermal) are also contemplated for use in the methods and systems of the present disclosure.

The term "cellular event" refers to any process within a cell. In some embodiments, a cellular event comprises expression of one or more genes, or expression of one or more proteins. In some embodiments, a cellular event comprises enzymatic activity (e.g., kinase activity, phosphatase activity, ubiquitylation, sumoylation, nitrosylation, glycosylation, lipidation, acylation, farnesylation, alkylation, amidation, carboxylation, hydroxylation, succinylation, sulfation, or any other post-translational modification mediated by an enzyme). In some embodiments, a cellular event comprises metabolic activity in a cell. In some embodiments, a cellular event comprises the presence or absence of a molecule (e.g., a metabolite or other small molecule), or a change in concentration of a molecule. In some embodiments, a cellular event comprises a change in the concentration of an ion. In some embodiments, a cellular event comprises cell differentiation, cell growth, or cell division.

The terms "polynucleotide," "nucleotide sequence," "nucleic acid," "nucleic acid molecule," "nucleic acid sequence," and "oligonucleotide" refer to a series of nucleotide bases (also called "nucleotides") in DNA and RNA and mean any chain of two or more nucleotides. The polynucleotides can be chimeric mixtures or derivatives or modified versions thereof, and single-stranded or double-stranded. The oligonucleotide can be modified at the base moiety, sugar moiety, or phosphate backbone, for example, to improve stability of the molecule, its hybridization parameters, etc. In some embodiments, a polynucleotide is useful for expressing one or more genes (e.g., the polynucleotide may comprise a plasmid or other expression vector). In certain embodiments, the polynucleotide may include a promoter to control expression of one or more genes. In some embodiments, the polynucleotide encodes a protein assembly monomer. In certain embodiments, the polynucleotide encodes a protein assembly monomer fused to a visualizable tag (e.g., HALOTAG®), a protein assembly monomer fused to a visualizable protein (e.g., GFP), or any of the other protein assembly monomer fusions described herein.

A "promoter" as used herein refers to a nucleic acid sequence to which proteins bind to initiate transcription of RNA from the DNA downstream of the promoter. The RNA may encode a protein. In some embodiments, a promoter is an "activity-dependent promoter." An activity-dependent promoter is a promoter whose activation is associated with an occurrence of a particular cellular event (e.g., a cellular event being profiled using the methods described herein). The expression of a gene under control of an activity-dependent promoter may be activated, for example, by the presence of a particular molecule (e.g., a small molecule, nucleic acid, peptide, or protein) that is associated with a cellular event of interest. In some embodiments, a promoter is an "activity-independent promoter," which includes any promoter whose activation is not associated with an occurrence of a particular cellular event. Activity-independent promoters may also be referred to as constitutive promoters.

A "protein," "peptide," or "polypeptide" comprises a polymer of amino acid residues linked together by peptide bonds. The term refers to proteins, polypeptides, and peptides of any size, structure, or function. Typically, a protein will be at least three amino acids long. A protein may refer to an individual protein or a collection of proteins. Proteins may contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, synthetic, or any combination of these.

A "protein assembly" refers to a protein scaffold composed of multiple monomers, referred to herein as "protein assembly monomers" or simply "monomers." A protein assembly can be composed of the same monomer. For example, a protein assembly may be composed of multiple monomers that are the same, except for various modifications as described herein. In some embodiments, a protein assembly is composed of multiple different monomers. A protein assembly monomer may also be referred to herein as a "filament-forming protein." Any protein that can spontaneously assemble (i.e., self-assemble) in cells to form a protein assembly may be used in the methods provided in the present disclosure. In some embodiments, the protein assembly monomers comprise bacterial R-bodies as described in Pond, F. R. et al. *Microbiol. Mol. Biol. Rev.* 53, 25-67 (1989), plant forisomes as described in Pelissier, H. C. et al. *Plant Cell Physiol.* 49, 1699-1710 (2008), amyloid fibrils as described in LeVine, H. et al. *Methods in Enzymology* 309, 274-284, prions as described in Barmada, S. J. et al. *J. Neurosci.* 25, 5824-5832 (2005), filamentous viruses as described in Shukla, S. et al. *Biomater. Sci.* 2, 784-797 (2014), crystals of the fluorescent protein XpA as described in Tsutsui, H. et al. *Mol. Cell* 58, 186-193 (2015), engineered fiber-forming peptides as described in Shen, H. et al. *Science* 362, 705-709, engineered lattice-forming peptides as described in Nguyen, T. K. et al. *ACS Appl. Nano Mater.* 4, 1672-1681 (2021), or polymers of SpyTag peptide and SpyCatcher protein as described in Zakeri, B. et al. *Proc. Natl. Acad. Sci.* 109, E690-E697 (2012) and Sun, F. et al. *Proc. Natl. Acad. Sci.* 111, 11269-11274 (2014). In some embodiments, the protein assembly monomers comprise crystals of the kinase PAK4. Certain protein assembly monomers may have preferred characteristics for use in the methods provided herein, as is described further in the present disclosure.

DETAILED DESCRIPTION OF CERTAIN EMBODIMENTS

The aspects described herein are not limited to specific embodiments, systems, compositions, methods, or configurations, and as such can, of course, vary. The terminology used herein is for the purpose of describing particular aspects only and, unless specifically defined herein, is not intended to be limiting.

The present disclosure provides methods for profiling cellular events in a cell over time using protein assemblies as a recording medium. Typically, the protein assemblies are intracellular. Methods for profiling the effect of a stimulus, such as a candidate therapeutic agent or other stimulus as described herein, are also provided by the present disclosure. Proteins (e.g., any of the protein assembly monomers, protein assemblies, or modified derivatives thereof described herein), polynucleotides (e.g., vectors), and pairs of polynucleotides for use in the methods described herein, as well as systems and kits comprising such proteins, polynucleotides, and pairs of polynucleotides, are also provided herein.

Methods for Profiling Cellular Events in a Cell Over Time

In one aspect, the present disclosure provides methods for profiling a cellular event, or multiple cellular events (e.g., 2, 3, 4, 5, 6, 7, 8, 9, or more cellular events), in a cell. Cells are engineered to produce intracellular protein assemblies that incorporate markers (e.g., colored bands, which may be fluorescent) during growth, allowing protein assembly growth to be mapped and correlated to wall-clock time (i.e., the actual time elapsed as recorded on a clock or other time-keeping device). In some embodiments, the protein assemblies are slowly growing. The protein assemblies are further engineered such that they undergo a visualizable change during a cellular event, or are expressed only during a cellular event. The visualizable change may happen only when the event is taking place, during the entire event, at the end of the event, the whole time the event is taking place, or any combination thereof. Thus, in the methods disclosed herein, a cell transfected, transduced, electroporated, or injected with a first polynucleotide encoding a first protein assembly monomer and a second polynucleotide encoding a second protein assembly monomer is incubated for a period of time. The protein assemblies may be engineered in such a way that a cellular event leads to expression of one of the protein assembly monomers, or to a visualizable change or modification to one of the protein monomers. The protein assemblies may then be visualized to determine if, and at what time points, a cellular event has occurred. Various strategies for marking time in the protein assemblies (e.g., dye-based strategies and optogenetic strategies) and for modifying the protein assemblies during occurrences of a cellular event (e.g., utilizing fluorescent proteins, proteases, activity of particular cellular enzymes, etc.) are described herein. Such strategies may be used in the methods disclosed herein in isolation, or may be combined (e.g., to profile multiple different cellular events over time in a cell simultaneously). In some embodiments, the methods described herein are performed in vitro. In some embodiments, the methods described herein are not performed in a living subject. In some embodiments, the methods described herein are not performed in a human. In certain embodiments, the methods described herein are performed in vivo.

In some embodiments, the present disclosure provides a method of profiling one or more cellular events in a cell over time comprising incubating a cell for a period of time, wherein the cell comprises: (i) a first polynucleotide encoding a first protein assembly monomer under control of a first promoter; and (ii) a second polynucleotide encoding a second protein assembly monomer under control of a second promoter, wherein a cellular event leads to expression of the first and/or second protein monomer or a visualizable change or modification of the first and/or second protein assembly monomer in a protein assembly. In some embodiments, the visualizable change affects only the growing end of the protein assembly. In some embodiments, any of the methods provided herein further comprise the use of a third polynucleotide encoding an unmodified protein assembly monomer.

Various cellular events may be profiled in a cell using the methods described herein. In some embodiments, a single cellular event is profiled in a cell at a time. In some embodiments, the protein assemblies may be engineered such that multiple distinct cellular events may be profiled simultaneously. Any cellular even that can be connected to expression of a protein assembly monomer or a visualizable change or modification to a protein assembly monomer may be profiled using the methods described herein. For example, expression of one or more genes or proteins of interest within a cell may be profiled. In some embodiments, enzymatic activity (e.g., kinase activity, phosphatase activity, ubiquitylation, sumoylation, nitrosylation, glycosylation, lipidation, acylation, farnesylation, alkylation, amidation, carboxylation, hydroxylation, succinylation, sulfation, or any other post-translational modification mediated by an enzyme) may be profiled in a cell. Metabolic activity in a cell (e.g., the presence or absence of a metabolite of interest, or a change in concentration of a metabolite of interest), may also be profiled in a cell. In some embodiments, a change in concentration of an ion may be profiled in a cell. The change in concentration of an ion may be associated with a neurological event (e.g., transmission of a signal by the nervous system, or signals in any other electrically excitable cells such as muscle cells and cardiac cells). In some embodiments, a change in concentration of a small molecule, or the presence or absence of a small molecule (a signaling molecule (e.g., cGMP, cAMP, etc.), for example) may be profiled. In some embodiments, any process related to cell division, cell differentiation, or cell growth may be profiled. In certain embodiments, the cellular event comprises neuronal activity (e.g., transmission of a nerve signal).

Various protein assembly monomers may be used in the methods described herein. Any protein assembly monomer that can spontaneously assemble (i.e., self-assemble) in cells to form a protein assembly may be used in the methods provided in the present disclosure. Certain preferred but not necessarily required characteristics of a protein assembly monomer that is useful in the presently described methods include: the ability of the protein assembly monomer to be expressed in mammalian cells, the protein assembly monomer being unlikely to interfere with cellular physiology, and the ability of the monomers to bind to other molecules (e.g., accommodate decoration with fluorescent tags) without disrupting their structure, or the assembly of the monomers into an assembly. It is also preferrable that negligible monomer exchange is observed once the protein assembly monomers have been incorporated into the protein assembly, and that the protein assembly monomers assemble into a protein assembly at a slow rate. In some embodiments, monomer exchange once the monomer is incorporated into a protein assembly is negligible over about 1 day, about 2 days, about 3 days, about 4 days, or about 5 days. In some embodiments, monomer exchange is negligible over less than one day (e.g., 1 hour, 2 hours, 3 hours, 4 hours, 5 hours, 10 hours, 15 hours, or 20 hours). In some embodiments, the protein assembly monomers comprise endogenous microtubules. In some embodiments, the protein assembly monomers comprise bacterial R-bodies as described in Pond, F. R. et al. *Microbiol. Mol. Biol. Rev.* 53, 25-67 (1989), plant forisomes as described in Pelissier, H. C. et al. *Plant Cell Physiol.* 49, 1699-1710 (2008), amyloid fibrils as described in LeVine, H. et al. *Methods in Enzymology* 309, 274-284, prions as described in Barmada, S. J. et al. *J. Neurosci.* 25, 5824-5832 (2005), filamentous viruses as described in Shukla, S. et al. *Biomater. Sci.* 2, 784-797 (2014), crystals of the fluorescent protein XpA as described in Tsutsui, H. et al. *Mol. Cell* 58, 186-193 (2015), engineered fiber-forming peptides as described in Shen, H. et al. *Science* 362, 705-709, engineered lattice-forming peptides as described in Nguyen, T. K. et al. *ACS Appl. Nano Mater.* 4, 1672-1681 (2021), or polymers of SpyTag_peptide and SpyCatcher_protein as described in Zakeri, B. et al. *Proc. Natl. Acad. Sci.* 109, E690-E697 (2012) and Sun, F. et al. *Proc. Natl. Acad. Sci.* 111, 11269-11274 (2014). In some embodiments, the protein assembly monomers comprise crystals of the kinase PAK4. In certain embodiments, the protein assembly monomers comprise the catalytic domain of PAK4 fused to the PAK4 inhibitor Inka1 (also referred to herein as "iPAK4"). In some embodiments, the protein assemblies comprise protein fibers, two-dimensional nanosheets or discs, or microparticles.

Various promoters can be used to control expression of the protein assembly monomers used in the methods described herein. In some embodiments, the first and second promoters in the polynucleotides used in the methods provided herein are the same. In some embodiments, the first and the second promoters are different. Such promoters may generally be classified as "activity-dependent promoters" and "activity-independent promoters." In some embodiments, expression of one or more genes under control of an activity-dependent promoter is associated with an occurrence of a particular cellular event being profile. For example, expression of a gene under control of an activity-dependent promoter may be activated by the presence of a particular molecule, metabolite, or ion associated with a cellular event. In some embodiments, an inducer of the cellular event (e.g., a signaling molecule such as phorbol 12-myristate 13-acetate (PMA)), cyclic adenosine monophosphate (cAMP), cyclic guanosine monophosphate (cGMP), adenosine triphosphate (ATP), inositol triphosphate ($IP_3$), $Ca^{2+}$ ion, phosphatidylinositol 4,5-bisphosphate ($PIP_2$), diacylglycerol (DAG), nitric oxide (NO), carbon monoxide (CO), hydrogen sulfide ($H_2S$), steroid hormones, mitogen activated protein kinase (MAPK), or arachidonic acid. In some embodiments, a molecule produced as a result of the cellular event activates the second promoter. In some embodiments, the second promoter used in the polynucleotides of the methods described herein is an activity-dependent promoter. In certain embodiments, the activity-dependent promoter comprises an immediate early gene (IEG) promoter (e.g., cFos, ERK, npas4, arc, ZNF268 (also known as EGR-1), or JUN). Use of an activity-dependent promoter leads to the expression of a protein assembly monomer that includes some modification (e.g., fluorescent protein) that can be visualized, indicating that the cellular event occurred.

In contrast, expression of a gene under control of an activity-independent promoter is not associated with an occurrence of a particular cellular event. In some embodiments, an activity-independent promoter is a constitutive promoter. In some embodiments, the first promoter used in the polynucleotides of the methods described herein is an activity-independent promoter. In certain embodiments, a first polynucleotide expressing a protein assembly monomer under control of an activity-independent promoter and a second polynucleotide expressing a protein assembly monomer under control of an activity-dependent promoter are utilized in the methods provided herein.

One or more cellular events may be profiled in a single cell at a time, or in multiple cells simultaneously. The methods described herein may be used to profile cellular events in any cell type. In some embodiments, a bacterial cell or a mammalian cell are profiled. In certain embodiments, the cell is a human cell. In some embodiments, the cell is a neuron, a cardiac myocyte, a progenitor cell, or a stem cell. Any other cell type known in the art or disclosed herein may also be profiled using the methods described herein. In some embodiments, the first and second polynucleotide may be joined together, for example, to form a single expression vector (e.g., a bicistronic vector). In some embodiments, the transcripts produced by the first and the second polynucleotide joined together as a single expression vector are produced by alternative splicing of a single parent transcript driven by the same promoter.

Time Stamps

The methods of the present disclosure involve incorporating markers (e.g., colored bands, which may be fluorescent colored bands) into a slowly growing protein assembly in a cell, allowing protein assembly growth and particular segments of the assembly to be mapped and correlated to wall-clock time. Such incorporation of markers into the protein assembly allows the determination of particular times at which the one or more cellular events being profiled occur. In some embodiments, the time resolution for the methods described herein is on the order of minutes. In certain embodiments, the time resolution is on the order of seconds (e.g., approximately 20 seconds when using the optogenetic strategy described herein, for example). Various strategies may be used to keep track of time within the growing protein assemblies, including, but not limited to, dye-based methods and optogenetic methods. Any strategy that allows segments of the protein assembly to be distinguished from one another and correlated with time may be used in the methods described herein, which are not limited to the exemplary strategies for tracking time described here.

In some embodiments, dye-based strategies for tracking time in the protein assembly may be employed. For example, the protein assembly monomer encoded by the first polynucleotide utilized in the methods provided herein may be fused to a visualizable tag (e.g., any tag that can be modified at different time points during profiling of one or more cellular events). In some embodiments, the visualizable tag binds to a visualizable molecule (e.g., a dye, such as a fluorescent dye). In such instances, different fluorescent dyes can be provided to the cell being profiled at different times, such that each fluorescent dye is incorporated into the growing protein assembly, producing differently-colored bands that correlate with specific time periods of cell growth. In some embodiments, the visualizable tag comprises a peptide tag that binds fluorescent dyes, a small molecule tag that binds fluorescent dyes, a protein tag that binds fluorescent dyes, or a nucleic acid tag that binds fluorescent dyes. In certain embodiments, the visualizable tag comprises a peptide tag that binds fluorescent dyes. Such tags include, for example, HALOTAG®, SNAP-TAG®, and CLIP-TAG™. In some embodiments, the cell is incubated for a first period of time in the presence of a first fluorescent dye that binds to the visualizable tag. The cell may then be further incubated for a second period of time in the presence of a second fluorescent dye that binds to the visualizable tag. The first and/or second period of time may each independently be on the order of minutes (e.g., one minute, two minutes, three minutes, four minutes, five minutes, ten minutes, or more), hours (e.g., one hour, two hours, three hours, four hours, five hours, six hours, seven hours, eight hours, nine hours, ten hours, or more), or days (e.g., one day, two days, three days, four days, five days, or more). The fluorescent dye used in each period of time produces a colored band in the protein assembly, and the length of each colored band correlates linearly with time. The time at which a particular cellular event being profiled occurred can thus be interpolated from the relative location of some marker of the event (e.g., a visualizable protein such as GFP, or some other marker as discussed herein) between the start and the end of a particular colored band. In some embodiments, the fluorescent dyes are small molecule dyes. In certain embodiments, the fluorescent dyes are selected from the group consisting of ALEXA FLUOR® 488, $JF_{503}$, $JF_{525}$, $JF_{549}$, $JF_{552}$, $JF_{585}$, $JFX_{608}$, $JF_{646}$, and $JF_{669}$, each fused to a HALOTAG® ligand. In some embodiments, any of the methods provided herein may further comprise incubating the cell for one or more additional periods of time in the presence of an additional fluorescent dye, wherein the same fluorescent dye is not used in adjacent periods of time. Protein assemblies containing multiple colored bands may thus be produced in a cell and used to profile one or more cellular events over multiple time periods.

In some embodiments, optogenetic strategies for tracking time in the protein assembly may be employed in the methods provided in the present disclosure. Such an approach provides the advantages of not requiring the addition of exogeneous dyes during the cell culture process and of having a relatively short time resolution. In some embodiments employing an optogenetic strategy for tracking time in the protein assembly, the visualizable tag fused to the protein assembly monomer encoded by the first polynucleotide comprises a light-gated tagging system (e.g., a fluorescent protein that is only incorporated into the protein assembly after being released from a photocaging system). For example, a protein assembly monomer fused to a light-gated tag may only be incorporated into a growing protein assembly after being released by exposure to light of a particular wavelength. The light acts selectively on the protein assembly monomers in solution but does not release those that have already been incorporated into the protein assembly. In some embodiments, the cell is incubated for a first period of time in the absence of illumination that releases the visualizable tag. The cell may then be further incubated for a second period of time in the presence of illumination that releases the visualizable tag (i.e., illumination with light of a particular wavelength, which may vary depending on the light-gated tag used). Thus, incubating the cell in the presence of illumination that releases the visualizable tag produces a colored band in the protein assembly. Exemplary caging systems for use with the light-gated tags in the methods of the present disclosure include, but are not limited to, Dronpa, the Cry/CIB1 system, and Phocle, as described in Zhou, X. X., et al. *Science.* 338(6108), 810-814 (2012), Kennedy, M. J., et al. *Nat. Methods.* 7(12). 973-975 (2010), and Zhang, W., et al. *Nat. Methods.* 14(4), 391-394 (2017).

Visualizable Modifications to the Protein Assembly

As described herein, the methods of the present disclosure utilize protein assemblies engineered such that they undergo a visualizable change or modification during an occurrence of a cellular event of interest, or are only expressed during a cellular event of interest. The present disclosure contemplates the use of various exemplary strategies for linking visualizable changes or modifications to a protein assembly to an occurrence of a cellular event but is not limited to those strategies specifically disclosed herein. Any strategy that links an occurrence of a cellular event to a visualizable change in the protein assembly may be utilized in the methods described herein. In some embodiments, the visualizable change or modification of the first and/or second protein monomer in a protein assembly comprises binding of a dye to the protein monomer. In some embodiments, the visualizable change or modification of the first and/or second protein monomer in a protein assembly comprises post-translational modification of the protein monomer.

In some embodiments, the protein assembly monomer encoded by the second polynucleotide used in the methods described herein is fused to a visualizable protein. In such instances, activation of the second promoter on the second polynucleotide of the presently described methods may be associated with an occurrence of the cellular event being profiled (e.g., an activity-dependent promoter as described herein). In some embodiments, the visualizable protein comprises a fluorescent protein (e.g., CFP, GFP, eGFP, RFP, or YFP). In certain embodiments, the visualizable protein comprises eGFP.

In some embodiments, the cell in which a cellular event is being profiled may comprise one or more additional polynucleotides encoding a protein assembly monomer fused to a distinct visualizable protein under control of a distinct promoter (e.g., an activity-dependent promoter as described herein). Activation of the distinct promoter may be associated with an occurrence of a different cellular event, thereby allowing multiple cellular events to be profiled in the same cell simultaneously. For example, occurrences of one cellular event being profiled may be associated with modification of the protein assembly with GFP, while another cellular event being profiled may be associated with modification of the protein assembly with RFP. In such an example, both the GFP and RFP modifications to the protein assembly may be visualized and correlated with time using one of the strategies described herein (e.g., dye-based strategies or optogenetic strategies).

In some embodiments, any of the methods described herein may further comprise a step of imaging the protein assembly in the cell to determine the location of the protein assembly monomer fused to the visualizable protein relative to the locations of the first and the second fluorescent dyes bound to the visualizable tag, or the differently colored bands produced using the optogenetic methods described herein, thereby determining the times at which the cellular event occurs.

Another strategy for linking visualizable changes to the protein assembly to a cellular event being profiled is through the use of a visualizable tag (e.g., HALOTAG® ligand) that is susceptible to cleavage by a protease. In some embodiments, the cell being profiled further comprises a polynucleotide encoding a protease. In certain embodiments, the polynucleotide encoding a protease is under control of an activity-dependent promoter. The protease will thus only be expressed during an occurrence of a particular cellular event and will therefore cleave the visualizable tag from the protein assembly monomer only during an occurrence of the cellular event (e.g., during periods of elevated $Ca^{2+}$, concentration), rendering the visualizable tag nonfunctional and dark. Instances of the cellular event will thus produce dark spots on the protein assembly, where the visualizable tag has been cleaved from the protein assembly monomers prior to their incorporation into the assembly. In some embodiments, the polynucleotide encoding a protease is under control of an activity-independent promoter and is expressed constitutively. The protease may be active only under certain cellular conditions or during a particular cellular event. In some embodiments, the cellular event comprises an elevated $Ca^{2+}$ concentration (e.g., elevated calcium levels associated with a neurological signal). In certain embodiments, the protease is a $Ca^{2+}$-dependent protease (e.g., a calcium-dependent TEV protease). Any protease whose expression can be associated with an occurrence of a cellular event of interest may be used in such a strategy for modifying the protein assemblies described herein.

In some embodiments, the protein assembly monomer encoded by the second polynucleotide is fused to a visualizable protein, and the visualizable protein is visualizable only after being modified due to a cellular event (e.g., the visualizable protein can only be visualized following modification by an enzyme involved in a particular cellular event, such as a kinase). In some embodiments, the cellular event comprises enzyme activity. In some embodiments, the cellular event comprises a post-translational modification. In certain embodiments, the cellular event comprises kinase activity, phosphatase activity, ubiquitylation, sumoylation, nitrosylation, glycosylation, lipidation, acylation, farnesylation, alkylation, amidation, carboxylation, hydroxylation, succinylation, or sulfation. In certain embodiments, the cellular event comprises kinase activity. The visualizable protein utilized in such a strategy may comprise, for example, a fluorescence resonance energy transfer (FRET) sensor that senses the activity of a particular enzyme. In some embodiments, the visualizable protein comprises FRESCA, which senses calcium levels indirectly via the enzyme CaMKII. In some embodiments, the visualizable protein comprises ExRai-AKAR2, which senses cAMP levels indirectly via the activity of protein kinase A. In some embodiments, the visualizable protein comprises EKARet, which senses ERK activation.

An additional strategy for identifying occurrences of a cellular event involves the use of a binding moiety fused to the protein assembly monomer. In some embodiments, the protein assembly monomer encoded by the second polynucleotide is fused to a binding moiety, wherein the binding moiety binds a molecule associated with an occurrence of a cellular event being profiled (e.g., one or more cellular proteins that are only produced during the cellular event). In certain embodiment, the binding moiety comprises a nanobody. Thus, the presence and identity of the molecule bound to the binding moiety can be analyzed to determine whether a cellular event occurred. In some embodiments, analyzing the identity of the molecule bound to the binding moiety comprises labeling the target molecules with a fluorescently tagged antibody, or a variant or fragment thereof. In some embodiments, analyzing the identity of the molecule bound to the binding moiety comprises labeling the target molecule with a fluorescently tagged secondary nanobody.

The various strategies for recording time and for introducing visualizable modifications associated with a cellular event onto the protein assembly may be used alone, or they may be used in any combination with one another. Multiple cellular events may be profiled in a cell simultaneously, for example, by using two or more of the strategies for introducing visualizable modifications associated with a cellular event onto the protein assembly simultaneously. The dye-based methods and optogenetic strategies for recording time on the protein assembly described herein may also be used in combination with any of the strategies described herein for introducing visualizable modifications onto the protein assembly.

Thus, in some embodiments, the present disclosure provides methods for profiling a cellular event over time comprising:

a) incubating a cell, wherein the cell comprises:
  - a first polynucleotide encoding a protein assembly monomer fused to a visualizable tag under control of a first promoter; and
  - a second polynucleotide encoding a protein assembly monomer fused to a visualizable protein under control of a second promoter, wherein activation of the second promoter is associated with an occurrence of the cellular event being profiled;

for a period of time $t_1$ in the presence of a first fluorescent dye that binds to the visualizable tag, thereby allowing the protein assembly monomers expressed by the first and second polynucleotides to assemble into a protein assembly;

b) further incubating the cell for a period of time $t_2$ in the presence of a second fluorescent dye that binds to the visualizable tag, thereby allowing the protein assembly monomers expressed by the first and second polynucleotides to further assemble onto the protein assembly; and c) imaging the protein assembly.

In some embodiments, the protein assembly is imaged in the cell. In some embodiments, the protein assembly is imaged to determine the location of the protein assembly monomer fused to the visualizable protein relative to the locations of the first and the second fluorescent dyes bound to the visualizable tag, thereby determining the times at which the cellular event occurs.

In some embodiments, the methods further comprise incubating the cell prior to the step of imaging for one or more additional periods of time $t_x$ in the presence of a fluorescent dye, wherein the same fluorescent dye is not used in adjacent periods of time. In some embodiments, the cell comprises one or more additional polynucleotides encoding a protein assembly monomer fused to a distinct visualizable protein under control of a distinct promoter, wherein activation of the distinct promoter is associated with an occurrence of a different cellular event, thereby profiling multiple cellular events simultaneously.

In some embodiments, the present disclosure provides methods for profiling a cellular event over time comprising:

a) incubating a cell, wherein the cell comprises:
  - a first polynucleotide encoding a protein assembly monomer fused to a light-gated tag under control of a first promoter; and
  - a second polynucleotide encoding a protein assembly monomer fused to a visualizable protein under control of a second promoter, wherein activation of the second promoter is associated with an occurrence of the cellular event being profiled;

for a period of time $t_1$ in the absence of illumination that releases the light-gated tag, thereby allowing the protein assembly monomers to assemble into a protein assembly;

b) further incubating the cell for a period of time $t_2$ in the presence of illumination that releases the light-gated tag, thereby allowing the protein assembly monomers to further assemble onto the protein assembly; and c) imaging the protein assembly.

In some embodiments, the protein assembly is imaged in the cell. In some embodiments, the protein assembly is imaged to determine the location of the protein assembly monomer fused to the visualizable protein relative to the locations of the released light-gated tags, thereby determining the times at which the cellular event occurs. In some embodiments, the light-gated tags are only released when the protein assembly monomers in solution are exposed to light of a particular wavelength.

The light-gated tag may comprise any light-gated fluorescent protein as described herein. In some embodiments, incubating the cell in the presence of illumination that releases the light-gated tag produces a colored band in the protein assembly.

In some embodiments, the present disclosure provides methods for profiling a cellular event over time comprising:

a) incubating a cell, wherein the cell comprises:
    - a first polynucleotide encoding a protein assembly monomer fused to a visualizable tag susceptible to protease cleavage under control of a first promoter; and
    - a second polynucleotide encoding a protease under control of a second promoter, wherein the protease cleaves the visualizable tag from the protein assembly monomer during an occurrence of the cellular event;

for a period of time $t_1$ in the presence of a first fluorescent dye that binds to the visualizable tag, thereby allowing the protein assembly monomers expressed by the first and second polynucleotides to assemble into a protein assembly;

b) further incubating the cell for a period of time $t_2$ in the presence of a second fluorescent dye that binds to the visualizable tag, thereby allowing the protein assembly monomers expressed by the first and second polynucleotides to further assemble onto the protein assembly; and c) imaging the protein assembly.

In some embodiments, the protein assembly is imaged in the cell. In some embodiments, the protein assembly is imaged to determine the location of the protein assembly monomers cleaved by the protease relative to the locations of the first and the second fluorescent dyes bound to the visualizable tag, thereby determining the times at which the cellular event occurs.

In some embodiments, the cellular event comprises elevated $Ca^{2+}$ concentration. In certain embodiments, the protease is a $Ca^{2+}$-dependent TEV protease.

In some embodiments, the present disclosure provides methods for profiling a cellular event over time comprising:

a) incubating a cell, wherein the cell comprises:
    - a first polynucleotide encoding a protein assembly monomer fused to a visualizable tag under control of a first promoter; and
    - a second polynucleotide encoding a protein assembly monomer fused to a visualizable protein under control of a second promoter, wherein the visualizable protein is visualizable only after being modified due to a cellular event;

for a period of time $t_1$ in the presence of a first fluorescent dye that binds to the visualizable tag, thereby allowing the protein assembly monomers expressed by the first and second polynucleotides to assemble into a protein assembly;

b) further incubating the cell for a period of time $t_2$ in the presence of a second fluorescent dye that binds to the visualizable tag, thereby allowing the protein assembly monomers expressed by the first and second polynucleotides to further assemble onto the protein assembly; and c) imaging the protein assembly.

In some embodiments, the protein assembly is imaged in the cell. In some embodiments, the protein assembly is imaged to determine the location of the protein assembly monomer fused to the visualizable protein relative to the locations of the first and the second fluorescent dyes bound to the visualizable tag, thereby determining the times at which the cellular event occurs.

In some embodiments, the cellular event comprises enzyme activity (e.g., the activity of an enzyme mediating a particular post-translation modification). In certain embodiments, the cellular event comprises kinase activity, phosphatase activity, ubiquitylation, sumoylation, nitrosylation, glycosylation, lipidation, acylation, farnesylation, alkylation, amidation, carboxylation, hydroxylation, succinylation, or sulfation. In certain embodiments, the cellular event comprises kinase activity. In some embodiments, the visualizable protein comprises a FRET sensor. In certain embodiments, the visualizable protein comprises FRESCA, ExRai-AKAR2, or EKARet.

In some embodiments, the present disclosure provides methods for profiling a cellular event over time comprising:

a) incubating a cell, wherein the cell comprises:
    - a first polynucleotide encoding a protein assembly monomer fused to a visualizable tag under control of a first promoter; and
    - a second polynucleotide encoding a protein assembly monomer fused to a binding moiety under control of a second promoter, wherein the binding moiety binds a molecule associated with an occurrence of a cellular event being profiled;

for a period of time $t_1$ in the presence of a first fluorescent dye that binds to the visualizable tag, thereby allowing the protein assembly monomers expressed by the first and second polynucleotides to assemble into a protein assembly;

b) further incubating the cell for a period of time $t_2$ in the presence of a second fluorescent dye that binds to the visualizable tag, thereby allowing the protein assembly monomers expressed by the first and second polynucleotides to further assemble onto the protein assembly; and c) analyzing the identity of the molecule bound to the binding moiety to determine whether the cellular event occurred.

In some embodiments, the binding moiety comprises a nanobody. In some embodiments, the molecule associated with an occurrence of the cellular event being profiled comprises one or more cellular proteins. In some embodiments, analyzing the identity of the molecule bound to the binding moiety comprises labeling the target molecules with a fluorescently tagged antibody, or a variant or fragment thereof. In some embodiments, analyzing the identity of the molecule bound to the binding moiety comprises labeling the target molecule with a fluorescently tagged secondary nanobody.

Methods for Profiling the Effect of a Stimulus on a Cellular Event Over Time

Any of the methods described herein for profiling cellular events in a cell over time may be used for profiling the effect of a stimulus (e.g., a candidate therapeutic agent, or some other stimulus, such as light, heat, or an electrical impulse) on a cell. For example, a cell may be incubated as in the methods described herein, wherein the cell is being treated with or has previously been treated with a stimulus. The methods described herein may be used to determine whether a particular cellular event occurs in the presence of the stimulus, and at what times, and the profile of the cellular event for the cell that was treated with the stimulus can be compared to such a profile in a cell that was not treated with the stimulus. If a difference in the profile of the cellular event in the treated cell compared to the cell that was not treated is observed, this may indicate that the stimulus modulates the cellular event of interest (or multiple cellular events of interest).

Thus, in some embodiments, the present disclosure provides methods for profiling the effect of a stimulus on a cellular event over time comprising:

a) incubating a cell for a period of time that is being treated with or has been treated with a stimulus, wherein the cell comprises:
   - a first polynucleotide encoding a first protein assembly monomer under control of a first promoter;
   - a second polynucleotide encoding a second protein assembly monomer under control of a second promoter;

wherein a cellular event leads to expression of the first and/or second protein monomer or a visualizable change or modification of the first and/or second protein monomer in a protein assembly; and wherein a difference in the profile of the cellular event over time in the cell treated with the stimulus relative to a cell not treated with the stimulus indicates that the stimulus modulates the cellular event.

Any stimulus may be profiled using the methods described herein. In some embodiments, the stimulus comprises light. In some embodiments, the stimulus comprises an electrical impulse. In some embodiments, the stimulus comprises a mechanical stimulus. The stimulus may also comprise treatment with an agent (e.g., a therapeutic agent, or a candidate therapeutic agent). In some embodiments, the agent comprises a drug candidate, or a known drug. The agent may comprise a small molecule, a protein, a peptide, or a nucleic acid therapeutic. The effect of an agent or other stimulus on any cellular event may be profiled using the methods disclosed herein. In some embodiments, the cellular event comprises gene expression, protein expression, enzymatic activity, metabolic activity, a change in the concentration of an ion, a change in the concentration of a small molecule, the presence of a metabolite, exposure to light cell differentiation, cell growth, or cell division.

Proteins, Polynucleotides, Cells, and Systems

In another aspect, the present disclosure provides proteins (e.g., any of the protein assembly monomers or assembled protein assemblies as described herein). In some embodiments, the proteins are fused to any of the visualizable tags, visualizable proteins, or other fusion partners as described herein.

The present disclosure also provides polynucleotides and pairs or polynucleotides for use in the methods described herein. In some embodiments, the polynucleotides comprise vectors for expressing one or more genes (e.g., viral vectors such as lentiviral vectors, etc.). Any expression vector that is known in the art may be utilized in the polynucleotides of the present disclosure if it can be engineered to express a protein assembly monomer. In one aspect, the present disclosure provides pairs of polynucleotides comprising: a first polynucleotide encoding a first protein assembly monomer under control of a first promoter; and a second polynucleotide encoding a second protein assembly monomer under control of a second promoter. In another aspect, the present disclosure provides pairs of polynucleotides comprising: a first polynucleotide encoding a protein assembly monomer fused to a visualizable tag under control of a first promoter; and a second polynucleotide encoding a protein assembly monomer fused to a visualizable protein under control of a second promoter. In another aspect, the present disclosure provides pairs of polynucleotides comprising: a first polynucleotide encoding a protein assembly monomer fused to a light-gated tag under control of a first promoter; and a second polynucleotide encoding a protein assembly monomer fused to a visualizable protein under control of a second promoter. In another aspect, the present disclosure provides pairs of polynucleotides comprising: a first polynucleotide encoding a protein assembly monomer fused to a visualizable tag susceptible to protease cleavage under control of a first promoter; and a second polynucleotide encoding a protease under control of a second promoter. In another aspect, the present disclosure provides pairs of polynucleotides comprising: a first polynucleotide encoding a protein assembly monomer fused to a visualizable tag under control of a first promoter; and a second polynucleotide encoding a protein assembly monomer fused to a binding moiety under control of a second promoter. In some embodiments, the polynucleotide comprises an expression vector (e.g., a plasmid). In some embodiments, the vector is a viral vector. In some embodiments, the vector is a lentiviral vector. In certain embodiments, the vector comprises cFos, ERK, npas4, arc, ZNF268 (also known as EGR-1), or JUN.

The various components of the polynucleotides provided herein (e.g., the promoters, protein assembly monomers, visualizable tags, visualizable proteins, etc.) are described herein. Any of the examples provided herein for each of these components may be used in any of the polynucleotides provided by the present disclosure. In some embodiments, the first and second polynucleotide may be joined together, for example, to form a single expression vector (e.g., a bicistronic vector). In some embodiments, the transcripts produced by the first and the second polynucleotide joined together as a single expression vector are produced by alternative splicing of a single parent transcript driven by the same promoter.

In some aspects, the present disclosure provides cells comprising any of the polynucleotides described herein. In some embodiments, the cells comprise multiple pairs of the polynucleotides described herein (e.g., for use in methods to profile multiple cellular events simultaneously using multiple strategies for introducing visualizable changes into the protein assembly monomers as described herein).

In some aspects, the present disclosure provides systems for profiling one or more cellular events over time in a cell. Such systems may comprise any of the polynucleotides or pairs of polynucleotides provided herein. In some embodiments, the system further comprises a microscope. In certain embodiments, the system further comprises a computer. In certain embodiments, the system further comprises a source of illumination (i.e., a light source). In some embodiments, the system further comprises software.

In certain embodiments, the polynucleotides express a protein comprising one or more of the following amino acid sequences:

```
iPAK4:
                                    (SEQ ID NO: 1)
MDYKDDDDKSGSEAEDWTAALLNRGRSRQPLVLGD

NCFADLVHNWMELPEEFPAAPAVPGPPGPRSPQRE

PQRVSHEQFRAALQLVVDPGDPRSYLDNFIKIGEG

STGIVCIATVRSSGKLVAVKKMDLRKQQRRELLFN
```

-continued

```
EVVIMRDYQHENVVEMYNSYLVGDELWVVMEFLEG

GALTDIVTHTRMNEEQIAAVCLAVLQALSVLHAQG

VIHRDIKSDSILLTHDGRVKLSDFGFCAQVSKEVP

RRKSLVGTPYWMAPELISRLPYGPEVDIWSLGIMV

IEMVDGEPPYFNEPPLKAMKMIRDNLPPRLKNLHK

VSPSLKGFLDRLLVRDPAQRATAAELLKHPFLAKA

GPPASIVPLMRQNRTR
```

HaloTag-iPAK4:

(SEQ ID NO: 2)

```
MIGTGFPFDPHYVEVLGERMHYVDVGPRDGTPVLF

LHGNPTSSYVWRNIIPHVAPTHRCIAPDLIGMGKS

DKPDLGYFFDDHVRFMDAFIEALGLEEVVLVIHDW

GSALGFHWAKRNPERVKGIAFMEFIRPIPTWDEWP

EFARETFQAFRTTDVGRKLIIDQNVFIEGTLPMGV

VRPLTEVEMDHYREPFLNPVDREPLWRFPNELPIA

GEPANIVALVEEYMDWLHQSPVPKLLFWGTPGVLI

PPAEAARLAKSLPNCKAVDIGPGLNLLQEDNPDLI

GSEIARWLSTLEISGEPTTSGSEAEDWTAALLNRG

RSRQPLVLGDNCFADLVHNWMELPEEFPAAPAVPG

PPGPRSPQREPQRVSHEQFRAALQLVVDPGDPRSY

LDNFIKIGEGSTGIVCIATVRSSGKLVAVKKMDLR

KQQRRELLFNEVVIMRDYQHENVVEMYNSYLVGDE

LWVVMEFLEGGALTDIVTHTRMNEEQIAAVCLAVL

QALSVLHAQGVIHRDIKSDSILLTHDGRVKLSDFG

FCAQVSKEVPRRKSLVGTPYWMAPELISRLPYGPE

VDIWSLGIMVIEMVDGEPPYFNEPPLKAMKMIRDN

LPPRLKNLHKVSPSLKGFLDRLLVRDPAQRATAAE

LLKHPFLAKAGPPASIVPLMRQNRTR
```

GFPJPAK4:

(SEQ ID NO: 3)

```
MSKGEELFTGVVPILVELDGDVNGYKFSVSGEGEG

DATYGKLTLKFICTTGKLPVPWPTLVTTLTYGVQC

FSRYPDHMKRHDFFKSAMPEGYVQERTIFFKDDGN

YKTRAEVKFEGDTLVNRIELKGIDFKEDGNILGHK

LEYNYNSHNVYIMADKQKNGIKANFKTRHNIEDGG

VQLADHYQQNTPIGDDPVLLPDNHYLSTQSALSKD

PNEKRDHMVILEFVTAAGITHGMDELYKSGGSEAE

DWTAALLNRGRSRQPLVLGDNCFADLVHNWMELPE

EFPAAPAVPGPPGPRSPQREPQRVSHEQFRAALQL

VVDPGDPRSYLDNFIKIGEGSTGIVCIATVRSSGK

LVAVKKMDLRKQQRRELLFNEVVIMRDYQHENVVE

MYNSYLVGDELWVVMEFLEGGALTDIVTHTRMNEE

QIAAVCLAVLQALSVLHAQGVIHRDIKSDSILLTH
```

-continued

```
DGRVKLSDFGFCAQVSKEVPRRKSLVGTPYWMAPE

LISRLPYGPEVDIWSLGIMVIEMVDGEPPYFNEPP

LKAMKMIRDNLPPRLKNLHKVSPSLKGFLDRLLVR

DPAQRATAAELLKHPFLAKAGPPASIVPLMRQNRT

R
```

Kits

Also provided by the present disclosure are kits. In one aspect, the kits provided may comprise one or more of the polynucleotides described herein. In some embodiments, the kits comprise any of the pairs of polynucleotides described herein, or multiple pairs of the polynucleotides described herein (e.g., for profiling multiple cellular events in a cell simultaneously). In some embodiments, the kits may further comprise a container (e.g., a vial, ampule, bottle, and/or dispenser package, or other suitable container). The kits may also comprise cells, including cells comprising any of the polynucleotides described herein, for use in the methods described herein. In some embodiments, the kits may further comprise other reagents for performing the methods disclosed herein (e.g., reagents for performing cell culture, reagents for transfecting, transducing, electroporating, or injecting a cell with the provided polynucleotides, fluorescent dyes, etc.). In some embodiments, the kits are useful for profiling one or more cellular events in a cell over time. In some embodiments, the kits are additionally useful for profiling the effect of a stimulus on a cellular event over time as described herein. In certain embodiments, a kit described herein further includes instructions for using the kit.

EXAMPLES

Example 1: Time-Tagged Ticker Tapes for Intracellular Recordings

Introduction

Reporter genes or antibody labels can report brain-wide patterns of IEG activation, but typically at only one[1,2] or at most two[3] time-points. Time-lapse in vivo microscopy can report longitudinal IEG dynamics,[4] but only in a small optically accessible region. Theoretical analyses have explored the possibility of encoding brain-wide dynamics in DNA or RNA sequences,[5,6] but despite progress[7] such ideas have not yet been realized.

Natural histories are written in the patterns of tooth enamel, the structures of pearls, and the thickness of tree rings. Inspired by these natural phenomena, cellular histories were encoded in protein microcrystals within individual cells. Protein assemblies can last for months or years and offer a wide array of functionalities that could serve as the basis for recording schemes.

Figure 1B:
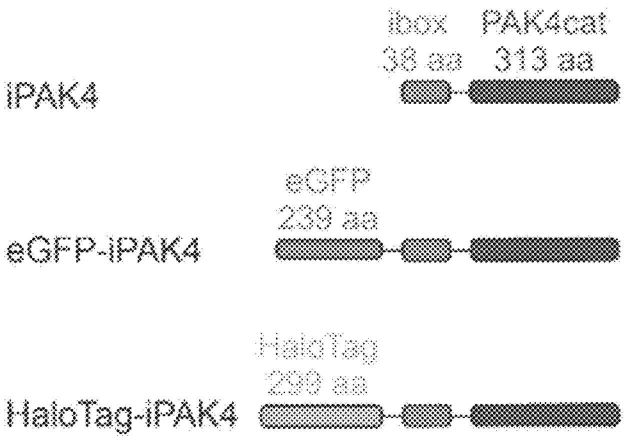

A protein-based recording scheme may have three elements (FIGS. 1A-1B). First, it may have a protein scaffold that grows with time and that can incorporate fluorescent markers. Second, it may have a means to impart fiducial timestamps to relate scaffold growth (which will likely vary between cells and over time) to timing of events in the outside world. By marking known timepoints on the assembly, one can correct for inevitable variations in growth rate over time and between cells, to enable high absolute timing accuracy on a cell-by-cell basis. Third, the recording scheme may have a fluorescent reporter of cellular (e.g., transcriptional) activity that can be stably incorporated into the scaffold.

For the protein scaffold, the selection criteria used in this Example were that it should: express in mammalian cells, assemble into a growing structure from a single polypeptide, have a known crystal structure, be unlikely to interfere with cellular physiology, and accommodate decoration with a fluorescent tag without disrupting the structure of the assembly. Many possibilities were considered, including endogenous microtubules, bacterial R-bodies,[8] plant forisomes,[9] amyloid fibrils,[10] prions,[11] filamentous viruses,[12] crystals of the fluorescent protein XpA,[13] engineered fiber-forming peptides,[14] and other proteins that spontaneously assemble in cells.[15]

Figure 1C:
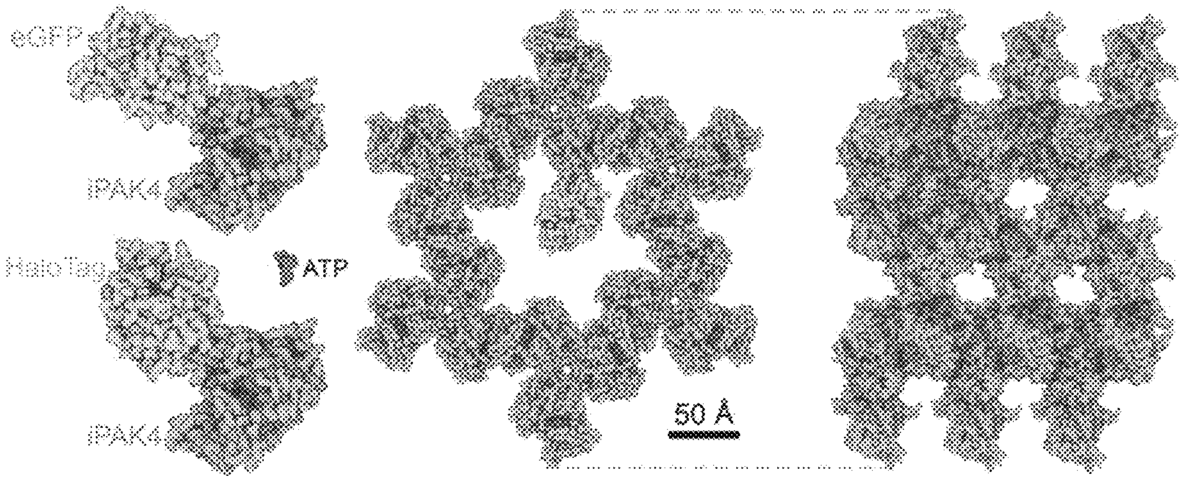

A fusion of the catalytic domain of the Pak4 kinase and the 38 amino acid iBox domain of its inhibitor Inka1 (hereafter called iPAK4) largely satisfied the selection criteria. This construct has been shown to stably assemble in cells into rod-shaped crystals.[16] The crystal structure has a hexagonal array of internal pores large enough to accommodate eGFP or a HALOTAG® ligand, suggesting the possibility of linear encoding of information via patterned fluorescence (FIG. 1C).

A fusion of the HALOTAG® ligand (HT) to iPAK4 was used to provide fiducial timestamps. It was reasoned that washes with different colored HT-ligand dyes could create color boundaries whose positions would correspond to known times. Even though HT dye washout in vivo occurs over hours, HT dye injection and labeling have fast onset (<10 minutes in vivo),[17] permitting precise demarcation of timestamps by the location of a color transition. A broad palette of bright, photostable, and brain-penetrant JaneliaFluor HALOTAG® ligand dyes are available, permitting diverse spectral encodings of fiducial timestamps.[18-20]

The activity reporter may store a stable mark of cellular activity or physiology upon incorporation into the growing assembly. Here the focus is on markers of transcriptional activation, though other modalities are conceivable. First, the kinetics of activation of a synthetic drug-inducible promoter, the Tet-ON system, were mapped. Then, the dynamics of an activity-responsive immediate early gene (IEG) were mapped in cultured neurons. IEG reporters are a powerful tool for identifying the brain regions and neuronal subtypes activated in a particular context.[21] For example, the IEG cFos has been used to map neurons activated during feeding,[22] sleep,[23] parenting,[24] aggression[25], and memory encoding.[26] IEG activity is also used to identify the neurons recruited into the physical embodiment of a memory trace, or engram. IEG activation is a good target for a ticker-tape recording because the relevant dynamics are often broadly distributed throughout the brain.[26] Motivated by potential applications toward brain-wide activity mapping, the cFos promoter was used to drive expression of eGFP-iPAK4 and thereby record time-series of cFos activity.

A related protein-based recording technique has been described, termed expression recording islands (XRIs).[27] The primary conceptual difference between XRIs and the time-tagged ticker tapes described herein is that the HALOTAG® ligand-based time-stamps give the ticker tapes described herein an absolute time-base in each single cell. This is not accomplished with XRIs.

Results iPAK4 Assemblies Grow Linearly in HEK Cells

Figure 1D:
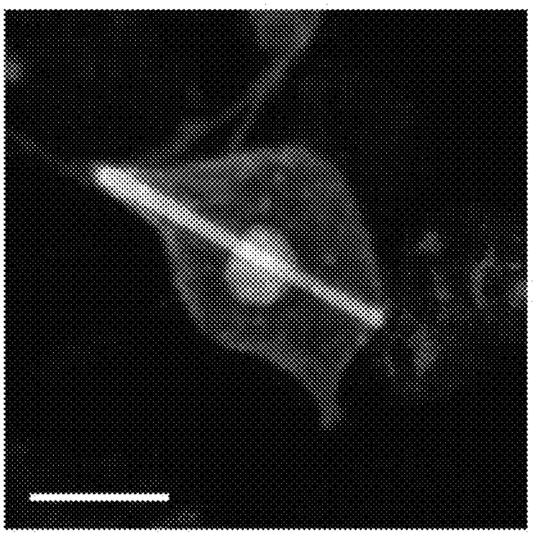
Figure 6A:
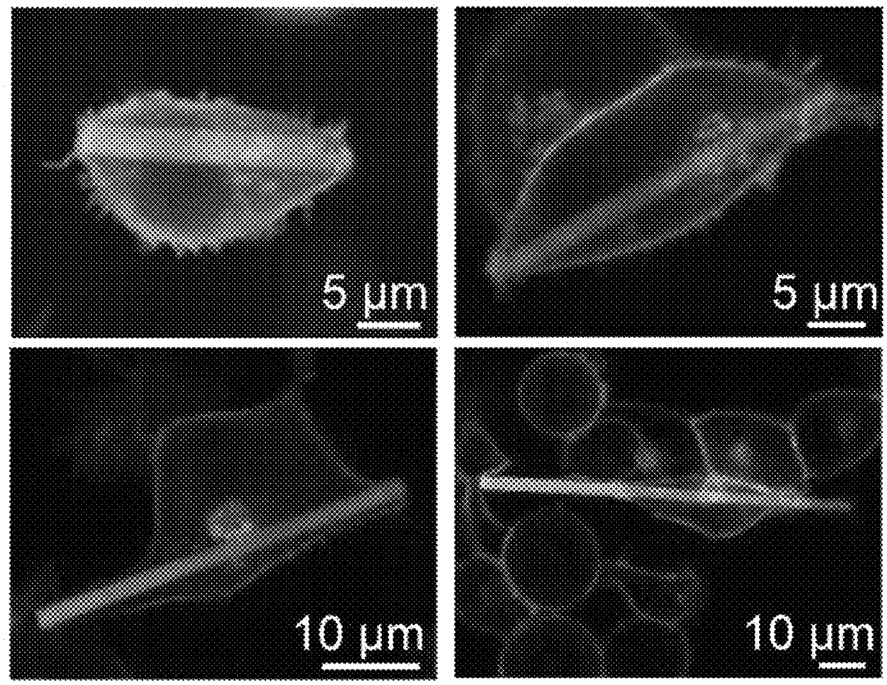
FIGS. 6A-6B show iPAK4 assembly morphology, nucleation, and growth.

In HEK cells co-transfected with CMV::iPAK4 (95%) and CMV::HT-iPAK4 (5%), assemblies began to grow 14-20 h after transfection. Incubation with a HT dye made the assemblies brightly fluorescent (FIGS. 1D and 6A). Most assembly-containing cells had only one assembly (288 of 333 cells, 86%). When the assemblies grew longer than the cell diameter, the membrane deformed, forming a sheath around the assembly, though this did not appear to impair either assembly growth or cell viability (FIG. 6A).

Figure 1E:
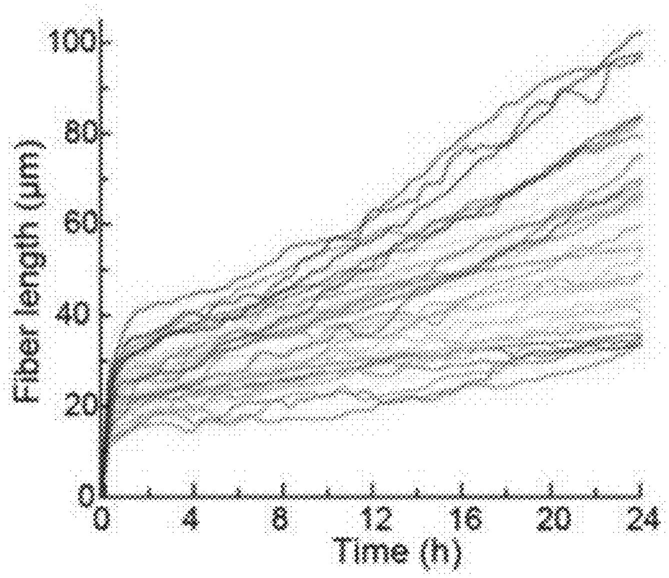
Figure 1F:
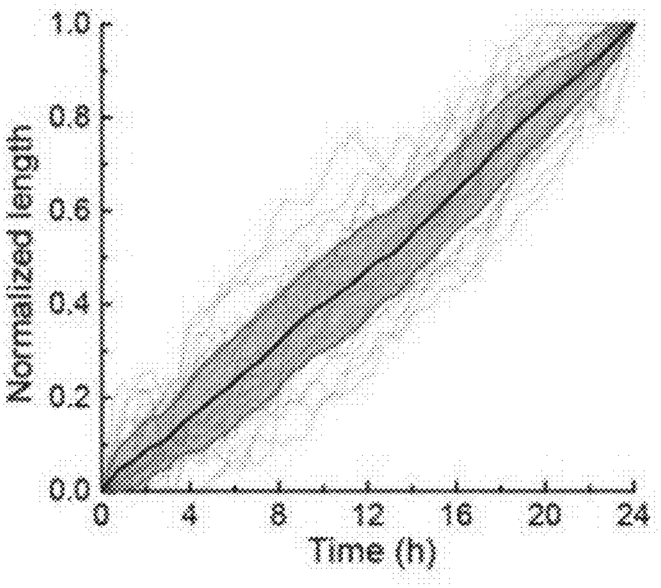
Figure 6B:
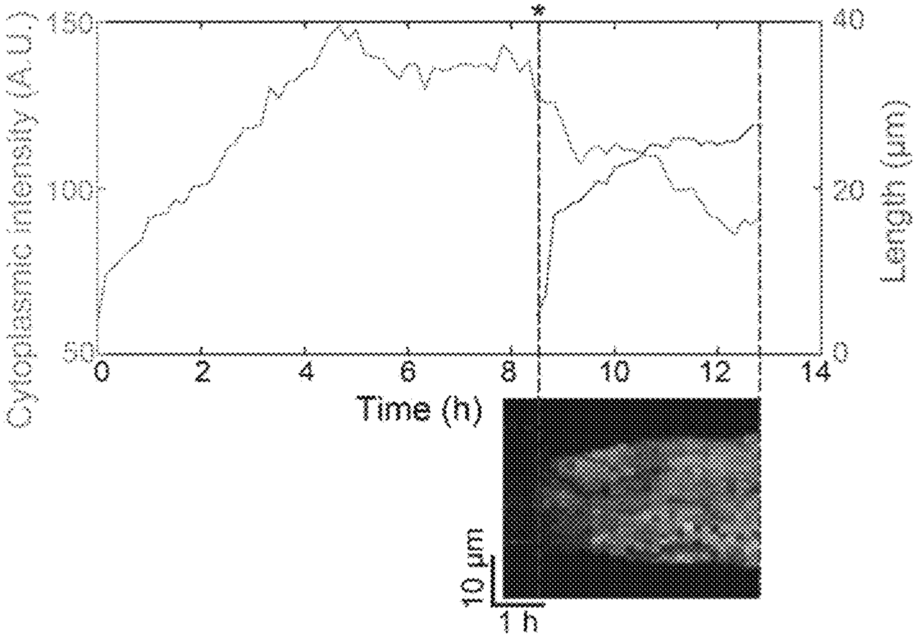

To assess the suitability of iPAK4 assemblies as a recording medium, a detailed characterization of their nucleation and growth was performed. CMV::iPAK4 (90%), CMV::eGFP-iPAK4 (5%), and CMV::HT-iPAK4 (5%) were co-expressed in HEK cells using lentiviral transduction, and $JF_{669}$ was added to the medium to label the HT. Time-lapse video microscopy was recorded over a 13 hour interval starting 1 hour after transfection, and over 43 hours starting 20 hours after transfection. The fluorescence of the cytoplasm and the growth of individual assemblies was then tracked. Initially, green (eGFP) and red (HT-$JF_{669}$) fluorescence accumulated in the cytoplasm. Upon nucleation, assemblies grew quickly (~0.5 μm/min) at first, while the cytoplasmic fluorescence dropped. This phase typically lasted approximately 1 h. The assemblies then transitioned to slower linear growth (FIG. 1E). While there was substantial cell-to-cell variability in the rate of linear growth, the population-average growth rate did not change over 24 hours after nucleation (FIG. 1F). A simple mass-action kinetic model predicted the two-phase growth profiles and quantitatively reproduced the observed growth profiles (Calculation 1, FIGS. 7A-7E). Assembly growth then slowed to a constant rate of 1-2 m/h, suggesting a balance of protein translation and assembly growth (FIG. 6B).

Figure 1G:
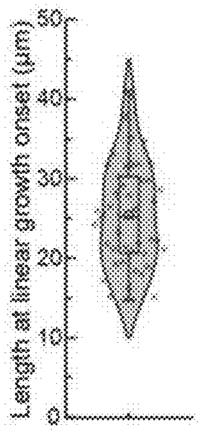
Figure 1H:
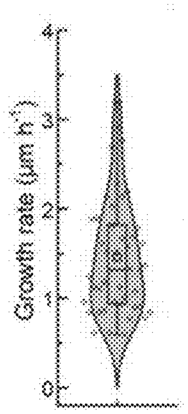
Figure 1I:
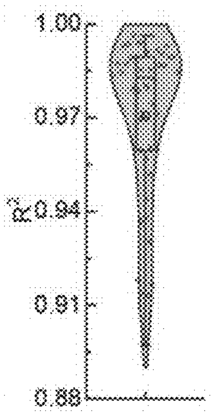

The distribution of assembly growth parameters across the population was quantified. The length of assemblies at the end of the nucleation phase was 26±7 μm (mean±s.d., n=46 assemblies, FIG. 1G). During the linear growth phase, the growth rate was 1.46±0.64 μm/h (mean±s.d., FIG. 1H). Within each cell, the assembly growth rate remained remarkably constant during the linear growth phase. For 24 hours, the fits of the growth profiles to straight lines yielded a population average $R^2$=0.97±0.02 (mean±s.d., FIG. 1*i*). Of the cells that had any assemblies, most contained only one (of 333 assembly-containing cells, 288 (86%) contained only one assembly). The rarity of multiple assemblies per cell was ascribed to the fact that a single growing assembly maintained the soluble iPAK4 concentration below the nucleation threshold. Multi-assembly cells seemed to arise from cells where an assembly broke, leading to two nuclei for growth of two separate assemblies.

Within the population, cell-to-cell variations in the intensities of the eGFP and HT fluorescence signals were observed, presumably due to variations in gene dosage. No correlation between the growth rates and these fluorescence levels was observed, indicating that at the low mole-fractions of fluorescent tags used here (approximately 5% for each fluorescent tag), the fluorescent tags did not affect the growth rate (FIGS. 8A-8D).

It was then determined whether the iPAK4 assemblies affect cell survival, as the assemblies often grew longer than the cell diameters (FIG. 6A). In a live-dead assay, no difference in survival between HEK cells expressing iPAK4 assemblies and control untransfected HEK cells was observed (iPAK4$^{(+)}$: 0.267±0.139% dead cells, n=24 fields of view comprising 89,341 cells; iPAK4$^{(-)}$: 0.262±0.107% dead cells, n=24 fields of view comprising 94,202 cells. P=0.90, student's t-test. FIGS. 9A-9D). Though the stiff assemblies deforming the cell membranes looked unusual, simple geometrical estimates showed that the assemblies perturbed HEK cell surface area by <15% and volume by <2%; and the predicted fractional perturbations for neurons were even smaller (Calculation 2).

It was then tested whether cells containing iPAK4 assemblies could divide. In taking time-lapse movies of HEK cells labeled with Hoechst 33342 nuclear stain, occasional cell divisions were observed. The formation of mitotic chromosomes and the process of cell division appeared qualitatively similar in cells with iPAK4 assemblies, in cells expressing iPAK4 but without assemblies, and in non-expressing cells (FIGS. 10A-10D). The number of mitotic events captured was n=8 divisions in cells containing assemblies. It is noted that for applications in neurons, cell division is not a concern. Together, these results established that iPAK4 assembly growth during the linear growth phase formed a suitable substrate for cellular recordings, provided cell-to-cell variations in growth rate are corrected for.

HALOTAG® Ligand Time-Stamps Enable Accurate Timing in iPAK4 Assemblies

Figure 2A:
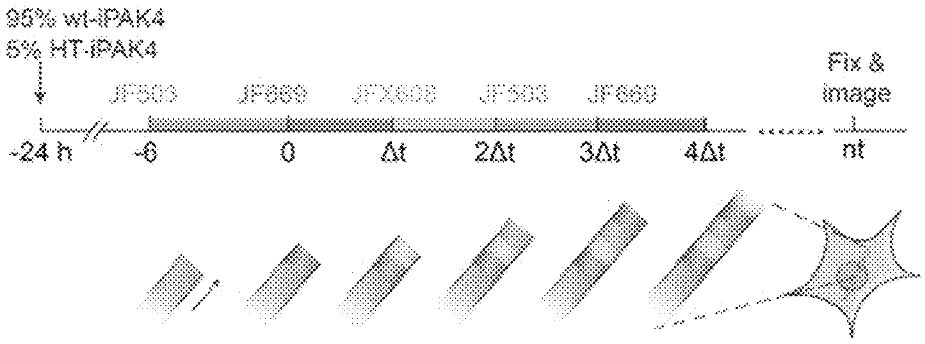
FIGS. 2A-2G show that iPAK4 assemblies can be sequentially labeled with different dyes.
Figure 2B:
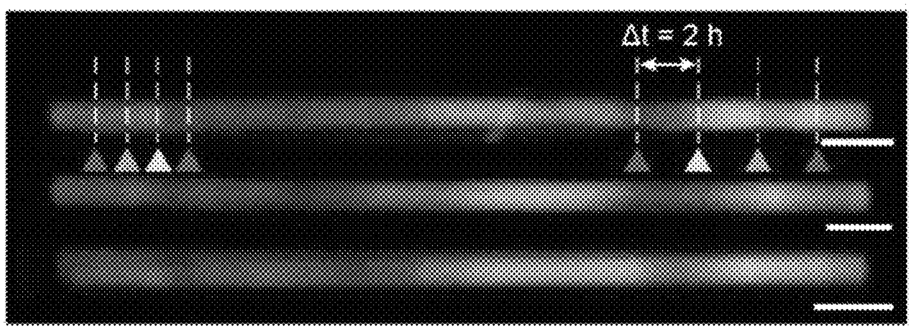
Figure 11A:
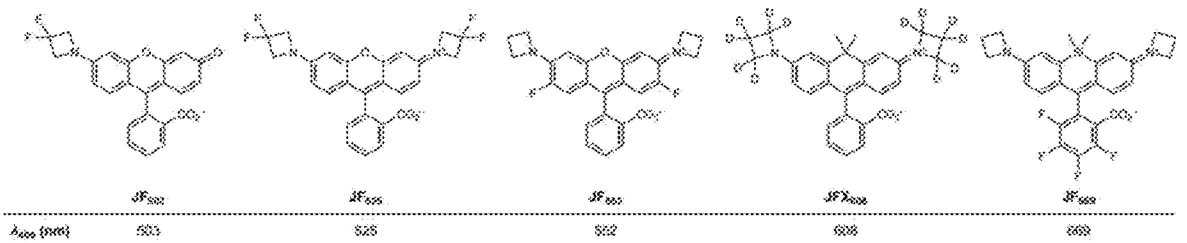
FIGS. 11A-11B show JaneliaFluor HALOTAG® ligand dyes used in the work described herein. Related to FIG. 2.
Figure 11B:
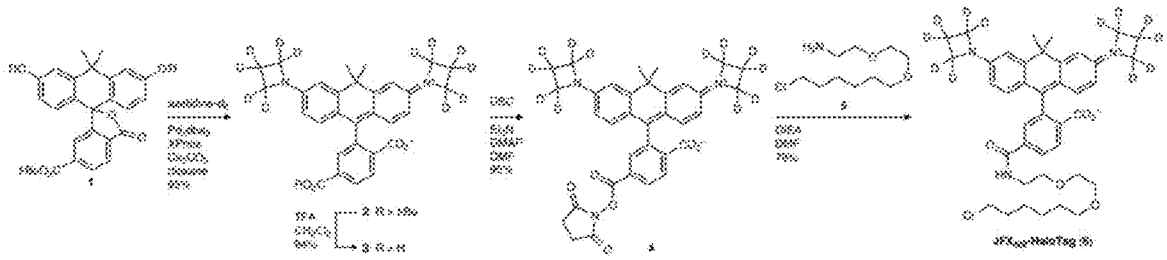

To test whether assemblies could encode HT dye time-stamps, HEK cells growing HT-iPAK4 assemblies were successively washed with different colors of HT-ligand dyes at Δt=2 h intervals in the sequence $JF_{503}$, $JF_{669}$, $JFX_{608}$, $JF_{503}$, $JF_{669}$ (FIG. 2A; see FIGS. 11A-11B for dye structures, photophysical properties, and synthesis of $JFX_{608}$). The cells were then fixed and imaged with spectrally resolved confocal microscopy. Clear progression of colored bands matching the sequence of dye additions was observed. The bands followed mirror-image patterns on opposite sides of the assemblies, indicating that the assemblies grew from both ends (FIGS. 2B, 6A-6B, 12A-12B).

Figure 12A:
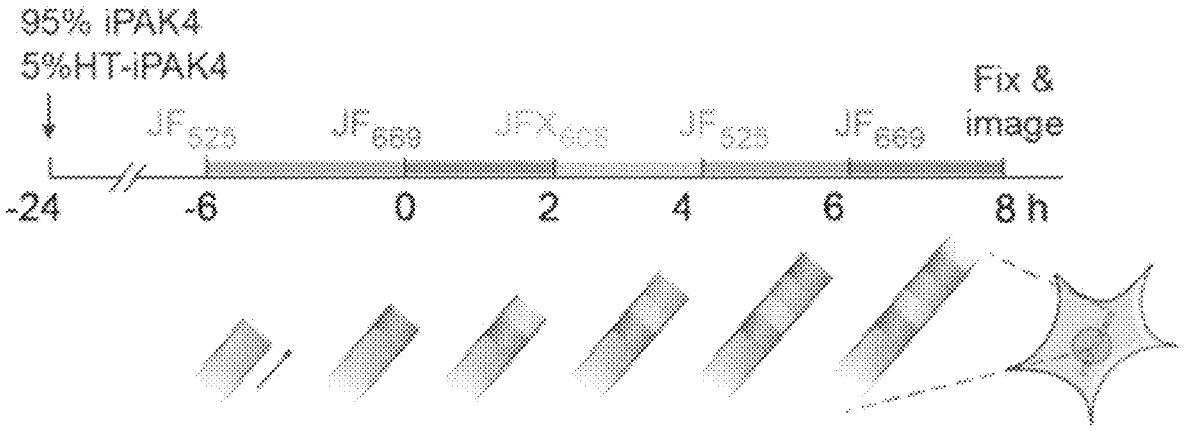
FIGS. 12A-12E show color stripes in sequentially labeled HT-iPAK4 assemblies in HEK293T cells. Related to FIG. 2, FIG. 12A provides a scheme for labeling of intracellular iPAK4 assemblies labeled with four dye transitions on each end. HEK293T cells were co-transfected with CMV::iPAK4 (95%) and CMV::HT-iPAK4 (5%). After the onset of assembly growth, cells were washed at Δt=2 h intervals in the sequence $JF_{525}$, $JF_{669}$, $JFX_{608}$, $JF_{503}$, $JF_{669}$.
Figure 12B:
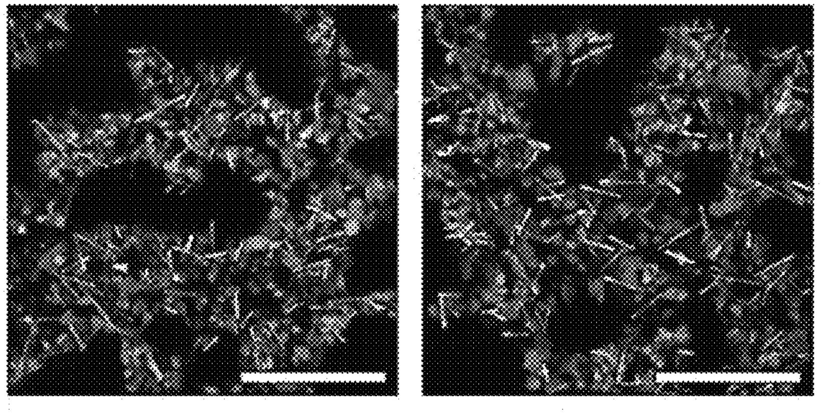
Figure 12C:
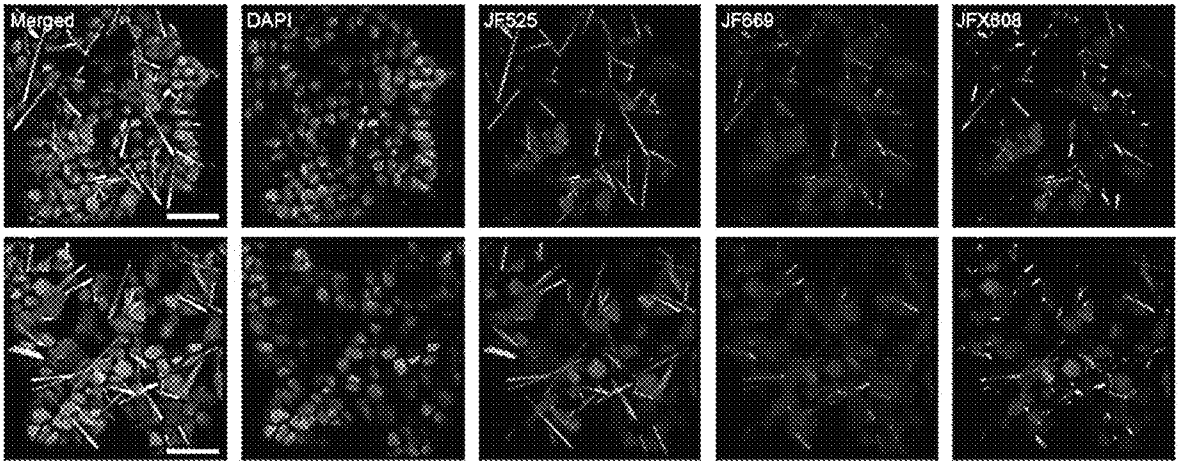
Figure 12D:
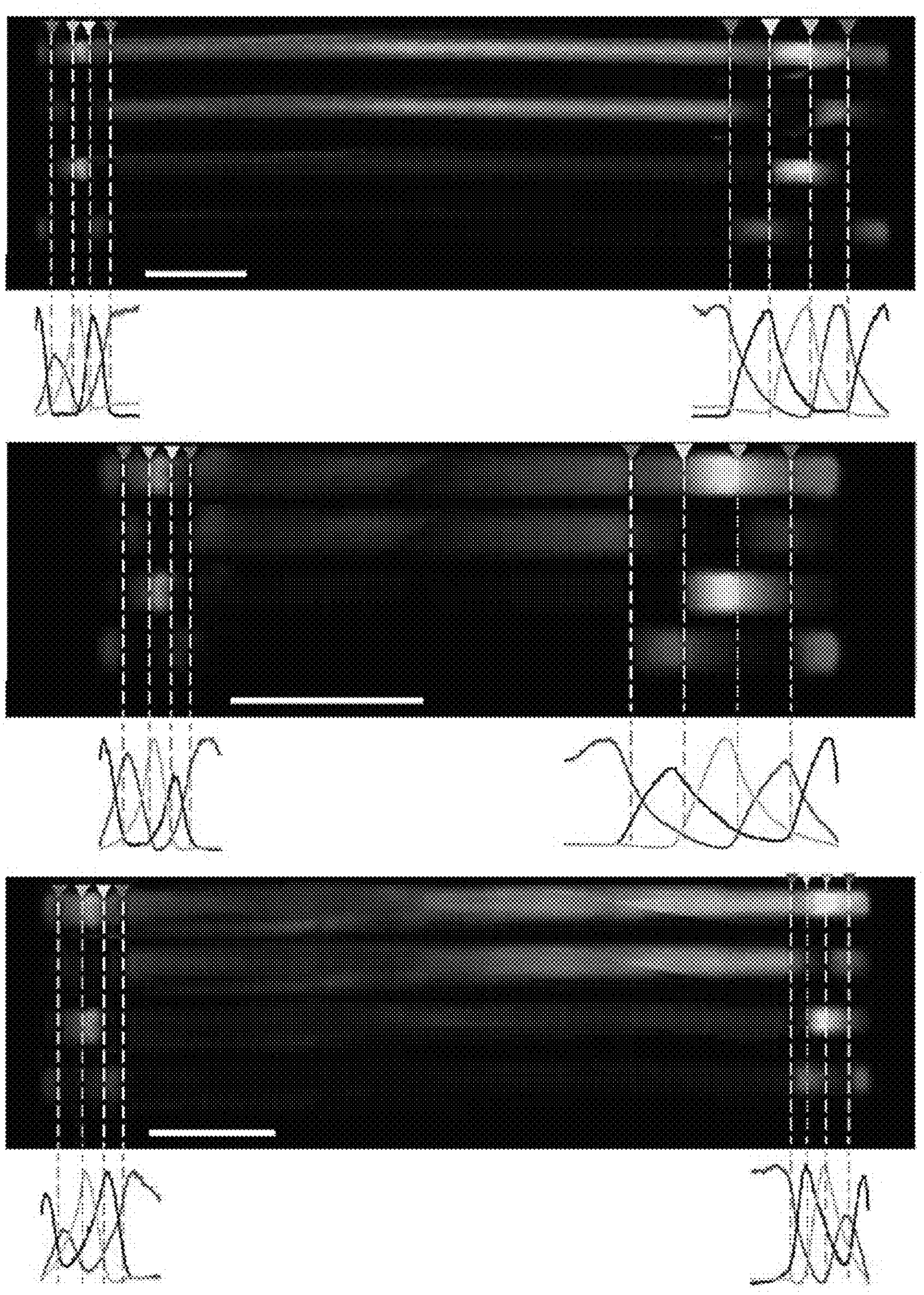
Figure 12E:
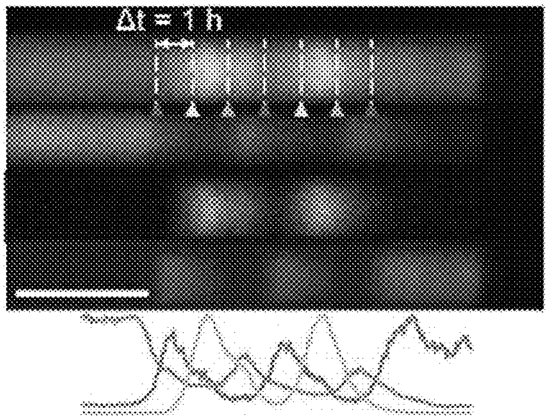

To test the limits of how fast dye transitions could be encoded, assemblies were made with seven dye switches at Δt=1 h. At this short interval, peaks were still visible, but their amplitude was suppressed relative to the parts of the assembly with no dye switches, indicating incomplete transitions in dye labeling (FIG. 12E). Analysis of the dye profiles for more widely spaced dye transitions indicated a half-life of soluble HT-iPAK4 of 4.5 h (FIG. 13A), explaining the loss of signal at faster dye switches. These results indicated that fiducial timestamps should be separated by at least Δt=2 h.

Figure 13A:
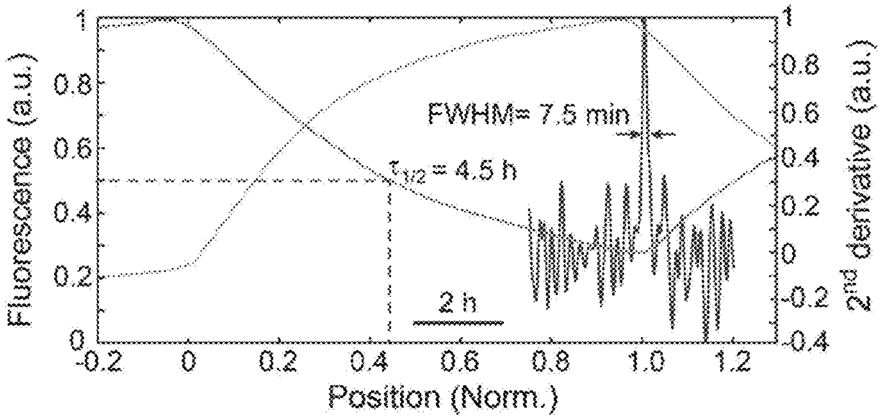
FIGS. 13A-13C show kinetics of HT dye labeling and turnover in HEK293T cells.
Figure 13B:
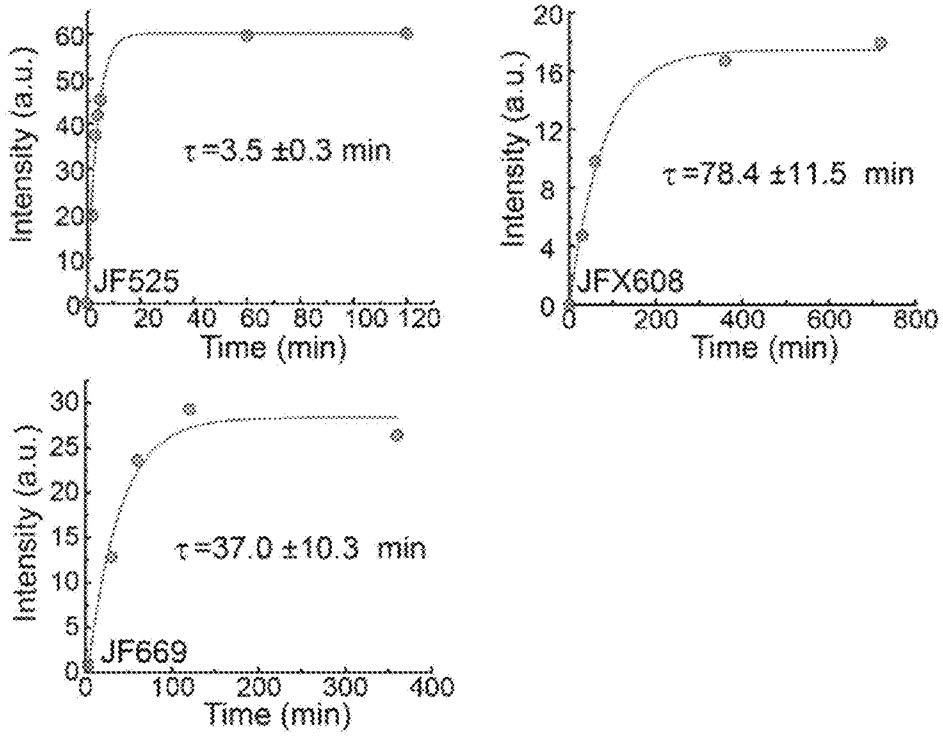
Figure 13C:
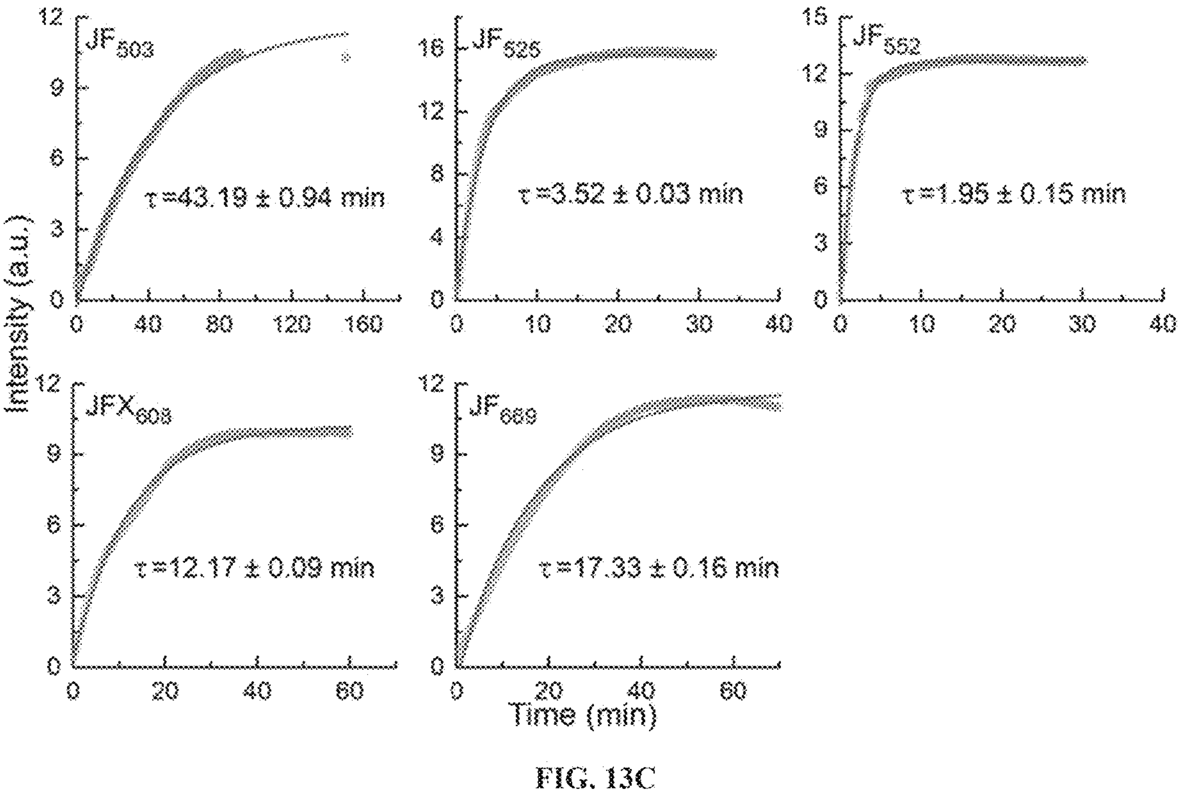
Figure 14:
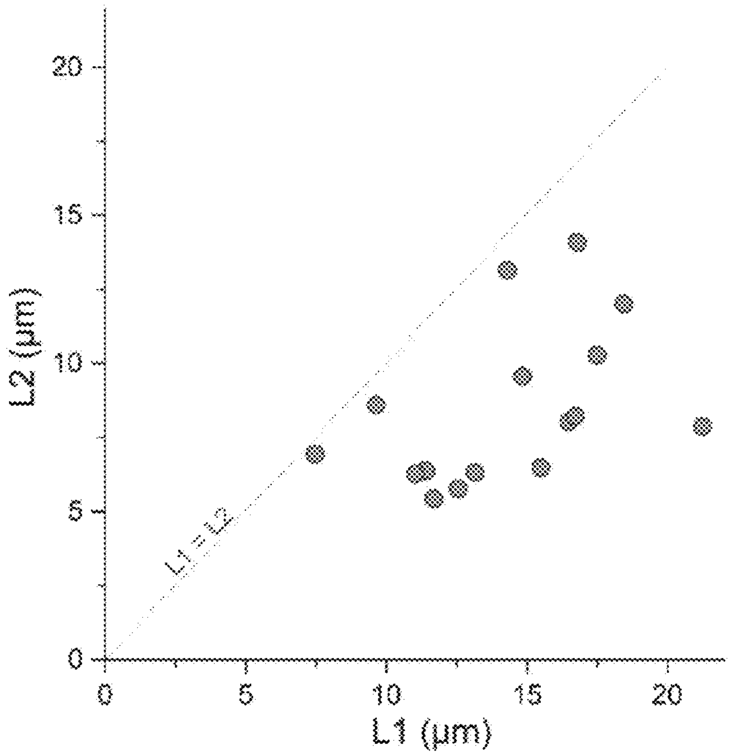
FIG. 14 shows a comparison of growth rates on the faster and slower-growing assembly ends. Dye switches were used to demarcate an 8 h interval on HT-iPAK4 assemblies. Both assembly ends were imaged. The longer end was labeled L1, and the shorter end was labeled L2.
Figure 15A:
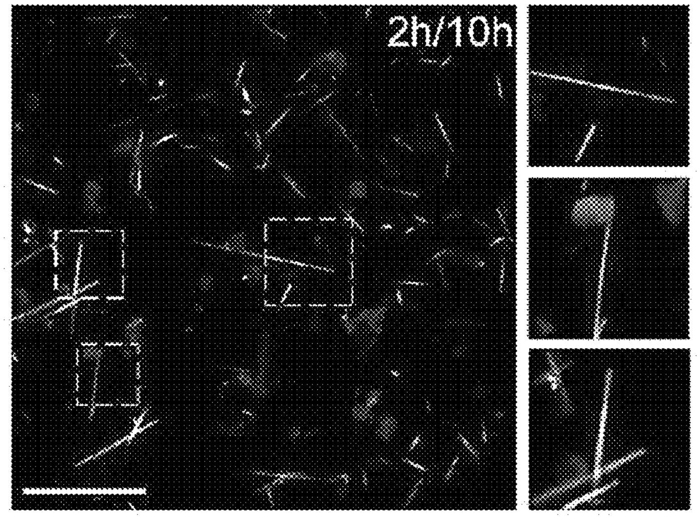
FIGS. 15A-15F show low-magnification images of HT-iPAK4 assemblies with multiple fiducial timestamps. Images show assemblies initially labeled with $JF_{525}$, switched to $JF_{669}$ at t=0, $JFX_{608}$ at t=X, and back to $JF_{525}$ at t=10 h, for X=2 h (FIG. 15A), 4 h (FIG. 15B), 6 h (FIG. 15C), 7 h (FIG. 15D), 8 h (FIG. 15E), and 9 h (FIG. 15F). Insets show the regions in the dashed boxes. Scale bars 100 μm.
Figure 15B:
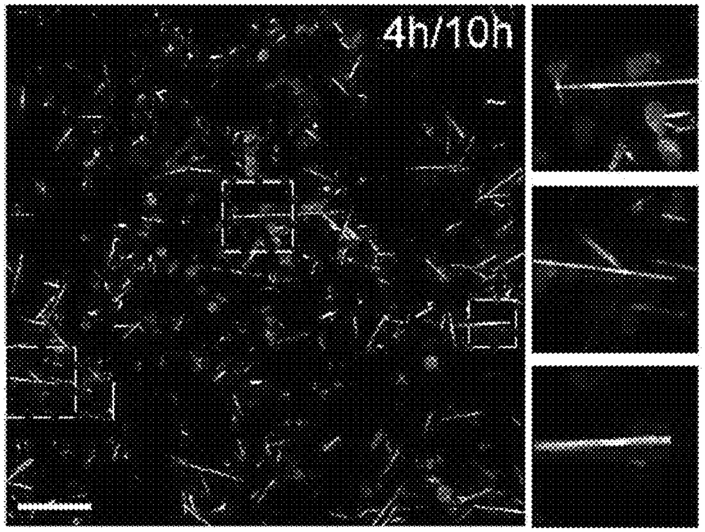
Figure 15C:
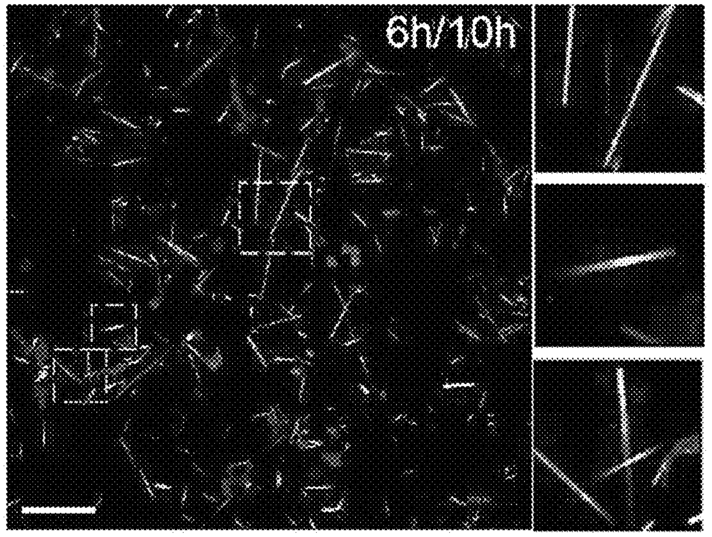
Figure 15D:
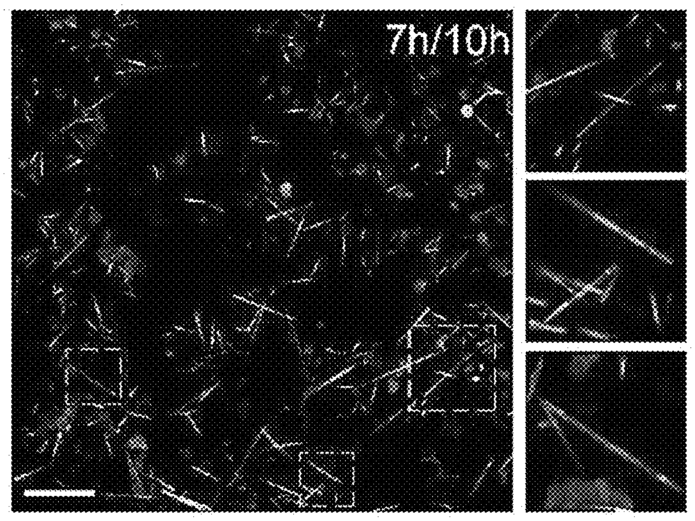
Figure 15E:
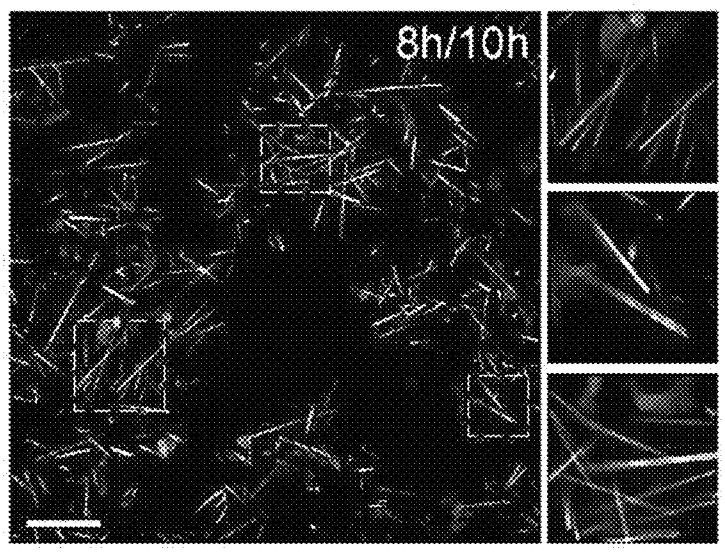
Figure 15F:
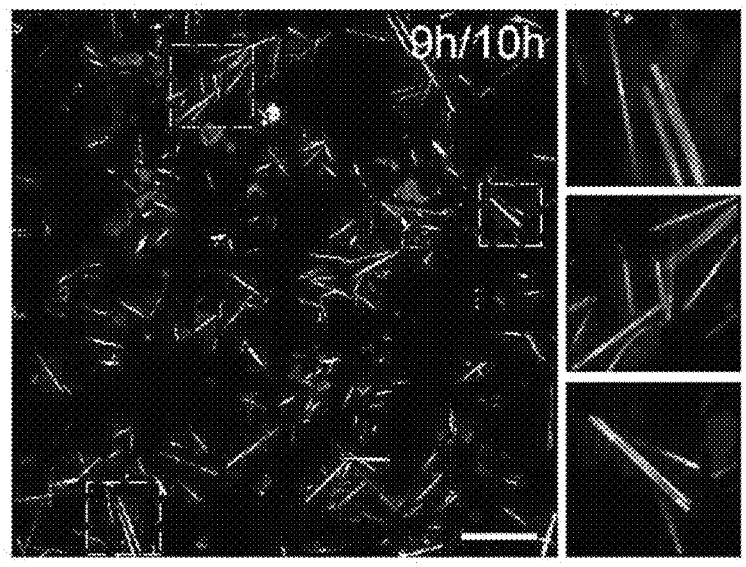

Dye additions appeared as upward-going kinks in the fluorescence profiles (FIGS. 12D, 13A), which were located as peaks in the second derivative of fluorescence vs. position. By dividing the transition zone widths (full-width at half-maximum of the peak in the second derivative) by the assembly-specific growth rates, a mean transition zone duration of 7.5 min was calculated (FIG. 13A). To determine whether the kinetics of HT dye labeling affected the widths of these transitions, the labeling of intracellular HT receptors was measured with several different HT dyes. These measurements probed the combined effects of membrane permeation and the HT reaction. The first-order reaction rate constants were 2.9 $\mu M^{-1}$ $min^{-1}$ ($JF_{525}$), 0.13 $\mu M^{-1}$ $min^{-1}$ ($JFX_{608}$), and 0.27 $\mu M^{-1}$ $min^{-1}$ ($JF_{669}$) (FIG. 13B). These results imply that at the 1 μM dye concentration used, the labeling for all dyes was largely complete in <10 min, consistent with the sharp transitions observed in the assemblies. The effective time constants at 1 μM dye were: 43 min ($JF_{503}$), 3.5 min ($JF_{525}$), 2.0 min ($JF_{552}$), 12 min ($JFX_{608}$), and 17 min ($JF_{669}$) (FIGS. 13A and 13C). The precision of localizing a dye transition in an assembly is not equal to the labeling time constant, but rather the precision with which one can identify the onset of the labeling reaction. For all the JF dyes, this time was much less than 10 min. Together, these results established that HT dye transitions provided a means to timestamp iPAK4 assembly growth with a local precision (i.e., around the time of a time stamp) of ~10 min or better.

Figure 2C:
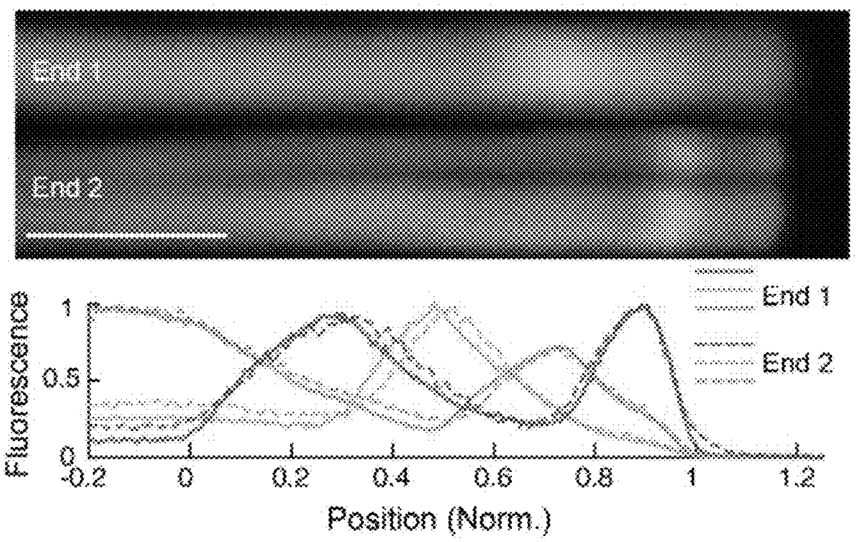

Due to the $P6_3$ symmetry of the iPAK4 crystal structure,[18] the two ends are not chemically equivalent and need not have the same growth rate. However, the asymmetry in growth rate was modest, with the slower end growing, on average, at 62±19% of the speed of the faster end (mean±s.d., N=17 assemblies, FIG. 8). The fluorescence profiles on the two ends were then compared. To account for the difference in growth rate between the assembly ends, the first dye addition was mapped ($JF_{669}$ at t=0) to x=0, and the end of the assembly (fixation at t=8 h) to x=1. After normalizing the spatial scales, the fast and slow-growing assembly ends showed very similar profiles (FIG. 2C).

Figure 2D:
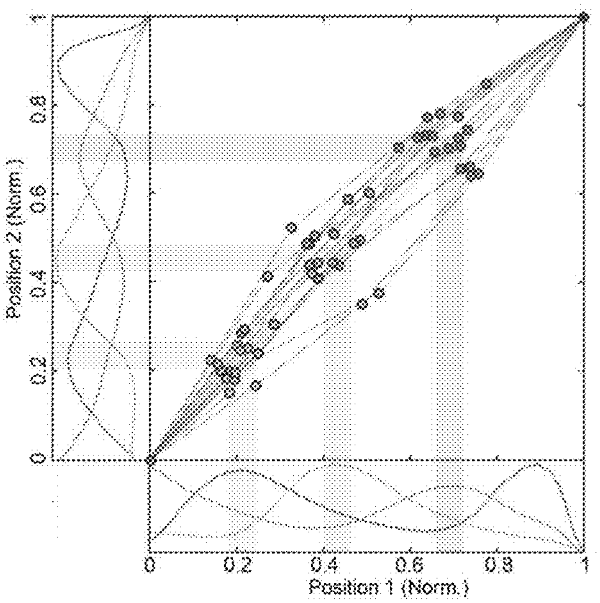

To test whether both assembly ends could be useful for recording fiducial timestamps, the locations of the dye transitions were analyzed on both ends of N=17 assemblies. For both the faster and slower-growing ends, the normalized locations of dye transitions at t=2, 4, and 6 h mapped linearly onto position between the first dye addition (t=0) and the end of the assembly (t=8 h) (FIG. 2D). The standard deviations in the inferred timing (averaging over the three transitions) were 18.3 min on the fast end and 24.8 min on the slow end. Together, these results established that both ends of the assemblies could record fiducial timestamps with an absolute accuracy of better than 25 min over an 8 h baseline.

If the residual errors in timing were driven by a factor shared by the two assembly ends (e.g., variations in iPAK4 expression level), then these errors would lie primarily along the diagonal line Position 1=Position 2 in FIG. 2D. The cross-correlation in the timing errors between the two assembly ends was calculated and averaged over all transitions (t=2, 4, and 6 h) and all assemblies. This cross-correlation was only 0.32, implying that dynamic fluctuations in growth rate were primarily driven by factors local to each end. In principle, timing precision could be improved by averaging measurements on the two assembly ends, but it was found that often the image quality was better on one end than the other because of differences in the focal plane or the presence of out-of-focus assemblies. Consequently, only one assembly end per cell was typically analyzed, and distinguishing between the faster- and slower-growing ends was not attempted.

Figure 2E:
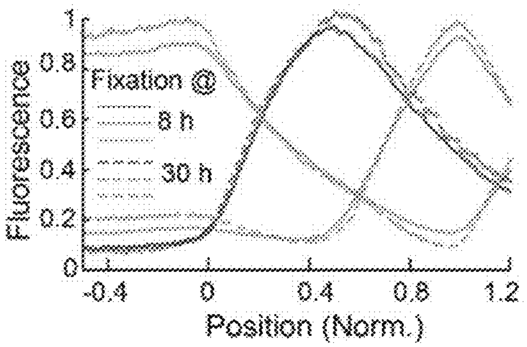
Figure 2F:
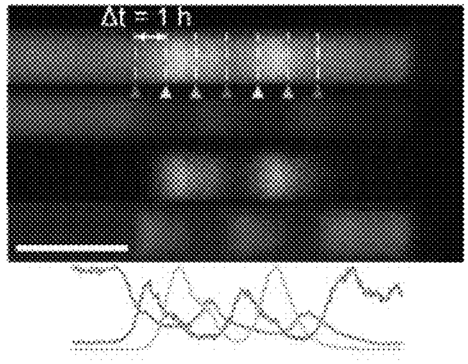
Figure 2G:
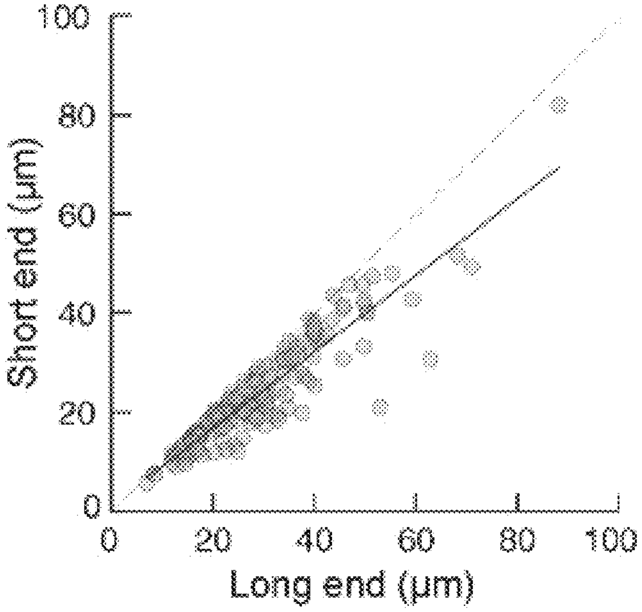

A protein ticker tape may stably store its information for extended times. Since the iPAK4 assemblies were held together by non-covalent interactions, it was tested whether monomer exchange blurred the HT dye boundaries over time. Two dishes were exposed to the same sequence of dye switches at intervals of Δt=2 h. One dish was fixed at t=8 h, and the other was returned to the incubator and fixed a day later at t=30 h. The fluorescence profiles for the section of the assemblies that grew concurrently (from t=0 to 8 h) were then compared. The mean profiles were nearly indistinguishable between the early dish (N=22 assemblies) and the late dish (N=12 assemblies) (FIG. 2E). Thus, monomer exchange was negligible over one day.

The precision with which the timing of cellular events could be identified was studied next. If each assembly end grew at a constant rate, the timing of cellular events could be linearly interpolated between timestamps with a precision far greater than the interval between the timestamps. However, fluctuations in the growth rate might degrade the precision. To determine the precision empirically, assemblies were incubated in $JF_{525}$, and then switched to $JF_{669}$ at t=0. In different dishes the dye $JFX_{608}$ was doped in at t=2, 4, 6, 7, 8, or 9 h to simulate the onset of a cellular event.

Figure 3A:
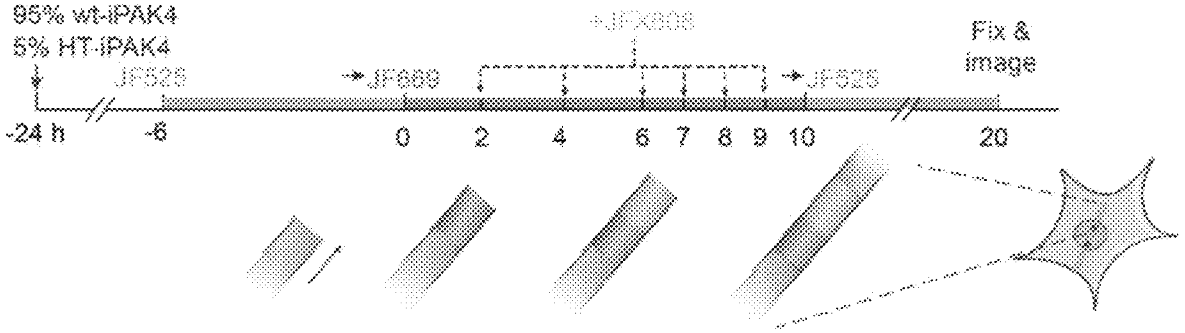
FIGS. 3A-3F show that iPAK4 assemblies report timing of intracellular events.
Figure 3B:
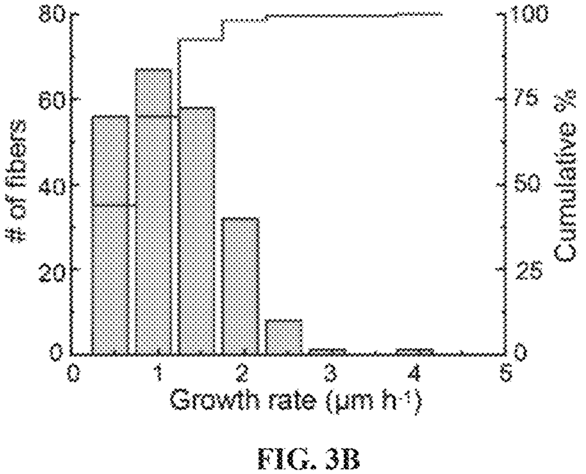
Figure 3C:
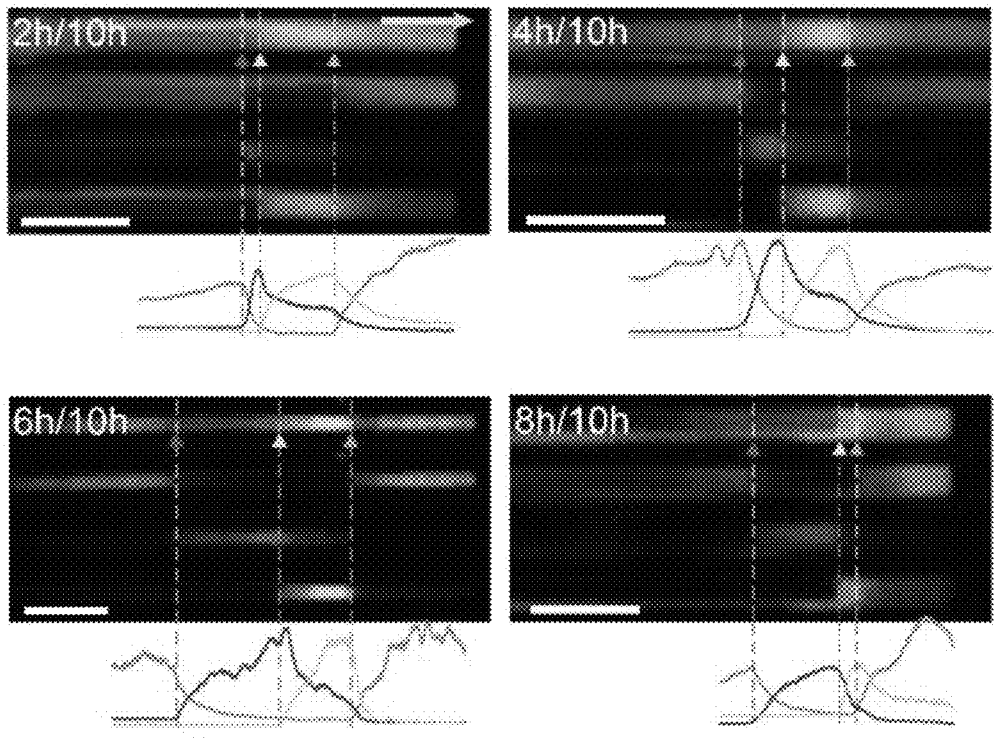
Figure 3D:
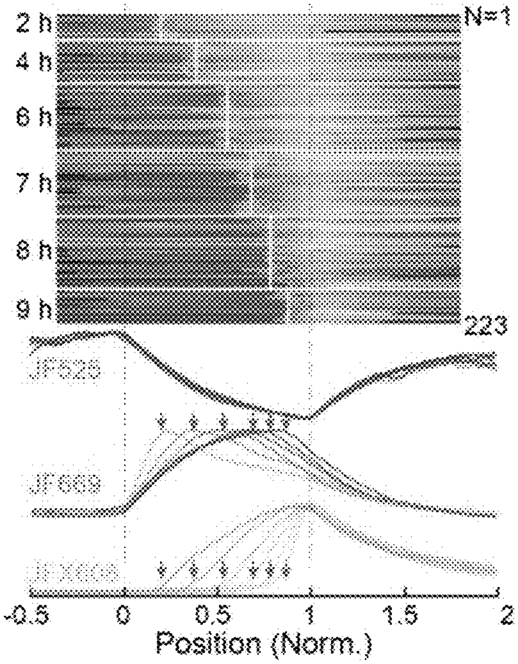
Figure 3E:
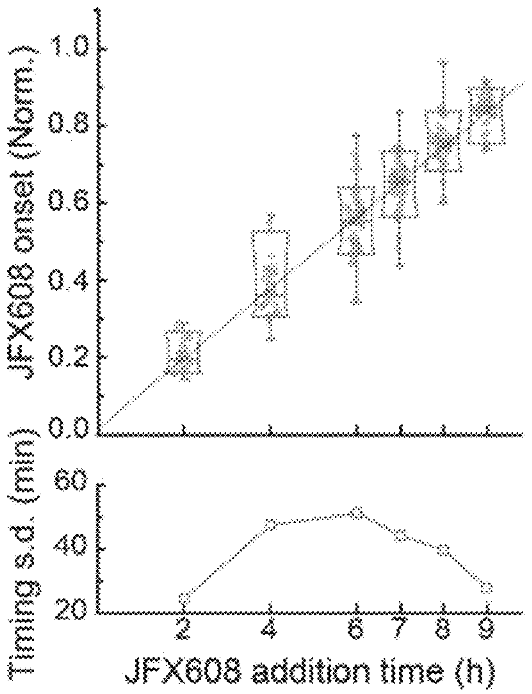
Figure 3F:
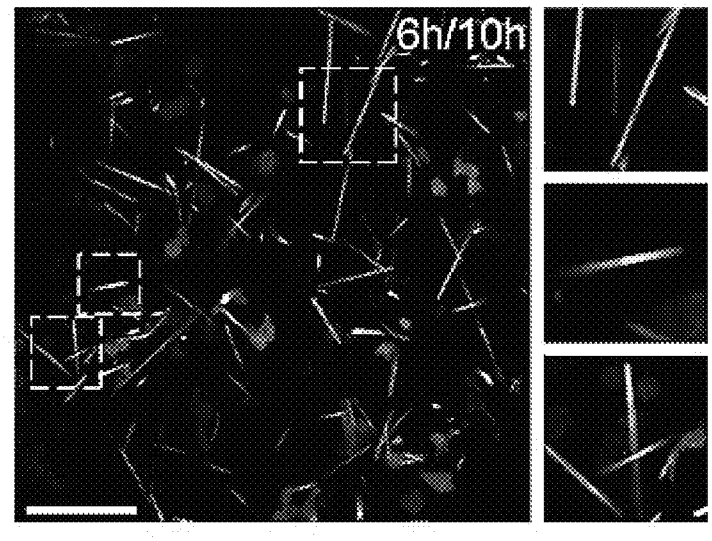

Finally, $JF_{525}$ was doped in again at t=10 h, the assemblies were grown for another 10 h, and the dishes were fixed at t=20 h (FIG. 3A). Low-magnification images showed clear stripes in most assemblies, corresponding to the time stamps and the addition of $JFX_{608}$ (FIG. 3F).

Over the 10 h interval between addition of $JF_{669}$ and return to $JF_{525}$, the assemblies grew at 1.1±0.58 μm/s (mean±s.d., N=223 assemblies; FIG. 3B). Visual inspection of the assemblies with $JFX_{608}$ addition at different time-points showed clear onset of yellow staining at the corresponding positions along the red band (FIG. 3C). The three-color fluorescence profiles of N=223 assemblies (20 to 51 assemblies per time-point of $JFX_{608}$ addition) were qualified, and the locations of the three dye additions ($JF_{669}$, $JFX_{608}$, $JF_{525}$) were identified. As above, each fluorescence trace was mapped so that the first and third dye additions occurred at x=0 and 1, respectively (FIG. 3D).

The mean traces clearly showed the time-dependent onset of $JFX_{608}$ fluorescence, which was also evident in low-magnification images of the assembly population (FIGS. 15A-15F). The distributions of $JFX_{608}$ onset were then quantified. The distribution linearly mapped dye addition time to normalized position between 0 and 1 (FIG. 3E). Mapping the standard deviation of $JFX_{608}$ labeling onset onto the 10 h time axis yielded single-assembly precisions between 25 and 51 min (FIG. 3E). The precision was greatest near the fiducial points at t=0 and 10 h, and lowest in the middle of the trajectory. This observation established that the uncertainty in $JFX_{608}$ timing was dominated by intracellular fluctuations in the assembly growth rate as opposed to errors in locating the $JFX_{608}$ transition points, since localization errors would be statistically similar anywhere along the assembly. Thus, to achieve greatest temporal precision for detecting an event, a fiducial timestamp may be deposited near the candidate event.

Time-Tagged iPAK4 Assemblies Record Dynamics of Gene Expression

Figure 4A:
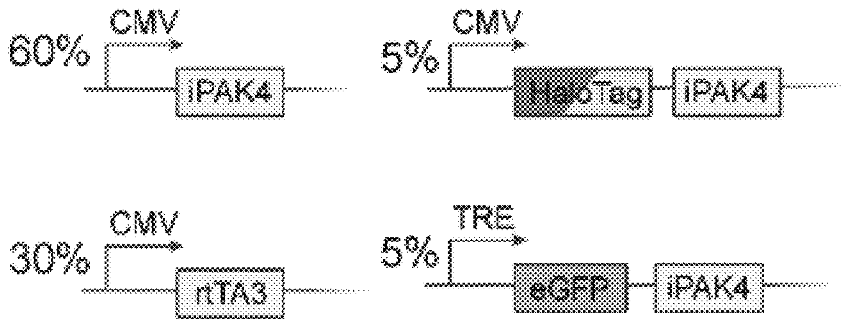
FIGS. 4A-4D show protein ticker tape recordings of doxycycline (DOX) activation of Tet-ON system in HEK cells.
Figure 4B:
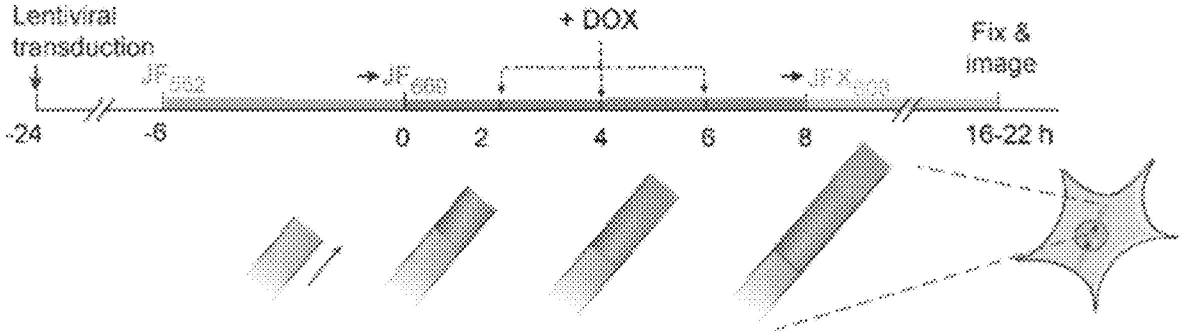

As the first test of a physiological recording, iPAK4 assemblies were used to report on a transcriptional activator, the tetracycline mediated Tet-ON transcription system.[28] HEK cells were co-infected with lentivirus containing CMV::iPAK4 (60%), CMV::rTTA3 (30%), CMV::HT-iPAK4 (5%), and CMV::eGFP-iPAK4 (5%) to establish tetracycline-dependent eGFP-iPAK4 expression (FIG. 4A). After assemblies had nucleated (24 h after lentiviral infection), $JF_{552}$ was added to label the initial nuclei, and $JF_{669}$ was added at t=0. In different dishes, doxycycline (DOX, 2 μg/mL) was added at t=2, 4, or 6 h to activate expression of eGFP-iPAK4. Then $JF_{552}$ was added again at t=8 h, and the assemblies were grown for another 8-14 h before fixation and imaging (FIG. 4B).

Figure 4C:
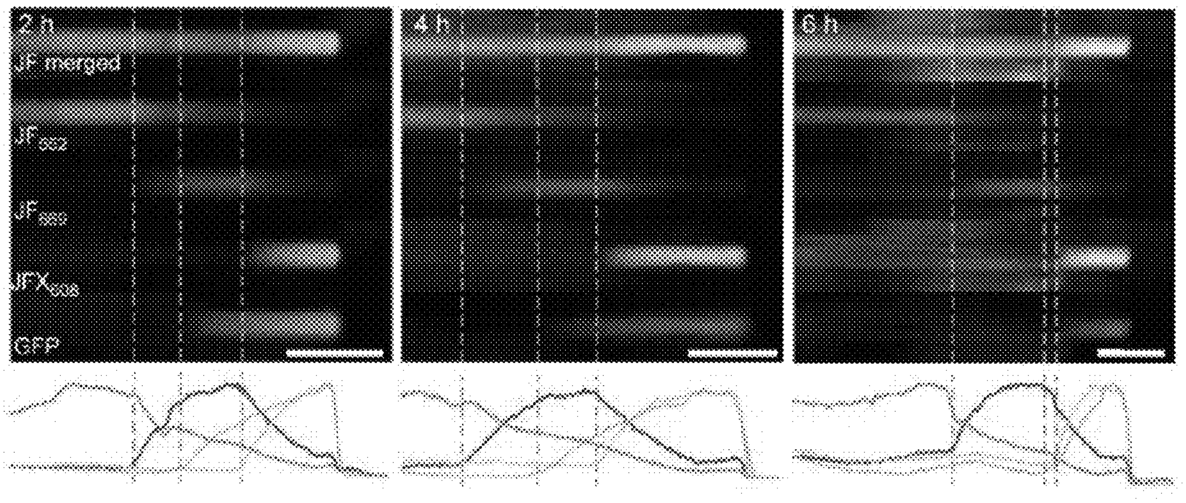
Figure 4D:
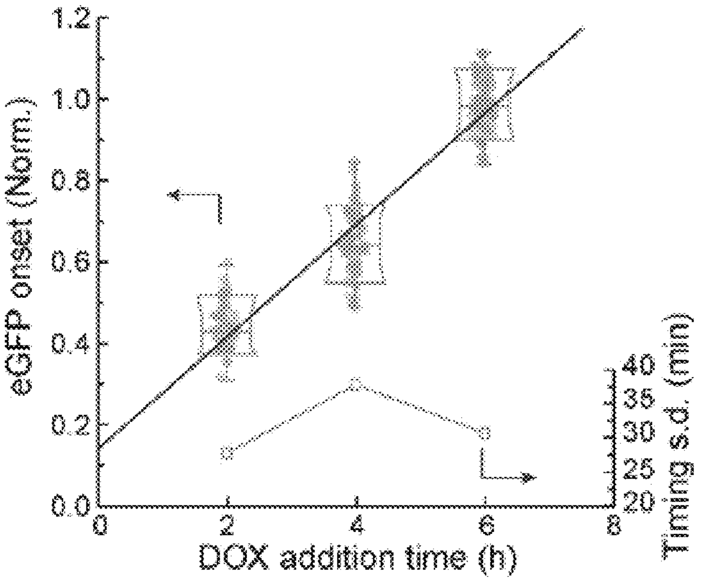
Figure 16A:
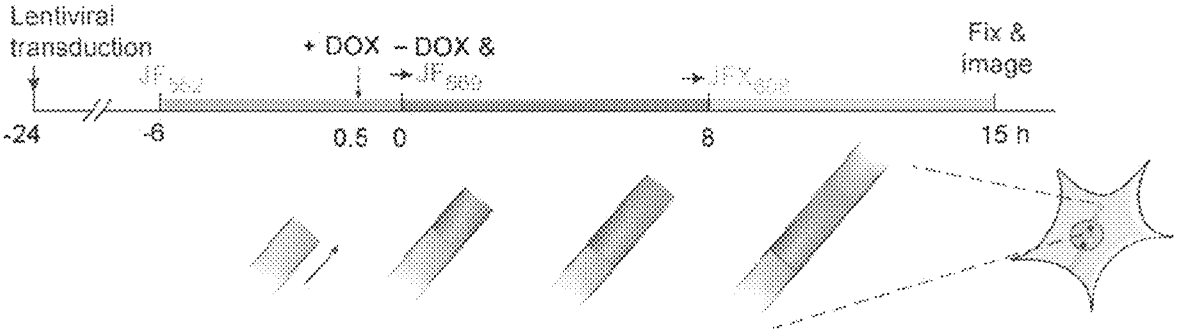
FIGS. 16A-16B show recordings of impulse response of protein expression following pulsed doxycycline (DOX) activation in HEK293T cells. Related to FIG. 4.
Figure 16B:
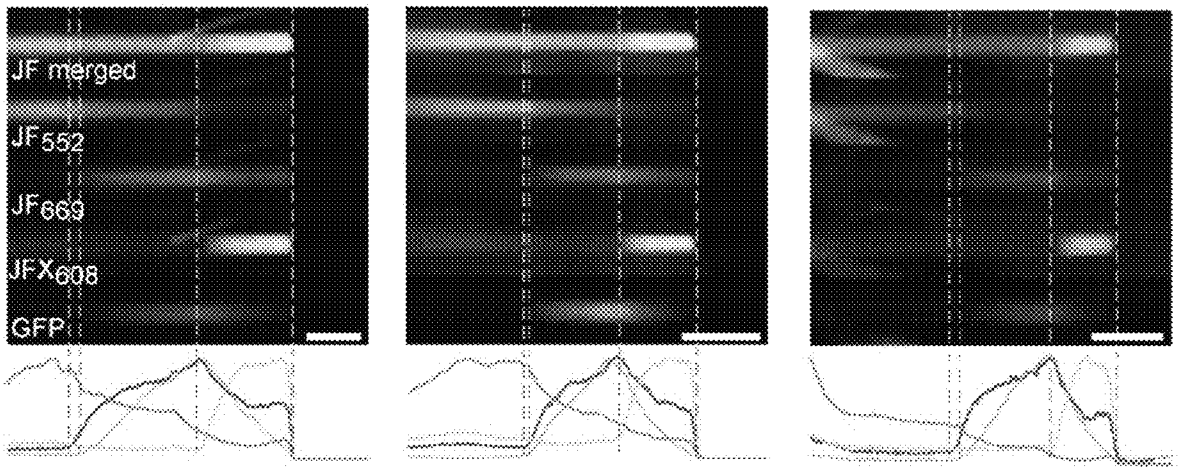

DOX addition led to formation of green bands in the assemblies, with onset at positions linearly related to DOX addition time (N=191 assemblies, FIGS. 4C-4D). Based on the assembly-to-assembly variations in the positions of the green onsets, an absolute timing accuracy of 30-40 min over an 8 hour baseline was inferred. A linear fit to the band positions yielded an apparent offset of 1.2 h between DOX addition and the start of the green stripe. This delay was ascribed to the time required for transcription, translation, and protein folding. Similar experiments where cells were exposed to a 30-minute pulse of DOX caused eGFP-iPAK4 expression to rise for approximately 8 h and then fall, leading to a ~14 h window of protein expression (FIGS. 16A-16B). These experiments demonstrate that the iPAK4 ticker tape system can quantify the dynamics of protein expression in single cells.

Figure 17A:
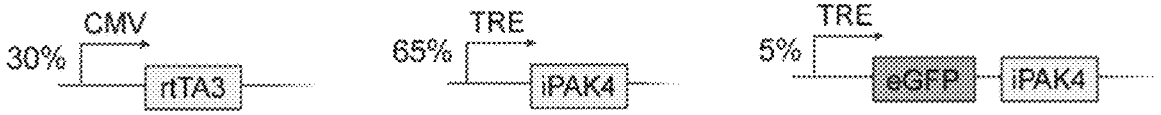
FIGS. 17A-17C show controlled onset of iPAK4 assembly growth with Tet-ON system in HEK293T cells. Related to FIG. 4.
Figure 17B:
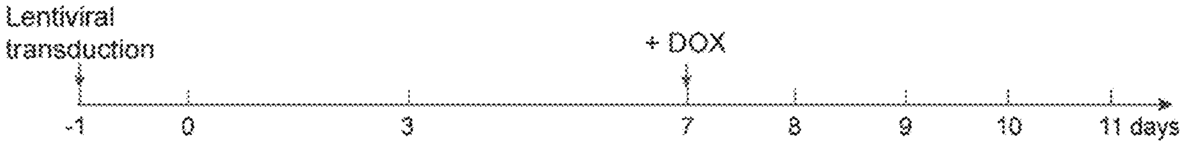
Figure 17C:
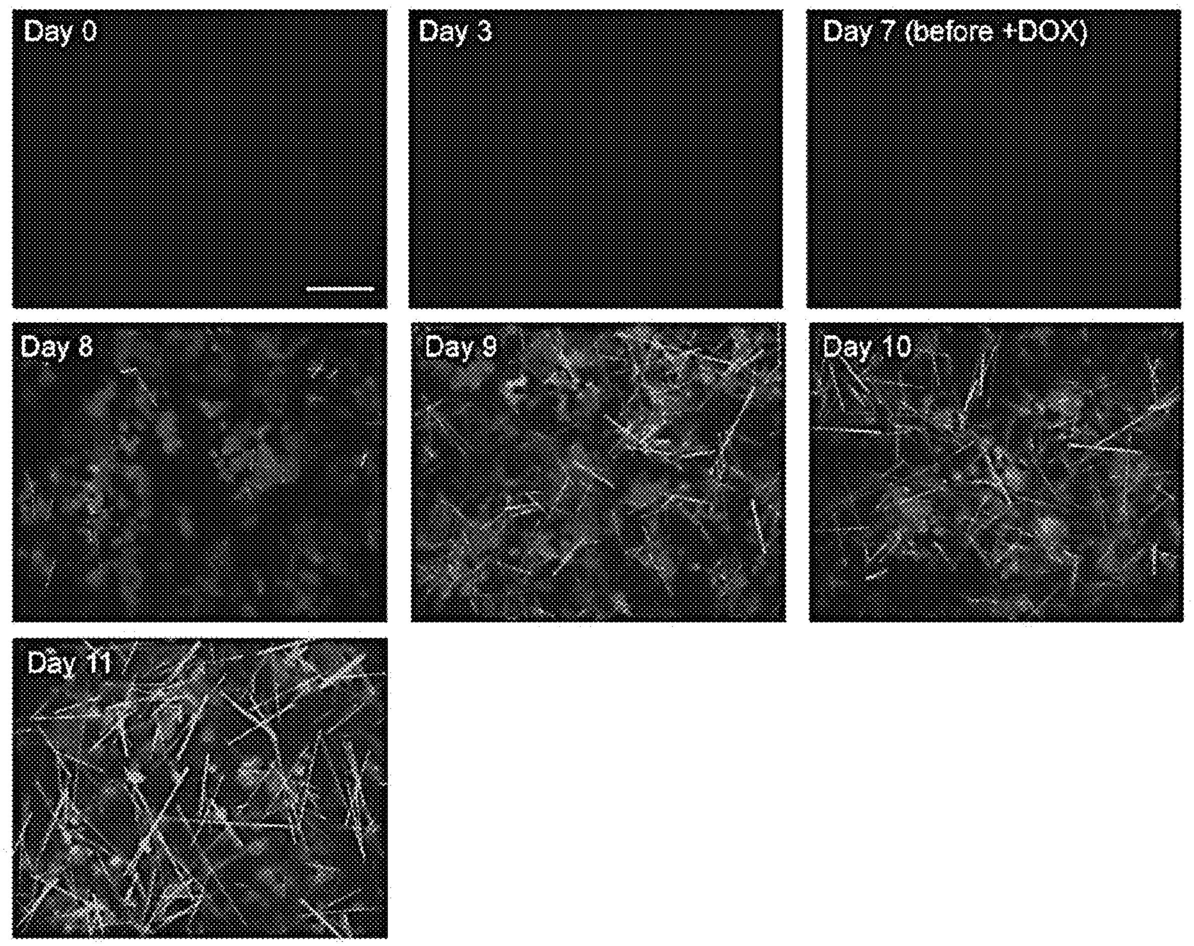
Figure 18A:
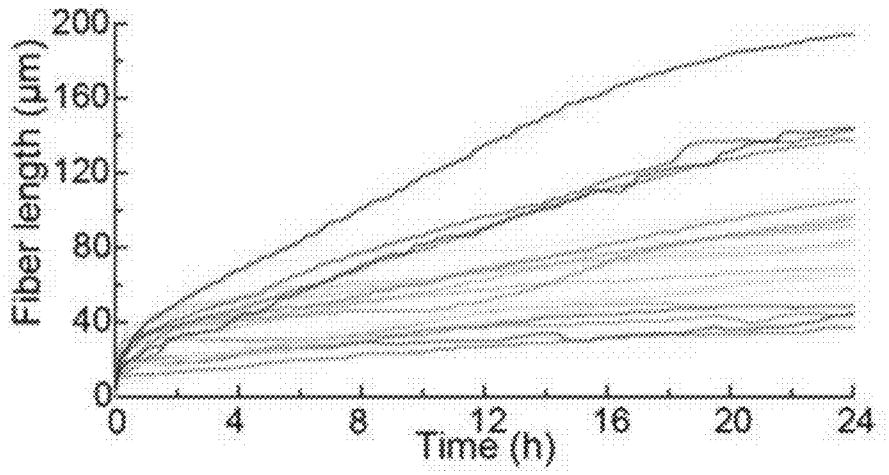
FIGS. 18A-18F show iPAK4 assembly growth kinetics in primary neuron culture. Related to FIG. 5.
Figure 18B:
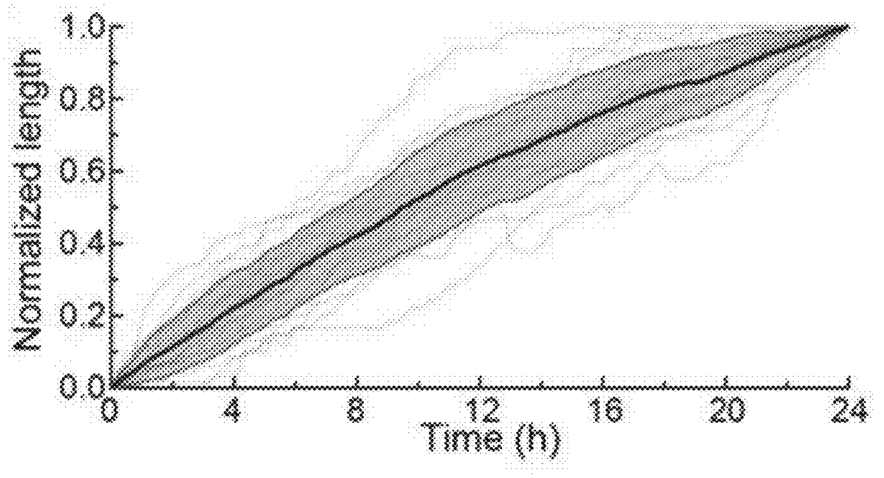
Figure 18C:
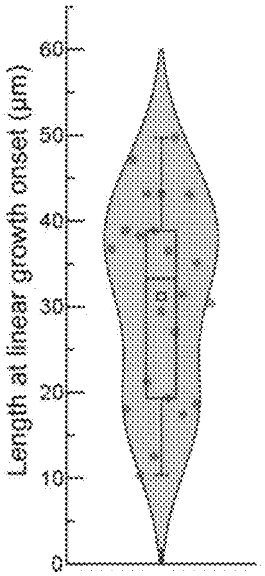
Figure 18D:
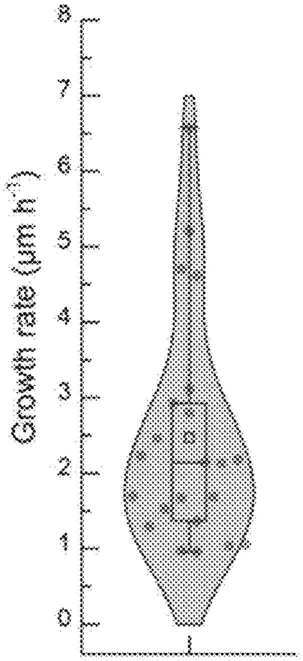
Figure 18E:
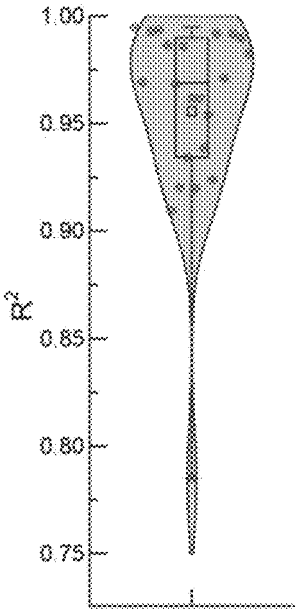
Figure 18F:
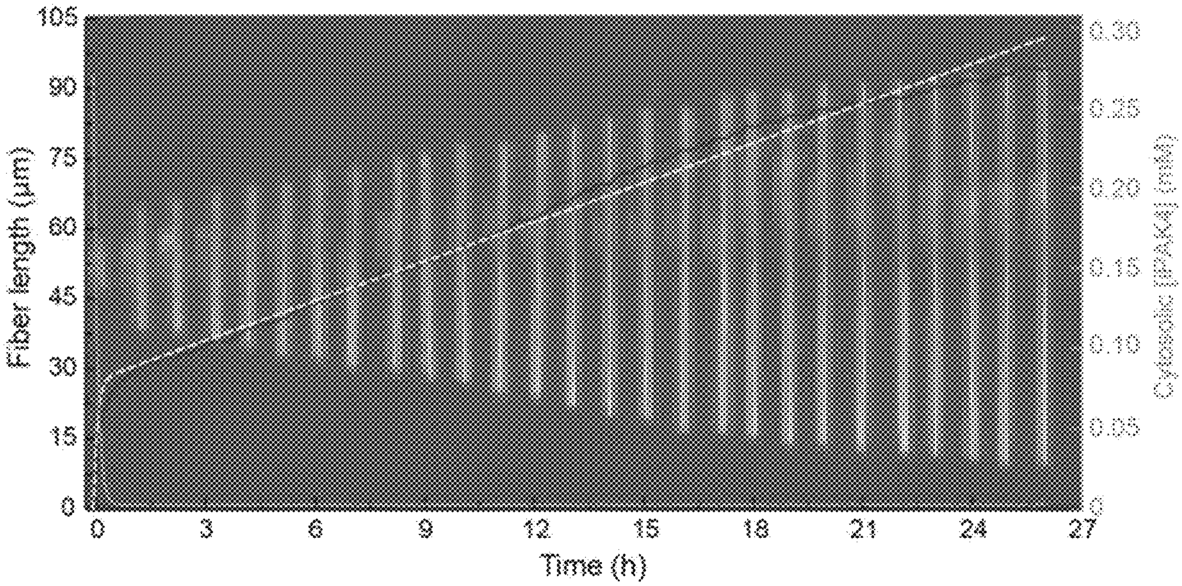

The Tet-ON system also provides a means to control the onset of iPAK4 nucleation, allowing a separation between gene delivery and the start of a recording. CMV::rtTA3 (30%), TRE::iPAK4 (65%), and TRE::eGFP-iPAK4 (5%) were co-expressed in HEK cells using lentiviral transduction, and DOX was added after 7 days (FIGS. 17A-17C). In the first 7 days, negligible eGFP signal was observed, indicating minimal background expression of the Tet-ON system. After DOX addition, iPAK4 assemblies were observed starting on day 8, with clear elongation of the assemblies over the following day. Inducible ticker tape expression is therefore a powerful tool for defining recording windows to coincide with specific experimental perturbations.

Time-Tagged iPAK4 Assemblies Record Neural Activation

Figure 21:
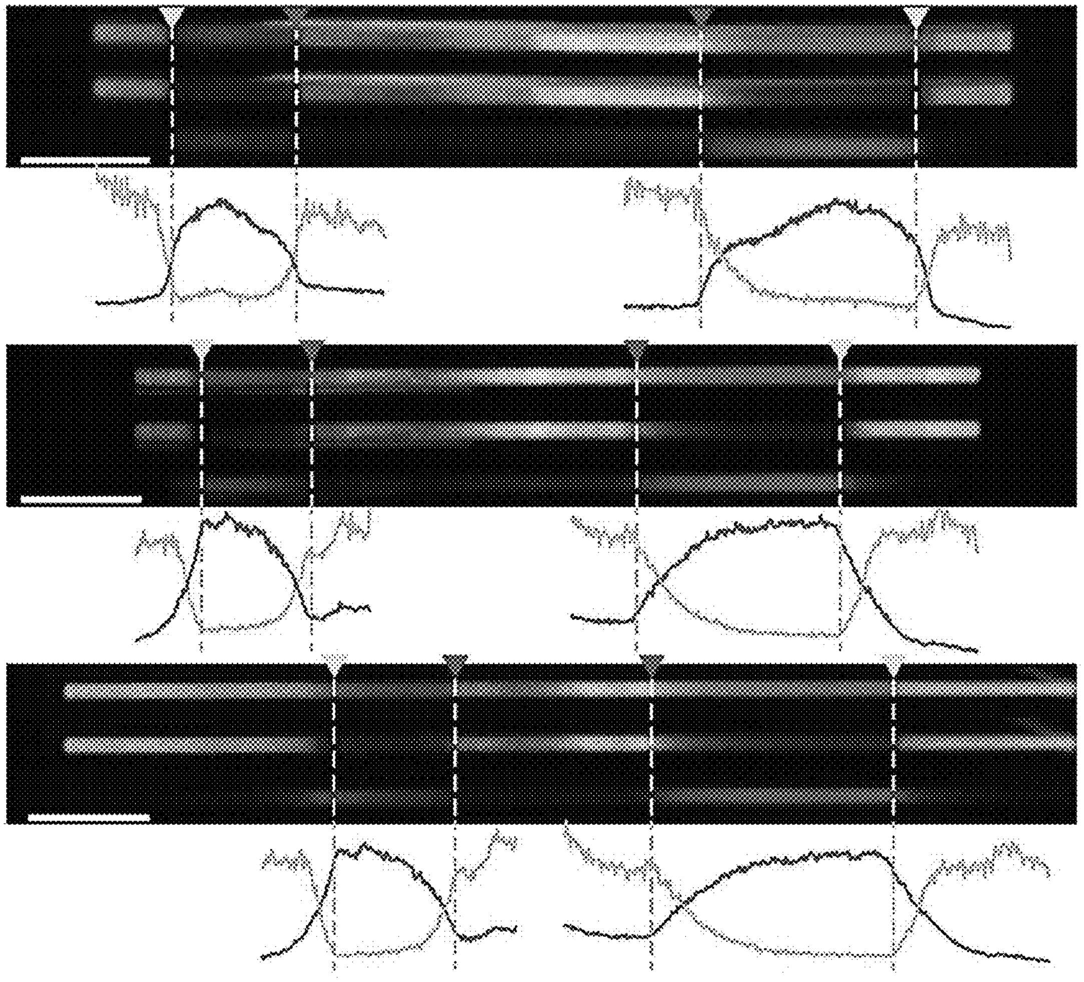
FIG. 21 shows fiducial timestamps in neurons expressing HT-iPAK4. Related to FIG. 5. Neurons were co-infected with lentivirus encoding CMV::iPAK4 (90%) and CMV::HT-iPAK4 (10%). Neurons were initially labeled with $JFX_{608}$ for 24 h, then with $JF_{669}$ for 24 h, and then with $JFX_{608}$ for another 24 h. Images show individual assemblies (top), the $JFX_{608}$ and $JF_{669}$ color channels separately (middle), and fluorescence profiles of each color channel (bottom). Scale bars 10 μm.

Finally, the ability of iPAK4 ticker tapes to report activation of the IEG cFos was tested in cultured rat hippocampal neurons. The ability of switches in HT dye labeling to impart fiducial time stamps on HT-iPAK4 assemblies was first confirmed in neurons (FIG. 21). To establish iPAK4 assembly recordings in neurons, it was first verified that: (1) the assemblies grew linearly in neurons; (2) a dye switch introduced fiducial time stamps in neurons; and (3) the assemblies did not introduce cytotoxicity or changes to neuronal electrophysiology.

To characterize assembly growth in neurons, time-lapse imaging was performed over 33 h in a primary neuron culture lentivirally infected with CMV::iPAK4 (90%) and CMV::HT-iPAK4 (10%). Assemblies of iPAK4 nucleated and grew in neurons, following a similar trajectory as seen in HEK cells comprising a fast-growing nucleation phase followed by slower linear growth (FIGS. 18A-18F). Occasionally, assemblies were observed to stall for a few hours, or sometimes stop growing altogether. Stalled assemblies were flagged by requiring a mean growth rate of >0.8 μm/hr. This excluded 11 of 33 tracked assemblies (33%). A key point is that the growth rate threshold could be applied based on a single terminal measurement of assembly length, and thus did not require time-lapse imaging.

Figure 19A:
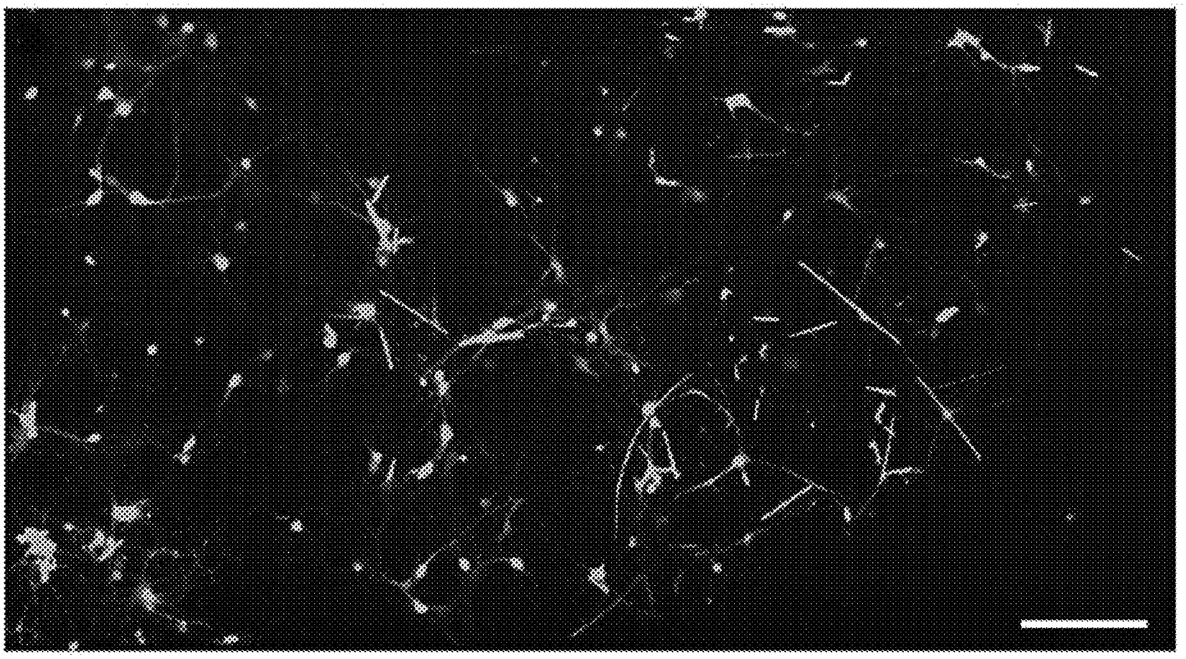
FIGS. 19A-19B show primary neuron culture with iPAK4 assemblies. Related to FIG. 5, FIG. 19A provides a representative image of primary neuron culture with CMV::iPAK4 (95%) and CMV::HT-iPAK4 (5%) delivered via lentivirus and stained with $JF_{552}$. Scale bar 200 μm.
Figure 19B:
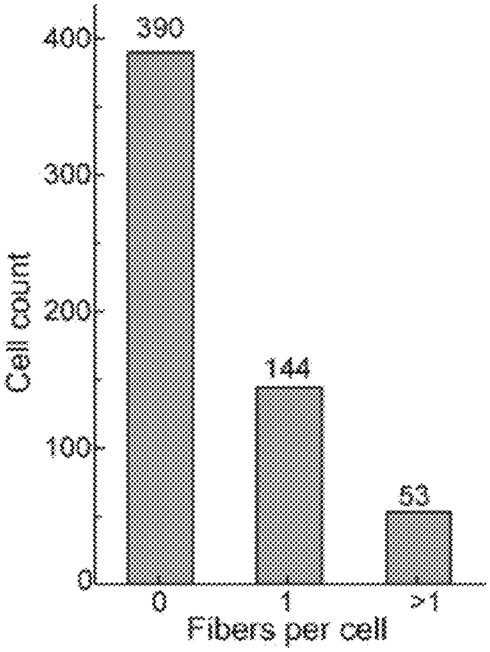
Figure 20A:
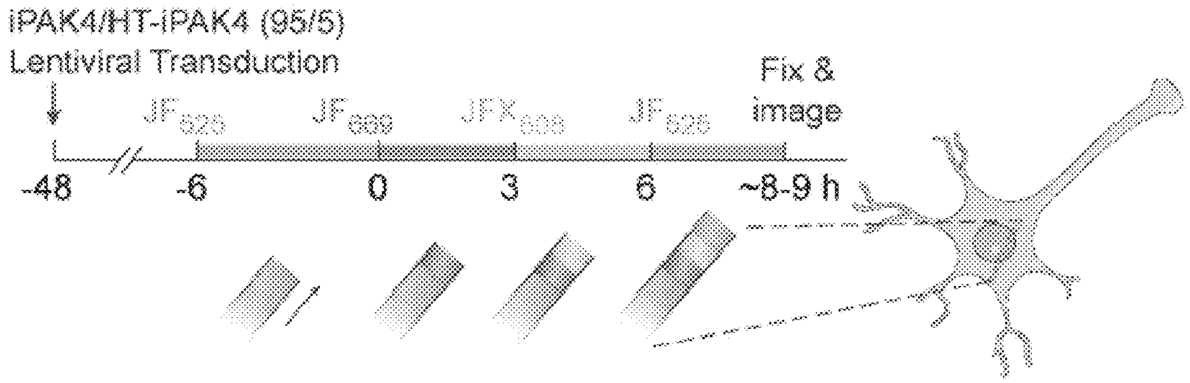
FIGS. 20A-20C show color stripes in sequentially labeled HT-iPAK4 assemblies in primary neuron culture. Related to FIG. 5, FIG. 20A provides a scheme for multi-color labeling of intracellular iPAK4 assemblies. HEK293T cells were co-infected with CMV::iPAK4 (95%) and CMV::HT-iPAK4 (5%). After the onset of assembly growth, cells were washed at Dt=3 h intervals in the sequence $JF_{525}$, $JF_{669}$, $JFX_{608}$, then $JF_{525}$.
Figure 20B:
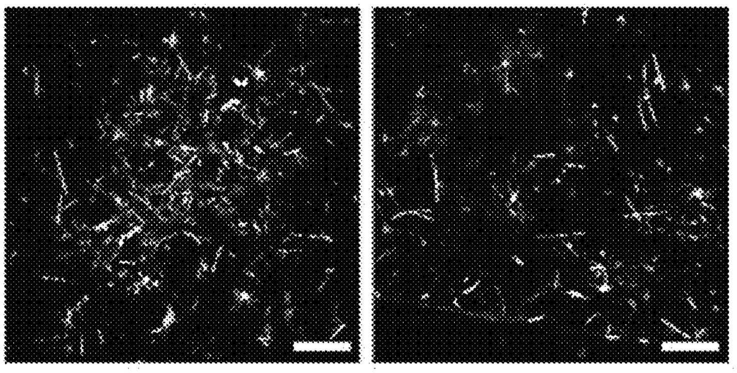
Figure 20C:
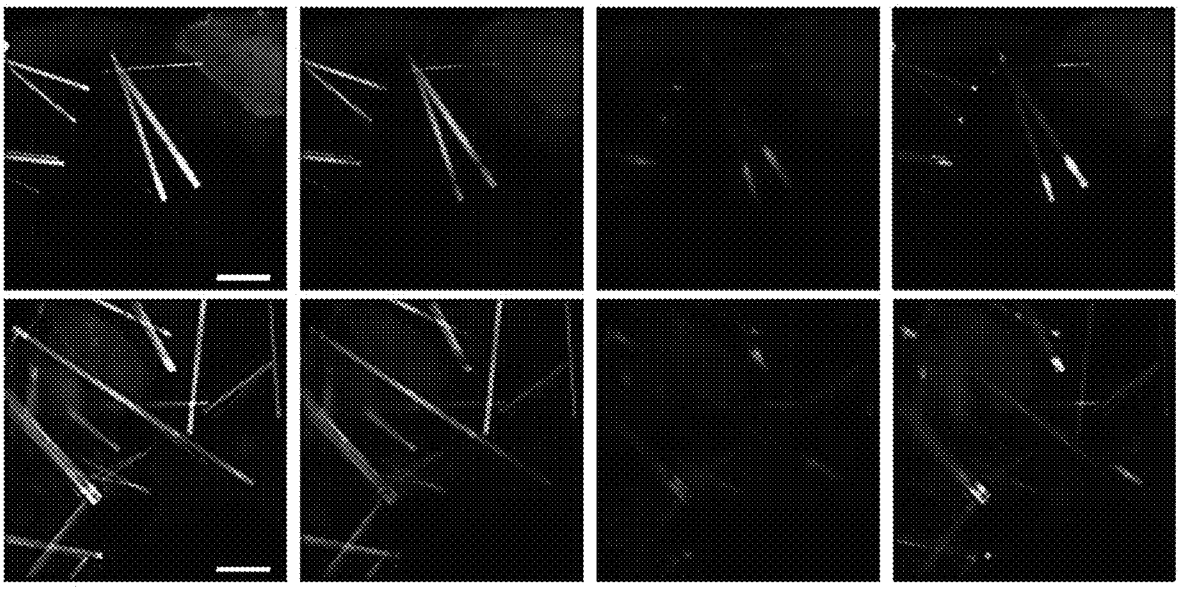

Of the assemblies that passed the growth rate criterion, the assembly length at onset of linear growth was 31±12 μm (mean±s.d., N=22 assemblies). The growth rate in the linear phase was 2.5±1.5 μm/h. During the linear growth phase, the fit to a straight line growth profile had a mean $R^2$=0.95±0.04, over a 24 h interval. Of the neurons that had assemblies, most (73%) had only one assembly, although many neurons did not have assemblies nucleated at the time of the recording (FIGS. 19A-19B). Dye switch experiments in neurons were also performed, and the ability of switches in HT dye labeling to impart fiducial time stamps on HT-iPAK4 assemblies in neurons was also confirmed (FIGS. 20A-20C, FIG. 21).

Figure 22A:
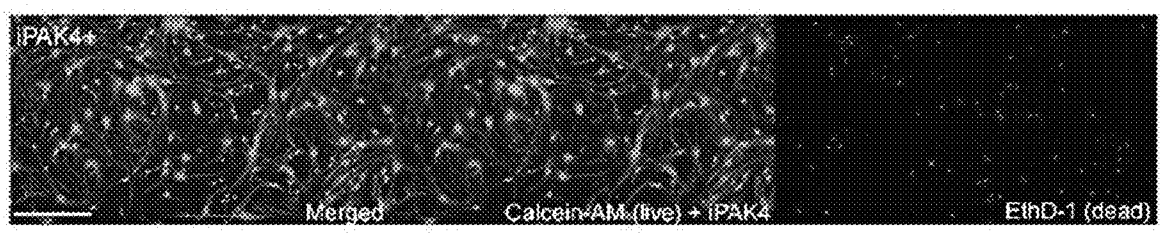
FIGS. 22A-22C show that iPAK4 assemblies do not affect neuronal survival. Related to FIG. 5.
Figure 22B:
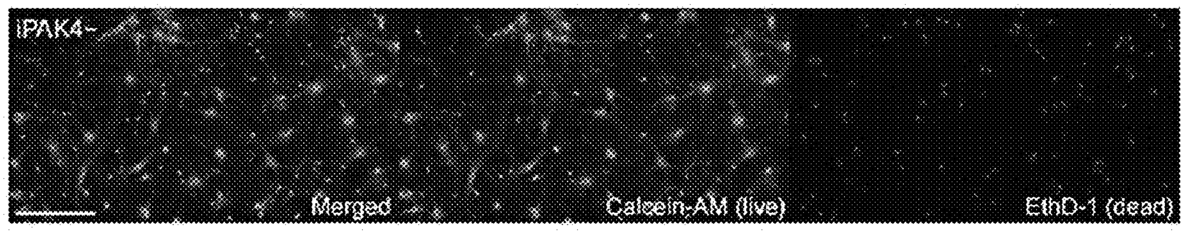
Figure 22C:
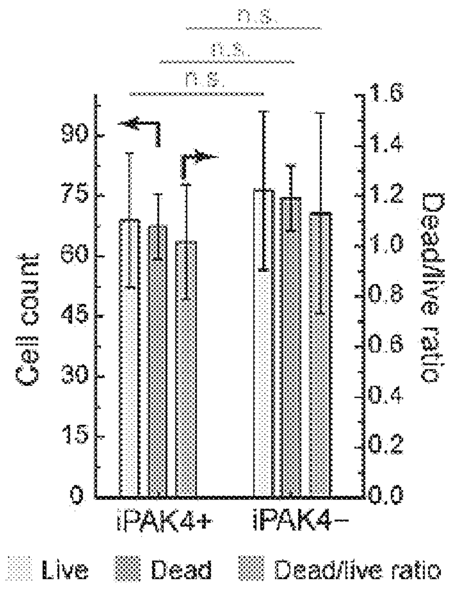
Figure 23A:
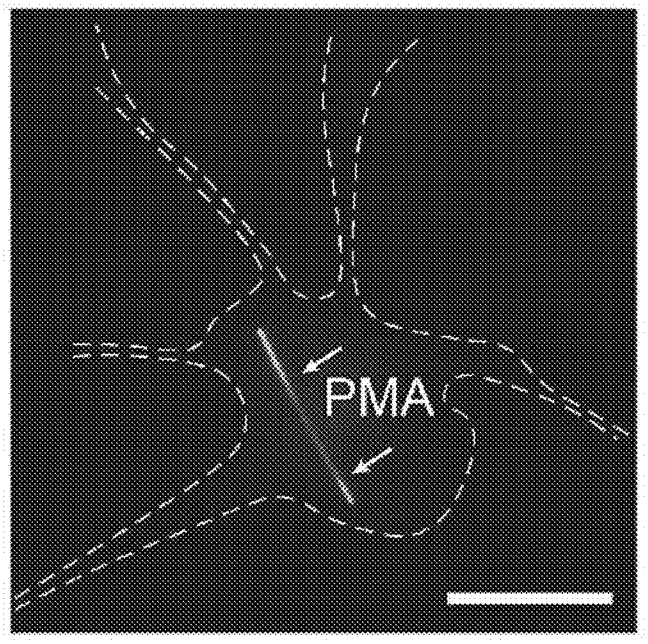
FIGS. 23A-23B show monitoring of cFos activation in neurons. In neurons expressing CMV::iPAK4 (90%) and cFos::eGFP-iPAK4 (10%), addition of PMA activated the cFos promoter and led to formation of fluorescent stripes in the assemblies.
Figure 23B:
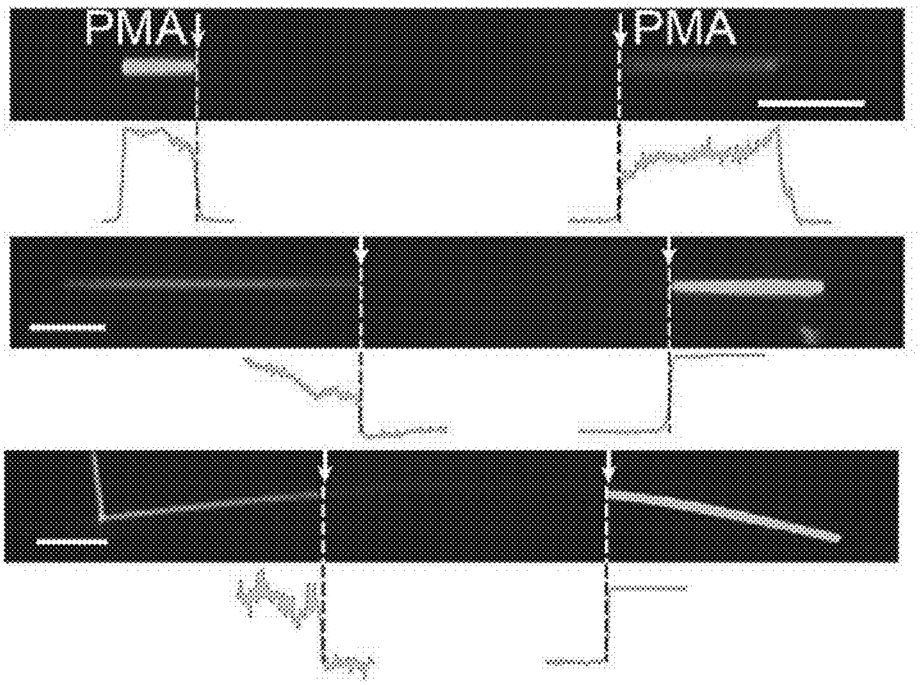

To test for effects of iPAK4 assemblies on neuronal survival, iPAK4 (95%) and HT-iPAK4 (5%) were lentivirally expressed in cultured neurons, the assemblies were allowed to grow for 6 days, and then a live-dead assay was performed (FIGS. 22A-22C). There was no significant difference in the fraction of dead cells between dishes expressing iPAK4 assemblies and dishes not infected with any lentivirus. The iPAK4-expressing neurons had typical soma and neurite structures, similar to those observed in healthy neurons.

Figure 5A:
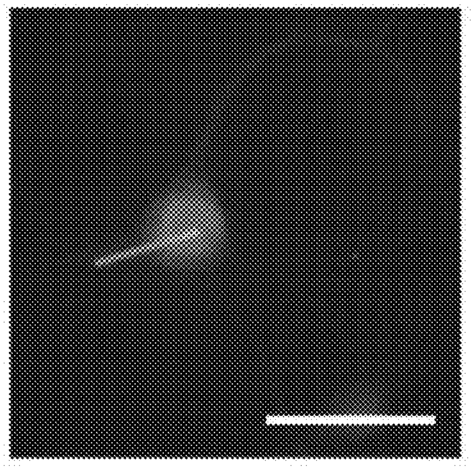
FIGS. 5A-5H show protein ticker tape recordings of cFos activation in neurons.
Figure 5B:
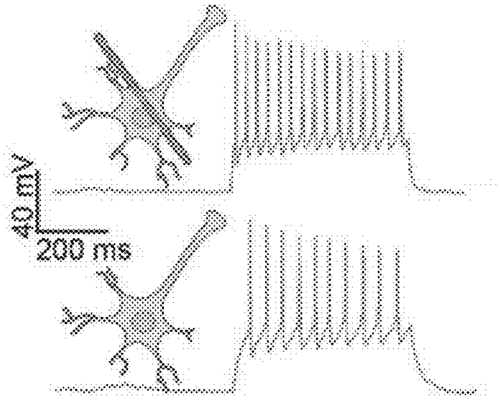
Figure 5C:
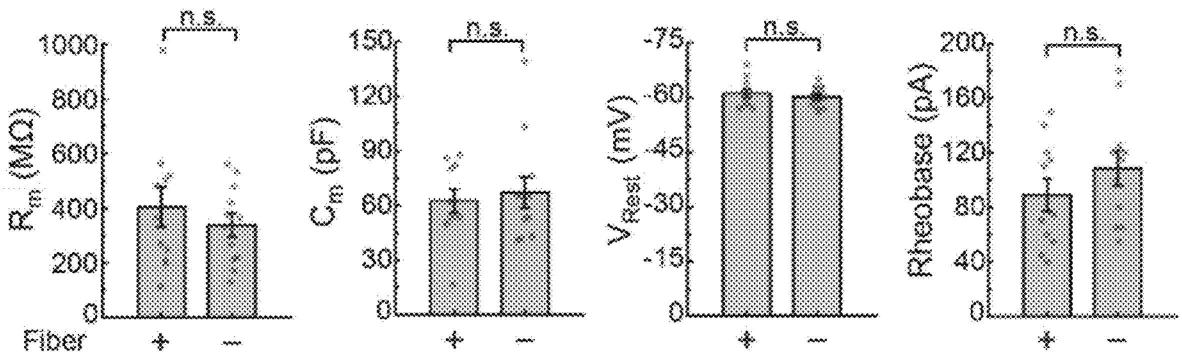
Figure 5D:
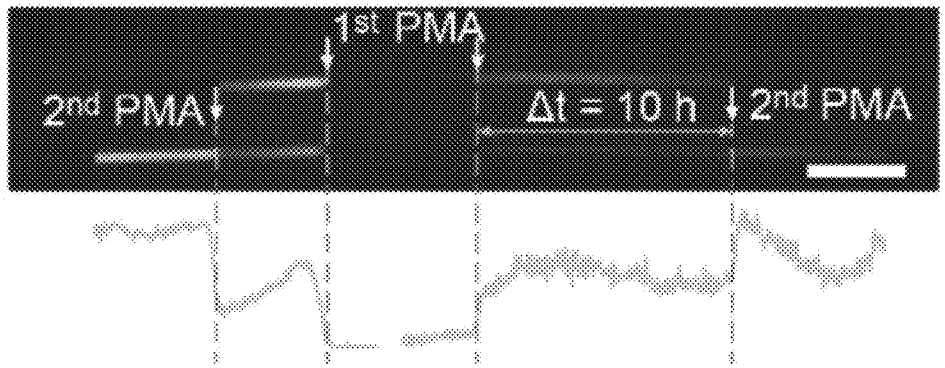

Whether iPAK4 assemblies affected neuronal electrophysiology was then tested. Neurons infected with lentivirus encoding CMV::iPAK4 (90%) and CMV::eGFP-iPAK4 (10%) grew single straight assemblies (FIG. 5A). Patch clamp recordings were used to compare the electrophysiology of neurons with and without assemblies. Although in many cases the assembly length was several times longer than the soma diameter, neurons with assemblies spiked normally (FIG. 5B), and had membrane resistance, membrane capacitance, resting potential, and rheobase that were statistically indistinguishable from neurons without assemblies (N=11 neurons with assemblies, N=12 without, two-sided Student's t-test, FIG. 5C).

Figure 5E:
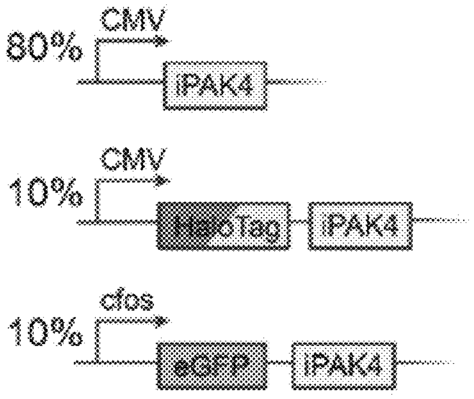
Figure 5F:
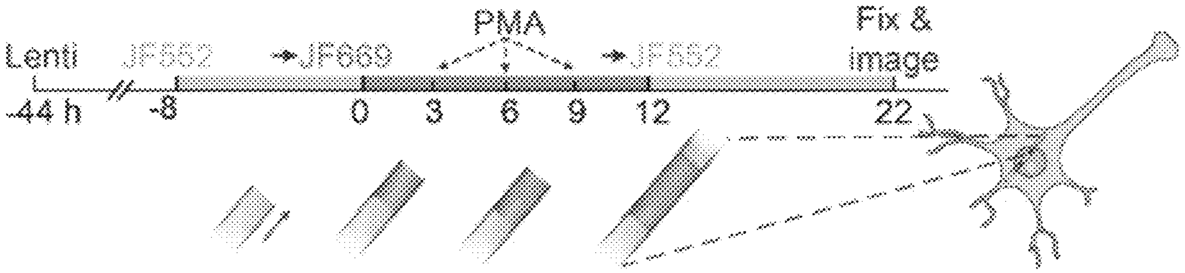
Figure 5G:
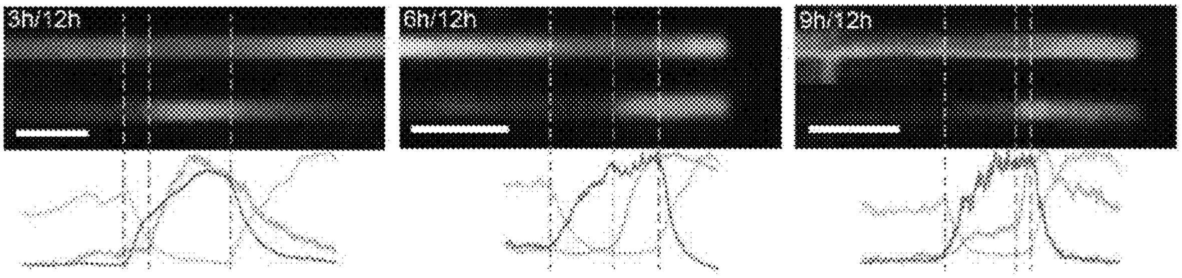

In neurons co-expressing CMV::iPAK4 (90%) and cFos::eGFP-iPAK4 (10%), assemblies initially grew with little green fluorescence. Addition of phorbol 12-myristate 13-acetate (PMA, 1 μM), an activator of cFos expression,[29] led to bands of bright green fluorescence (FIGS. 23A-23B, 13A-13C). Sequential additions of PMA to a single dish led to distinct bands of eGFP fluorescence, clearly resolved by sharp eGFP boundaries (FIG. 5G).

To measure timing of cFos activation relative to fiducial timestamps, CMV::iPAK4 (80%), CMV::HT-iPAK4 (10%), and cFos::eGFP-iPAK4 (10%; FIG. 5E) were co-expressed. The neurons were stained with JF552, and then switched to JF669 at t=0. PMA (1 μM) was then added at t=3, 6, or 9 h, and a second fiducial timestamp was introduced by switching back to JF552 at t=12 h. Assemblies were grown until t=22 h and then fixed and imaged (FIG. 5F).

Figure 5H:
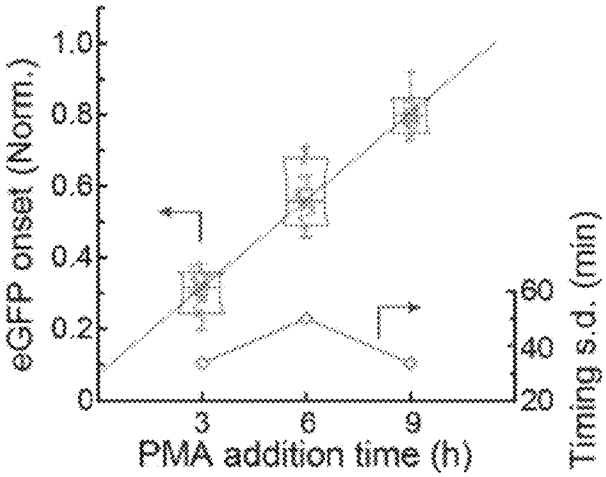

Clear green bands were observed, indicating cFos-driven expression of eGFP-iPAK4. To infer an onset time for each band, the onset of eGFP fluorescence relative to the two dye switches was mapped. The slope of the plot of inferred eGFP onset time vs. nominal PMA addition time was 0.98±0.10 (mean±95% CI, N=34 assemblies at 3 h, 32 assemblies at 6 h, 40 assemblies at 9 h). Extrapolating this fit to t=0 implied that eGFP onset was delayed by 53 minutes relative to the timing of PMA addition (FIG. 5H). This delay was interpreted as the time for PMA to activate the cFos promoter plus delays of transcription, translation, and protein folding of eGFP-iPAK4. The standard deviations in the inferred eGFP onset times were 34 min (3 h), 50 min (6 h), and 34 min (9 h), implying an average absolute timing accuracy of 39 minutes over a measurement with 12 h between fiducial time stamps.

Discussion

Slowly growing protein assemblies are a promising substrate for massively parallel cellular recordings. The recording strategy relies on three key elements: a protein scaffold, a means to impart fiducial timestamps, and a fluorescent reporter (or other physiological signal) of cellular activity that is irreversibly incorporated into the scaffold during growth. Many alternative strategies may be employed for each of these three elements.

The fiducial timestamps are a particularly important conceptual and practical aspect of the approach described herein. Timestamps permit detection, and in some cases correction, of many sources of variability that could otherwise confound the recordings. Here, the timestamps were used to correct for cell-to-cell variations in the linear-phase growth rate, via a simple linear interpolation scheme. The timestamps can also flag individual cells in which there were substantial fluctuations in growth rate during a recording. These would manifest as distinct stripes having widths out of proportion to the corresponding dye incubation times. The timestamps can also flag assemblies that nucleated after the first dye switch: such assemblies would have their central portion tagged with a mixture of dyes instead of solely with the first dye. Assemblies which fractured or aggregated would have timestamps that deviated from the anticipated color order. Thus, the timestamps provide a robust means of calibration and quality control within each cell.

Thinner assemblies may also be engineered, either by modifying the iPAK4 scaffold to enhance the ratio of axial to radial growth, or by using a different assembly-forming protein which forms thinner assemblies.[14] Thinner assemblies would undergo Euler buckling at the cell membrane rather than deforming the cell, though if the assembly becomes so thin that the thermal persistence length is smaller than a few microns, optical tracking of the assembly backbone could be difficult.

An additional modification that can be made to the scaffolds is to decrease the ratio between the soluble iPAK4 concentration at assembly nucleation, $C_{nuc}$, and the concentration during steady state growth, $C_{SS}$. Fits to the simple kinetic model of assembly growth (FIGS. 7A-7E) suggest that this ratio is currently ~100. Consequences of this high ratio are that (a) there is a highly variable delay of approximately 12 h between onset of iPAK4 transcription and assembly nucleation, and (b) the assemblies undergo a period of fast and nonlinear growth during the first~hour after nucleation (FIG. 1E). On the other hand, to ensure that most cells only contain a single assembly, one wants $C_{nuc}/C_{SS}>1$. Thus, this ratio should be slightly larger than 1.

Cultured neurons could sustain iPAK4 assembly growth for at least 6 days (FIGS. 19A-19B), suggesting the possibility of multi-day recordings. To tune the dynamic range of ticker tape recordings, one would like small-molecule or light-induced control over the onset and rate of ticker tape scaffold growth. Putting the iPAK4 scaffold under control of the Tet-ON system gave control over the onset of assembly growth (FIGS. 17A-17C).

A further modification would be to have pharmacological regulation of the soluble iPAK4 expression level, either by regulation of transcription[30] or of protein stability[31], to permit tuning of the temporal dynamic range. A means to trigger assembly nucleation at a defined time could also be included, and a means to have the steady-state monomer concentration only slightly lower than the nucleation concentration so that the period of initial rapid growth is minimized. Another alternative within the scope of the present disclosure is to express both the iPAK4 and the HT-iPAK4 from a single vector, either by making use of endogenous RNA splicing machinery or by applying a partially effective self-cleaving peptide.

Ubiquitination domains or other tags may also be attached to HT-iPAK4 to shorten their half-life and facilitate proteolytic turnover of the soluble subunits.[32] Alternatively, a variety of optogenetic caging strategies (as described in Example 2) may be used to reversibly control the availability of time-stamp monomers.[33] Optogenetic modulation of protein availability can occur over seconds, suggesting the possibility to introduce extremely precise fiducial time stamps.

Finally, the modular design of iPAK4 assemblies could also accommodate diverse recording modalities. A simple generalization of the present results would be to record the simultaneous dynamics of multiple promoters by using each to drive expression of iPAK4 fused to a spectrally distinct fluorescent protein. There also exist diverse fluorescent reporters of covalent enzymatic modifications, e.g., of kinase, phosphatase, or protease activity (as described in Example 3).[34,35] Such reporters are likely protected from enzymatic modification within the protein assembly, and thereby might be a means to record the state of the cell at the moment of incorporation into the assembly. The methods described herein can also be used to map transcriptional dynamics during stem cell differentiation, in in vitro tumor models, or in diverse organoid models.

Methods

Cloning and molecular biology: All iPAK4 constructs were cloned into a second-generation lentiviral backbone (Addgene:136636) with either a CMV or a cFos promoter (Addgene: 47907) using standard GibsonAssembly.[36] Briefly, the vector was linearized by double digestion (BamH1 and EcoR1 for CMV driven constructs, Pac1 and EcoR1 for cFos driven constructs) and purified by the GENEJET™ gel extraction kit (ThermoFisher). Gene fragments and cFos promoter were generated by PCR amplification and then combined with the linearized backbones by Gibson ligation. HALOTAG® ligand was cloned from pCAG-Voltron (Addgene: 119033). The eGFP and iPAK4 were connected with a SGGS linker, while the HALOTAG® and iPAK4 were connected with a SGS linker. All plasmids were verified by full sequencing around the cloned regions.

| Plasmid ID | Description | Addgene ID |
|---|---|---|
| DL015: CMV::iPAK4 | ibox-PAK4cat (iPAK4) fusion with CMV promoter, cloned into a lentivirus backbone | 177880 |
| DL016: CMV::eGFP-iPAK4 | eGFP-IPAK4 fusion with CMV promoter, cloned into a lentivirus backbone | 177881 |
| DL017: CMV::HaloTag-iPAK4 | HT-iPAK4 fusion with CMV promoter, cloned into a lentivirus backbone | 177882 |
| DL033: cFos::eGFP-iPAK4 | eGFP-iPAK4 fusion with cFos promoter, cloned into a lentivirus backbone | 177883 |
| DL034: cFos::HaloTag-iPAK4 | HaloTag-iPAK4 fusion with cFos promoter, cloned into a lentivirus backbone | 177884 |

Synthesis of $JFX_{608}$-HALOTAG®

General synthetic methods. Commercial reagents were obtained from reputable suppliers and used as received. All solvents were purchased in septum-sealed bottles stored under an inert atmosphere. All reactions were sealed with septa through which a nitrogen atmosphere was introduced unless otherwise noted. Reactions were conducted in round-bottomed flasks or septum-capped crimp-top vials containing TEFLON®-coated magnetic stir bars. Heating of reactions was accomplished with a silicon oil bath or an aluminum reaction block on top of a stirring hotplate equipped with an electronic contact thermometer to maintain the indicated temperatures. Reactions were monitored by thin layer chromatography (TLC) on precoated TLC glass plates (silica gel 60 $F_{254}$, 250 μm thickness) or by LC/MS (Phenomenex Kinetex 2.1 mm×30 mm 2.6 μm C18 column; 5 μL injection; 5-98% $MeCN/H_2O$, linear gradient, with constant 0.1% v/v $HCO_2H$ additive; 6 min run; 0.5 mL/min flow; ESI; positive ion mode). TLC chromatograms were visualized by UV illumination or developed with p-anisaldehyde, ceric ammonium molybdate, or $KMnO_4$ stain. Reaction products were purified by flash chromatography on an automated purification system using pre-packed silica gel columns or by preparative HPLC (Phenomenex Gemini-NX 30×150 mm 5 μm C18 column). Analytical HPLC analysis was performed with an Agilent Eclipse XDB 4.6×150 mm 5 μm C18 column under the indicated conditions. High-resolution mass spectrometry was performed by the High Resolution Mass Spectrometry Facility at the University of Iowa. NMR spectra were recorded on a 400 MHz spectrometer. $^1H$ and $^{13}C$ chemical shifts were referenced to TMS or residual solvent peaks. Data for $^1H$ NMR spectra are reported as follows: chemical shift (δ ppm), multiplicity (s=singlet, d=doublet, t=triplet, q=quartet, dd=doublet of doublets, m=multiplet), coupling constant (Hz), integration. Data for $^{13}C$ NMR spectra are reported by chemical shift (δ ppm) with hydrogen multiplicity (C, CH, $CH_2$, $CH_3$) information obtained from DEPT spectra.

6-tert-Butoxycarbonyl-$JFX_{608}$ (2). A vial was charged with 6-tert-butoxycarbonyl-carbofluorescein ditriflate[18] (1; 250 mg, 0.346 mmol), $Pd_2dba_3$ (31.7 mg, 34.6 mol, 0.1 eq), XPhos (49.5 mg, 0.104 mmol, 0.3 eq), and $Cs_2CO_3$ (316 mg, 0.969 mmol, 2.8 eq). The vial was sealed and evacuated/backfilled with nitrogen (3×). Dioxane (2 mL) was added, and the reaction was flushed again with nitrogen (3×). Following the addition of azetidine-2,2,3,3,4,4-$d_6$ (52.4 mg, 0.830 mmol, 2.4 eq), the reaction was stirred at 100° C. for 4 h. It was subsequently cooled to room temperature, filtered through Celite with $CH_2Cl_2$, and concentrated to dryness. Purification by silica gel chromatography (20-100% EtOAc/hexanes, linear gradient) afforded 6-tert-butoxycarbonyl-$JFX_{608}$ (2) as a blue-green solid (181 mg, 95%). $^1H$ NMR ($CDCl_3$, 400 MHz) δ 8.14 (dd, J=8.0, 1.3 Hz, 1H), 8.00 (dd, J=8.0, 0.8 Hz, 1H), 7.62 (dd, J=1.2, 0.7 Hz, 1H), 6.58 (d, J=2.4 Hz, 2H), 6.54 (d, J=8.6 Hz, 2H), 6.21 (dd, J=8.6, 2.3 Hz, 2H), 1.83 (s, 3H), 1.73 (s, 3H), 1.53 (s, 9H); $^{13}C$ NMR ($CDCl_3$, 101 MHz) δ 170.2 (C), 164.6 (C), 155.6 (C), 152.5 (C), 146.8 (C), 137.8 (C), 130.3 (C), 130.1 (CH), 128.9 (CH), 125.1 (CH), 124.8 (CH), 119.8 (C), 110.5 (CH), 108.0 (CH), 88.8 (C), 82.3 (C), 38.5 (C), 35.5 ($CH_3$), 32.8 ($CH_3$), 28.2 ($CH_3$); Analytical HPLC: $t_R$=13.3 min, >99% purity (10-95% $MeCN/H_2O$, linear gradient, with constant 0.1% v/v TFA additive; 20 min run; 1 mL/min flow; ESI; positive ion mode; detection at 600 nm); HRMS (ESI) calcd for $C_{34}H_{25}D_{12}N_2O_4$ $[M+H]^+$ 549.3501, found 549.3503.

6-Carboxy-$JFX_{608}$(3). 6-tert-Butoxycarbonyl-$JFX_{608}$ (2; 310 mg, 0.565 mmol) was taken up in $CH_2Cl_2$ (10 mL), and trifluoroacetic acid (2 mL) was added. The reaction was stirred at room temperature for 6 h. Toluene (10 mL) was added; the reaction mixture was concentrated to dryness and then azeotroped with MeOH three times to provide 6-carboxy-$JFX_{608}$ (3) as a dark blue solid (323 mg, 94%, TFA salt). Analytical HPLC and NMR indicated that the material was >95% pure and did not require further purification prior to amide coupling. $^1H$ NMR ($CD_3OD$, 400 MHz) δ 8.36-8.27 (m, 2H), 7.86-7.78 (m, 1H), 6.91 (d, J=9.1 Hz, 2H), 6.81 (d, J=2.3 Hz, 2H), 6.38 (dd, J=9.1, 2.3 Hz, 2H), 1.82 (s, 3H), 1.70 (s, 3H); $^{13}C$ NMR ($CD_3OD$, 101 MHz) δ 168.0 (C), 167.5 (C), 158.0 (C), 157.0 (C), 139.5 (C), 137.6 (CH), 136.2 (C), 135.5 (C), 132.4 (CH), 132.3 (CH), 131.4 (CH), 121.8 (C), 111.9 (CH), 109.7 (CH), 42.8 (C), 35.6 ($CH_3$), 32.0 ($CH_3$); Analytical HPLC: $t_R$=10.5 min, >99% purity (10-95% $MeCN/H_2O$, linear gradient, with constant 0.1% v/v TFA additive; 20 min run; 1 mL/min flow; ESI; positive ion mode; detection at 600 nm); HRMS (ESI) calcd for $C_{30}H_{17}D_{12}N_2O_4$ $[M+H]^+$ 493.2875, found 493.2873.

$JFX_{608}$-NHS (4). 6-Carboxy-$JFX_{608}$ (3, TFA salt; 125 mg, 0.206 mmol) was combined with DSC (116 mg, 0.453 mmol, 2.2 eq) in DMF (5 mL). After adding $Et_3N$ (172 μL, 1.24 mmol, 6 eq) and DMAP (2.5 mg, 20.6 mol, 0.1 eq), the reaction was stirred at room temperature for 30 min. It was subsequently diluted with 10% w/v citric acid and extracted with EtOAc (2×). The combined organic extracts were washed with water and brine, dried over anhydrous $MgSO_4$, filtered, and concentrated in vacuo. Flash chromatography (25-100% $EtOAc/CH_2Cl_2$, linear gradient) yielded 116 mg (95%) of $JFX_{608}$-NHS (4) as a dark blue-green solid. $^1H$ NMR ($CDCl_3$, 400 MHz) δ 8.30 (dd, J=8.0, 1.4 Hz, 1H), 8.11 (dd, J=8.0, 0.8 Hz, 1H), 7.78 (dd, J=1.4, 0.7 Hz, 1H), 6.57 (d, J=2.4 Hz, 2H), 6.50 (d, J=8.6 Hz, 2H), 6.23 (dd, J=8.5, 2.4 Hz, 2H), 2.87 (s, 4H), 1.83 (s, 3H), 1.71 (s, 3H); Analytical HPLC: $t_R$=11.1 min, >99% purity (10-95% MeCN/$H_2O$, linear gradient, with constant 0.1% v/v TFA additive; 20 min run; 1 mL/min flow; ESI; positive ion mode; detection at 600 nm); HRMS (ESI) calcd for $C_{34}H_{20}D_{12}N_3O_6$ $[M+H]^+$ 590.3039, found 590.3043.

$JFX_{608}$-HALOTAG® ligand (6). $JFX_{608}$-NHS (4; 50 mg, 84.8 mol) and 2-(2-((6-chlorohexyl)oxy)ethoxy)ethanamine (5, "HALOTAG® (02)amine," TFA salt; 43.0 mg, 0.127 mmol, 1.5 eq) were combined in DMF (3 mL), and DIEA (44.3 µL, 0.254 mmol, 3 eq) was added. After stirring the reaction at room temperature for 1 h, it was diluted with saturated $NaHCO_3$ and extracted with EtOAc (2×). The combined organic extracts were washed with water and brine, dried over anhydrous $MgSO_4$, filtered, and concentrated in vacuo. Purification of the crude product by silica gel chromatography (50-100% EtOAc/toluene, linear gradient) provided $JFX_{608}$-HALOTAG® ligand (6) as a blue foam (47 mg, 79%). $^1$H NMR ($CDCl_3$, 400 MHz) δ 8.02 (dd, J=8.0, 0.7 Hz, 1H), 7.94 (dd, J=7.9, 1.4 Hz, 1H), 7.44-7.39 (m, 1H), 6.73 (t, J=4.8 Hz, 1H), 6.57 (d, J=2.4 Hz, 2H), 6.52 (d, J=8.6 Hz, 2H), 6.20 (dd, J=8.6, 2.4 Hz, 2H), 3.64-3.56 (m, 6H), 3.54-3.48 (m, 4H), 3.38 (t, J=6.6 Hz, 2H), 1.83 (s, 3H), 1.78-1.73 (m, 2H), 1.72 (s, 3H), 1.55-1.48 (m, 2H), 1.45-1.38 (m, 2H), 1.34-1.27 (m, 2H); Analytical HPLC: $t_R$=12.6 min, >99% purity (10-95% MeCN/$H_2O$, linear gradient, with constant 0.1% v/v TFA additive; 20 min run; 1 mL/min flow; ESI; positive ion mode; detection at 600 nm); HRMS (ESI) calcd for $C_{40}H_{37}D_{12}ClN_3O_5$ $[M+H]^+$ 698.4108, found 698.4118.

Assembly expression in HEK cells: HEK293T cells (ATCC; CRL-11268) were grown and split following standard protocols as described previously.[37] HEK293T cells at low-passage-number (<10 passages) were plated at a confluence of 30% onto 10-cm dishes coated with gelatin (Stemcell Technologies; 07903) or 14 mm glass bottom dishes (CellVis, D35-14-1.5-N) coated with 40 µg/ml poly-L-lysine-coated (P8920, Sigma-Aldrich). Dulbecco's modified Eagle's medium (DMEM) supplemented with 10% FBS and penicillin/streptomycin was used as the culture medium. Cells were grown at 37° C. and 5% $CO_2$.

When cells reached 50-70% confluence, genes were delivered by either lentivirus or TRANSIT®-293 (Mirus; MIR2700) transfection kit. In lentiviral transduction, the high-titer lentiviral vectors were first pre-mixed at the designated ratio and diluted to 10% of the initial concentration by DMEM medium. The cells' culture medium was then replaced by the fresh lentivirus-containing DMEM medium, and the cells were further incubated at 37° C. and 5% $CO_2$ for ~24 h. In the TRANSIT®-293 transfection, 1 µg plasmids at the designated ratio were first diluted by 100 µl OPTI-MEM® medium, followed by the addition of 3 µl TRANSIT®-293 reagent. The cocktail was incubated at room temperature for 15 min and diluted 10-fold into DMEM on the culture dishes. The cells were then further incubated at 37° C. and 5% $CO_2$ for ~24 h.

Assembly labeling: The in-cellulo assemblies were labeled with HALOTAG® ligand-conjugated Janelia Fluor (JF) dyes. The cell-permeable dyes used were: $JF_{503}$, $JF_{525}$, $JF_{552}$, $JFX_{608}$, and $JF_{669}$. The JF dyes were first diluted into 1 mM stock solution as described previously,[17] which was aliquoted and stored at −20° C. The 1 mM solution was further diluted to 1 µM in 37° C. DMEM medium for HEK cells or BPNM/SM1 medium for neurons. The dyed medium was used to replace the original medium in the culture dishes at timed staining. In the dye switching processes, the medium containing the original dye was fully removed, followed by thorough wash of the culture dishes 5 times with 37° C. culture medium. Then, the medium with 1 µM new dye was added to the cells, and the cells were returned to the incubator at 37° C. and 5% $CO_2$.

Measurements of HT dye labeling kinetics in HEK293T cells: HEK293T cells were transfected with an inducible nuclear-localized HT protein (HT-NLS, Addgene #82518). Doxycycline (DOX, 2 µg/ml) was added 12 h after transfection to induce the expression of HT-NLS. 24 h after transfection, cells were incubated with 0.1 µM of the indicated dye, and nuclear fluorescence was monitored via wide-field epifluorescence microscopy as a function of time.

Primary neuron culture: Before the plating of primary hippocampal neurons, 14 mm glass-bottom dishes were first incubated with 40 µg/ml poly-D-lysine (PDL) in PBS at room temperature for 1 h and subsequentially with 20 µg/ml laminin (Fisher Scientific; 23-017-015) at 4° C. overnight, followed by thorough wash with PBS. Hippocampi (BrainBits; SKU: SDEHP) from embryonic day 18 (E18) rats were dissected and resuspended in Brainphys™ medium (BPNM, Stemcell Technologies; 05790) supplemented with 2% SM1 (Stemcell Technologies; 05792), 5 mM L-Glutamine (Stemcell Technologies; 07100), and 35 µg/ml L-Glutamic Acid (Sigma Aldrich; 49449), to a final concentration of $3.0\times10^6$ cells/ml. The neurons were then plated at a density of 30,000 cells/$cm^2$ on the pretreated glass-bottom dishes, with subsequent addition of 2 ml BPNM with 2% SM1 (BPNM/SM1). Neuronal health was monitored daily from DIV1 to DIV7. Every 3-4 days, 1 ml of the medium in each dish was replaced with 37° C. fresh BPNM/SM1 medium.

Patch clamp electrophysiology: Whole-cell recordings were performed in extracellular buffer containing (in mM): 125 NaCl, 2.5 KCl, 15 HEPES, 25 D-glucose, 1 $MgCl_2$, and 2 $CaCl_2$) (pH=7.2-7.3 with NaOH). Assembly-forming and non-forming (control) neurons were visualized with a home-built inverted epifluorescence microscope. Experiments were made at 23° C. under ambient atmosphere. The whole-cell internal solution comprised (in mM): 8 NaCl, 130 $KMeSO_3$, 10 HEPES, 5 KCl, 0.5 EGTA, 4 Mg-ATP, and 0.3 $Na_3$-GTP. The pH was adjusted to 7.2-7.3 with KOH and osmolarity was set to 290-295 mOsm/L. Borosilicate glass pipettes were used with a resistance of 3-5 MΩ (1.5 mm OD). Signals were acquired and filtered at 4 kHz with the internal Bessel filter using a Multiclamp 700B (Molecular Devices) and digitized with PCIe-6323 (National Instruments) at 10 kHz. Following the whole-cell configuration, membrane capacitance (Cm), and membrane resistance (Rm) were estimated under voltage-clamp mode. Measurements of resting membrane potential (Vrest), rheobase, and spike rates were made under current-clamp mode. Rheobase was defined as the minimum current step (in 500 ms duration) required for any spike onset. Whole-cell recordings were monitored and analyzed using a custom code written in LabView and Matlab.

Lentivirus production in HEK293T cells: Plasmids of CMV::iPAK4, CMV:: HALOTAG®-iPAK4, and cFos:: eGFP-iPAK4 were used to produce lentivirus according to published methods.[38] Briefly, low passage-number HEK293T cells (ATCC; CRL-11268) were plated onto gelatin-coated (Stemcell Technologies; 07903) 10-cm dishes. When HEK cells reached 80% confluence, the medium was exchanged to a serum-free DMEM. After 0.5-1 h, cells were transfected using polyethylenimine (PEI; Sigma; 408727). 7 µg of the vector plasmid, 4 µg of the second-generation packaging plasmid psPAX2 (Addgene; 12260), and 2 µg of viral entry protein VSV-G plasmid pMD2.G (Addgene; 12259) were mixed into 600 μl of serum-free DMEM, and 20 μl of 1 mg/ml PEI was then added. The mixture was incubated at room temperature for 15 min and added drop-wise to the plate. After 3-4 h, the medium was exchanged back to 10 ml of DMEM10. The supernatant was harvested at 36 h post-transfection, and another 10 ml of DMEM10 was added to the cells and incubated for another 24 h. At 60 h post-transfection, the supernatant was harvested again and combined with the first batch of supernatant, centrifuged for 5 min at 500 g, and filtered through a 0.45-μm filter (EMD Millipore; SE1M003M00).

Lentivirus concentration: 1 part of *Lenti*-X™ concentrator (TaKaRa; 631232) was first mixed with 3 parts of supernatant and incubated at 4° C. overnight for lentivirus precipitation. The mixture was then centrifuged at 1,500×g for 45 min at 4° C. The supernatant was gently removed, and the off-white pellet was resuspended in 200 μl neurobasal-based medium. The concentrated virus was titrated in neurons, aliquoted, and stored at −80° C. for neuronal transduction.

Assembly expression in neurons: Genes were delivered to neurons by lentiviral transduction at DIV 7-10. The lentiviral vectors of CMV::iPAK4, CMV:: HALOTAG®-iPAK4, and cFos::eGFP-iPAK4 were first mixed at the designated ratio, which was further diluted to 10% of the original concentration by fresh BPNM/SM1 medium. The dilution was then used to replace the original medium in neuronal culture. The neurons were incubated in the lentivirus-containing medium at 37° C. and 5% $CO_2$ for 12 h, followed by medium replacement with lentivirus-free medium.

Chemical activation of neuronal activity: The cFos promoter was activated by phorbol 12-myristate 13-acetate (PMA; Sigma Aldrich P8139). Briefly, the PMA was first diluted with DMSO to form a 1 mM stock solution. At the designated time, 2 μl PMA stock was directly added to each 14 mm glass-bottom culture dish, which contained 2 ml BPNM/SM1 medium. The dishes were then stirred gently to mix the PMA and medium. After PMA addition, the dishes were returned to an incubator at 37° C. with 5% $CO_2$.

Multispectral imaging: Multispectral images were acquired using ZEISS LSM 980 confocal microscope with Airyscan 2. Lambda scan mode was used to image assemblies with multi-color labeling. The excitation laser wavelengths were 488 nm (eGFP, $JF_{503}$, $JF_{525}$), 561 nm ($JF_{552}$, $JFX_{608}$), and 639 nm ($JF_{669}$). In each Lambda scan, 32 channels in the range of 414-688 nm were simultaneously acquired to obtain a hyperspectral stack of images. The images were then unmixed with the built-in linear unmixing algorithm in Zen Blue software. Reference images of individual fluorescent labels were taken in the same instrumental configuration to train the linear unmixing algorithm. The spectral unmixing typically produced negligible residual signals.

Time-lapse microscopy: HEK293T cells expressing the target constructs were grown on 14 mm glass bottom culture dishes (CellVis, D35-14-1.5-N) and were monitored under a Zeiss Elyra microscope with 488 nm laser and a 10× air objective in an environmental chamber at 37° C. and 5% $CO_2$. Images were acquired at 1% laser power, 300 ms exposures, 10 min intervals over 10-23 hours post-transfection.

Figure 7A:
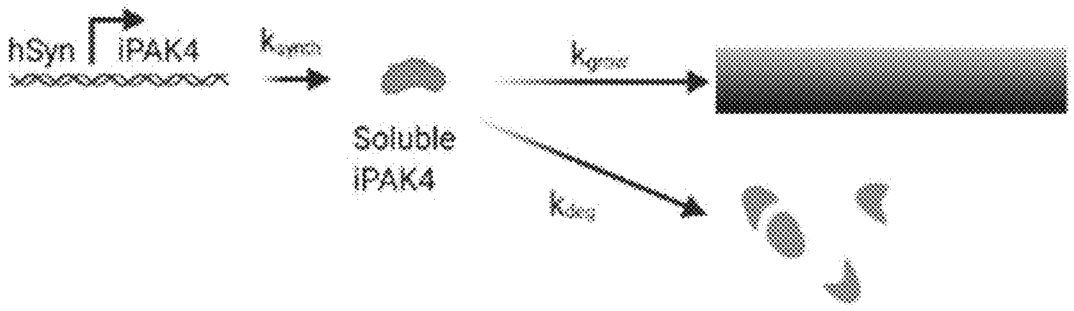
FIGS. 7A-7E show model of iPAK4 assembly growth. Related to FIG. 1A, FIG. 7A provides a kinetic scheme for assembly growth, comprising transcription and translation (here modeled as a single step), protein degradation, and incorporation into the assembly. Assembly nucleation is assumed to occur at a critical concentration, $C_{nuc}$. Monomer incorporation into the assembly is assumed to follow first-order kinetics in monomer concentration.
Figure 7B:
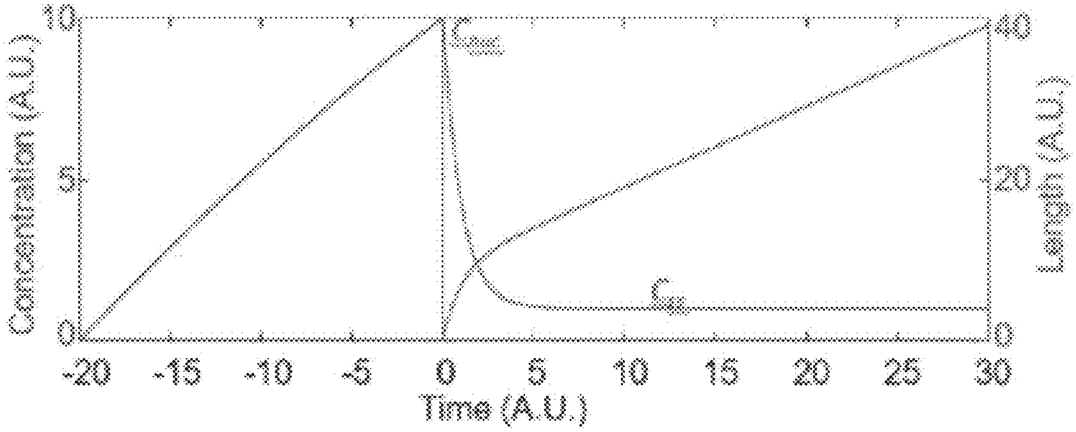
Figure 7C:
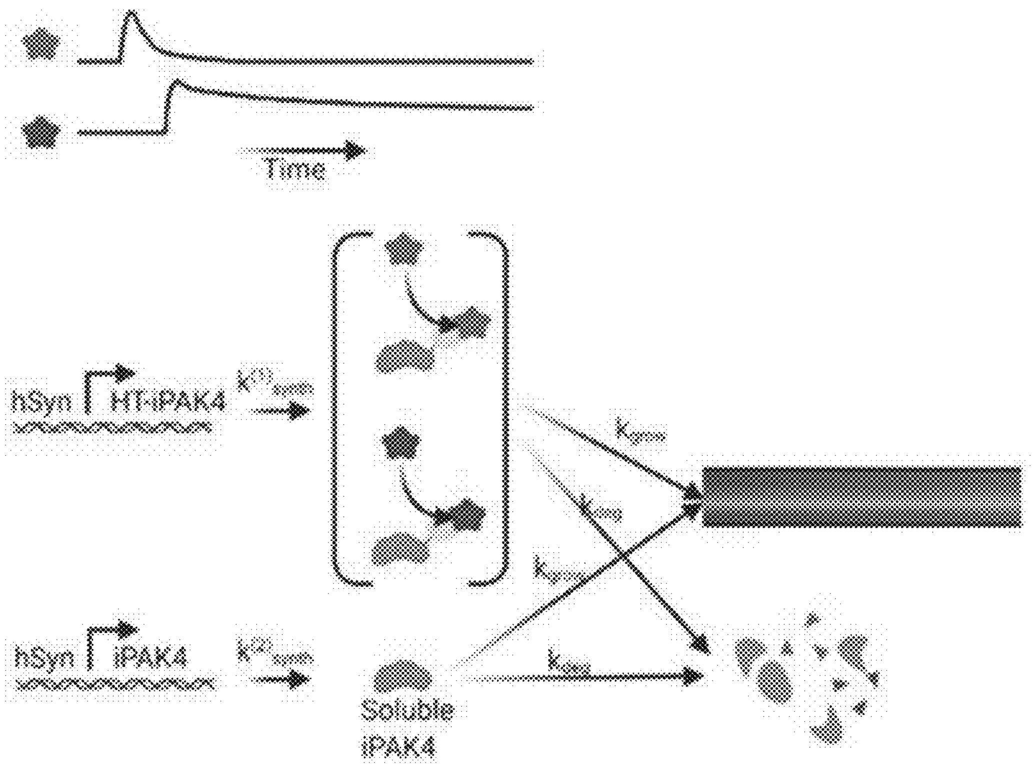
Figure 7D:
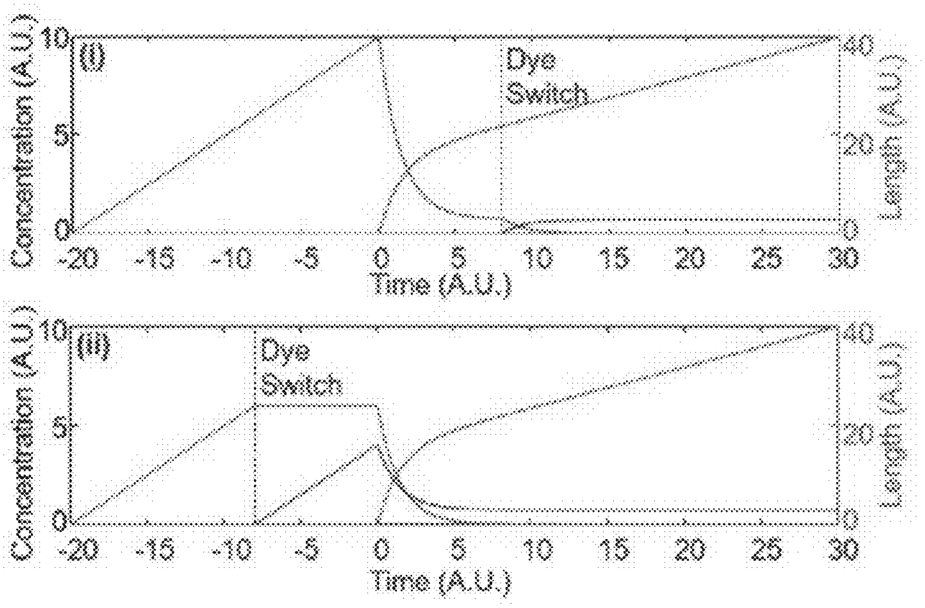
Figure 7E:
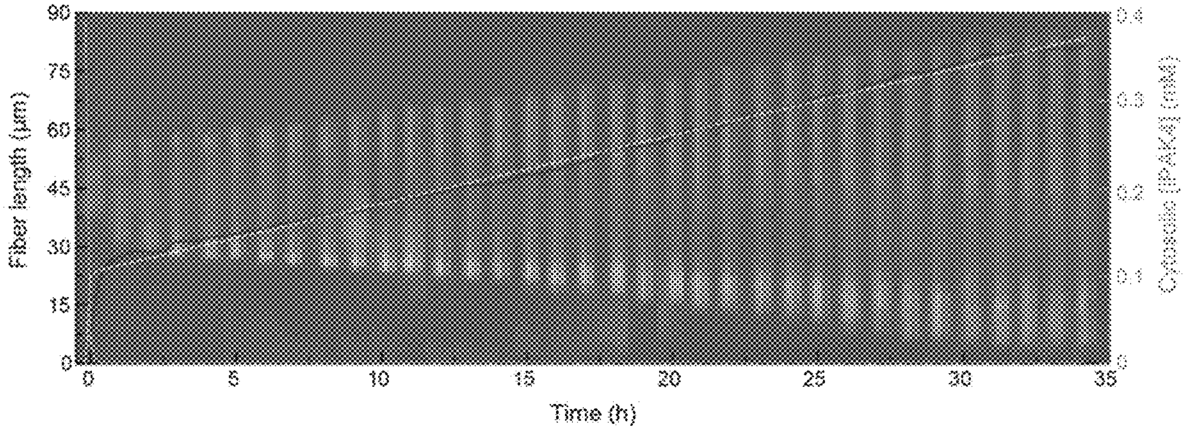
Figure 8A:
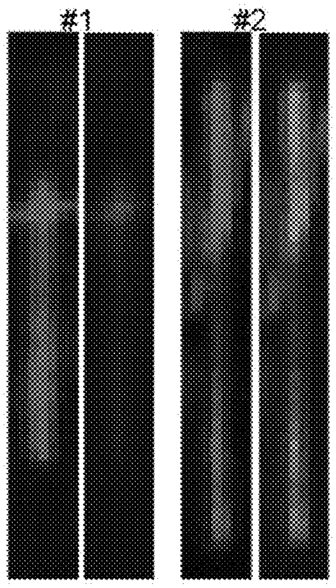
FIGS. 8A-8D show that fluorescent tags do not affect iPAK4 assembly growth rate. Related to FIG. 1A.
Figure 8B:
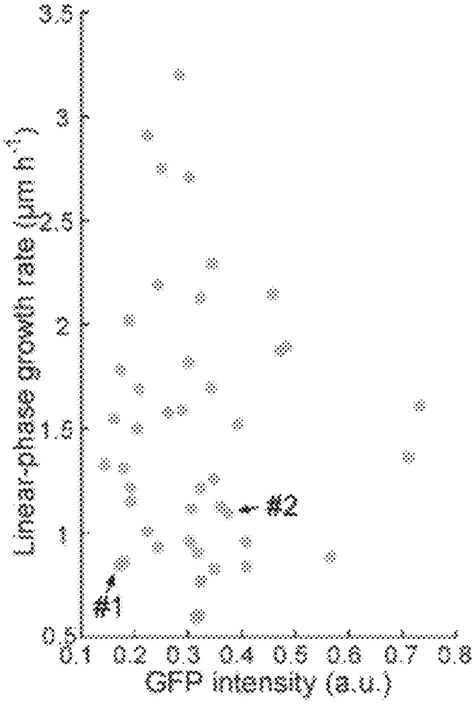
Figure 8C:
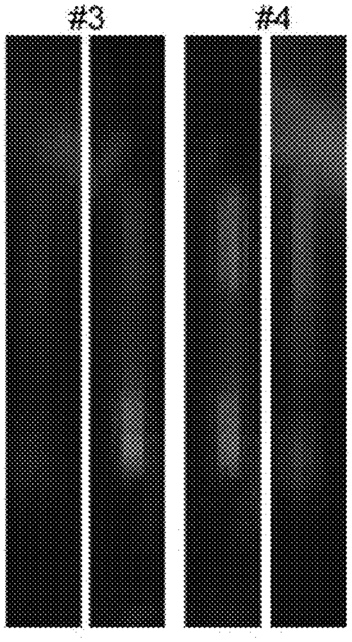
Figure 8D:
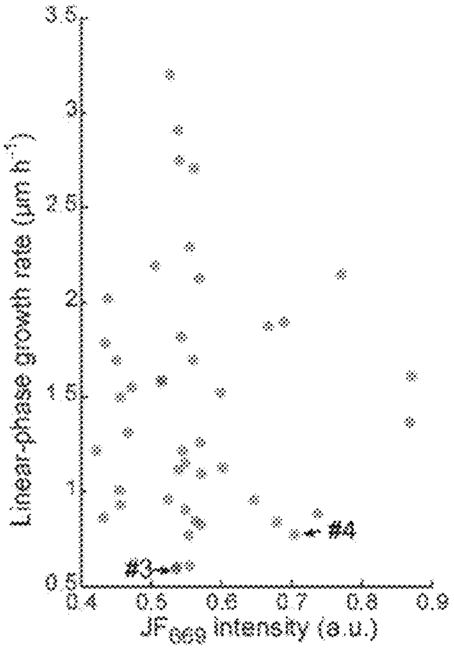
Figure 9A:
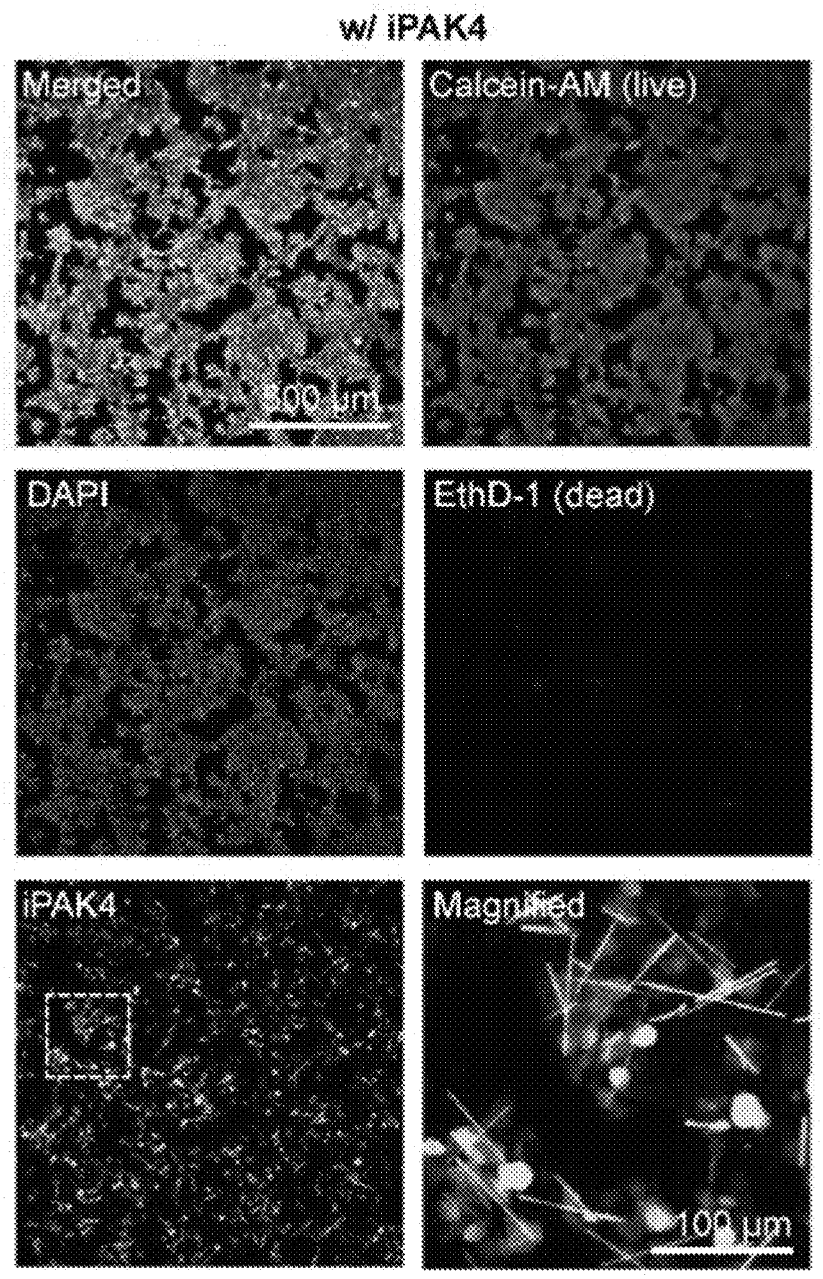
FIGS. 9A-9C show a live-dead assay to assess the effect of iPAK4 assemblies on cell health. Related to FIG. 1A, FIG. 9A provides images of HEK293T cells expressing CMV::iPAK4 (95%) and CMV::HT-iPAK4 (5%). Many iPAK4 assemblies can be identified in a magnified view.
Figure 9B:
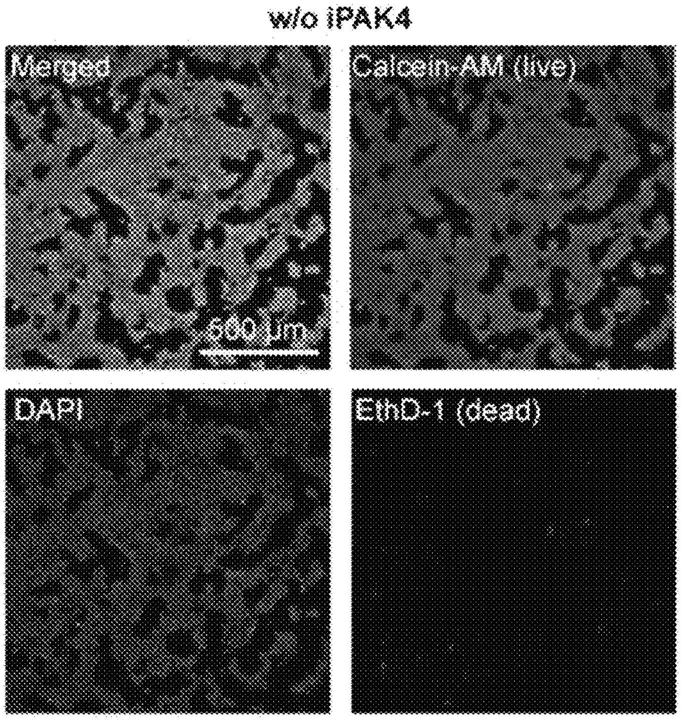
Figure 9C:
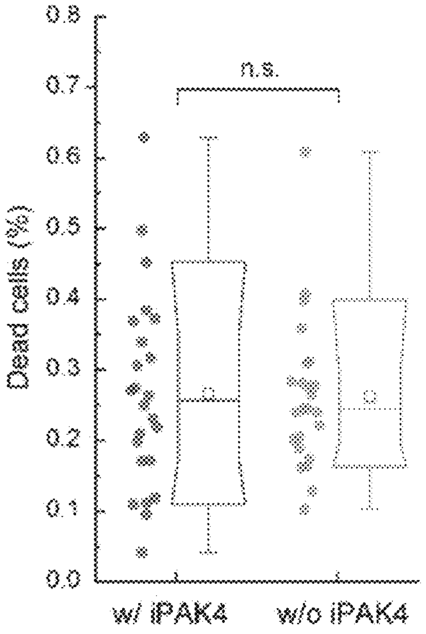
Figure 10A:
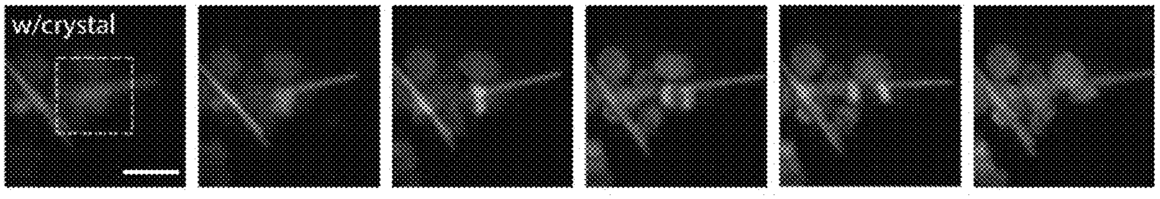
FIGS. 10A-10D show mitosis in HEK293T cells containing iPAK4 assemblies. Related to FIG. 1, in all cases, DNA was stained with Hoechst 33342.
Figure 10B:
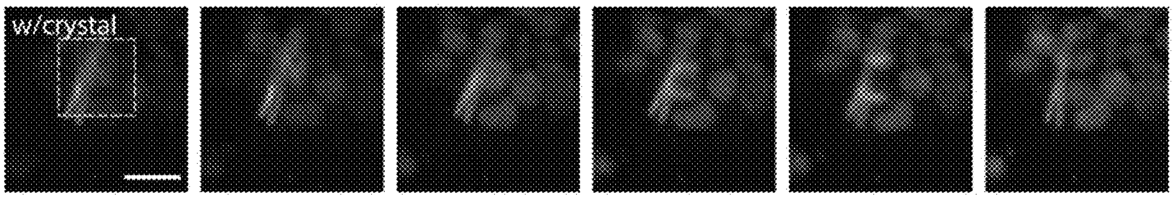
Figure 10C:
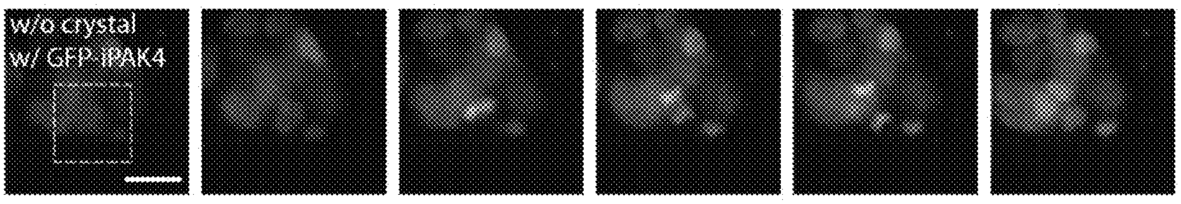
Figure 10D:
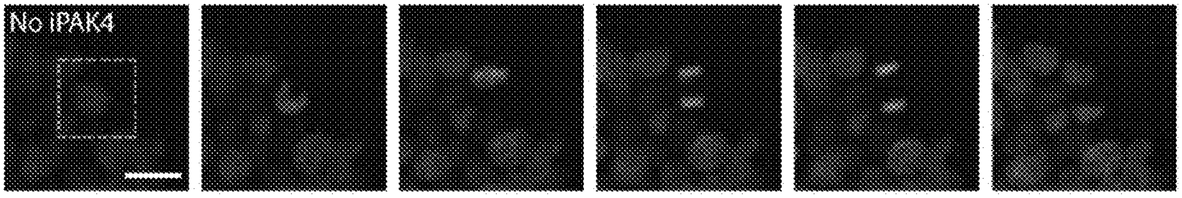

Image processing and data analysis: Images of individual assemblies were rotated to align the long axis to the x-axis. Fluorescence profiles were then calculated as the median fluorescence in each spectral channel across the width of the assembly. Assemblies that were not in focus or where two or more assemblies crossed each other near a dye transition were excluded from analysis. Dye transitions were identified as local maxima in the second derivative of the dye fluorescence as a function of position. To avoid spurious peaks due to noise, the second derivative signal was smoothed with a kernel of typically 10 min, though this smoothing was omitted when calculating the width of the dye transition (FIG. 7A).

For tracking assemblies during time-lapse recordings, a region of interest (ROI) was manually defined on a maximum intensity projection of the image stack, to select individual assemblies and to encompass the entire assembly in all frames of the movie. A Radon transform was then calculated on the selected ROI for each video frame. The peak of the Radon transform was associated with the assembly. The corresponding line in the real-space movie was used to calculate the assembly intensity profile. Nearby parallel lines on either side of the assembly were averaged and used for background subtraction. The assembly ends were then found by applying a simple threshold to the plot of fluorescence vs. position. The fluorescence of the cytoplasm was determined by summing the intensity from pixels that were on-cell but off-assembly. Assembly length trajectories were median filtered (kernel=1 hr) to suppress small, high-frequency fluctuations caused by segmented noise.

Calculation 1—Kinetics of iPAK4 assembly growth: First, the relation between the concentration, C, of soluble iPAK4 monomers and the rate of change of the length, L, of an assembly was examined. The cross-sectional area is A ($\mu m^2$), the density of molecules in the assembly is r (molecules/$\mu m^3$), the surface density of molecules along the growing tip is a (molecules/$\mu m^2$), and the linear density along the growth direction is 1 (molecules/μm).

Hence r=a 1.

Based on the published crystal structure (PDB:4XBR), the volume of the unit cell is $1.12\times10^6$ $Å^3$ and contains 6 iPAK4 monomers. This corresponds to a monomer density $r=5.36\times10^6$ molecules/$\mu m^3$, or equivalently a monomer concentration in the assembly of 8.9 mM.

Steady state assembly growth. The rate of growth of the assembly is related to the rate of decrease of the number of monomers, n, from the cytoplasm by:

$$\frac{dn}{dt} = -A\rho\frac{dL}{dt}, \qquad [1]$$

Implying that the rate of change of soluble monomer concentration due to assembly growth is:

$$\frac{dC}{dt} = -\frac{A}{V}\rho\frac{dL}{dt}, \qquad [2]$$

where V is the volume of the cytoplasm. For example, growth of an assembly with a diameter d=2 μm at a rate of 1 μm/hr corresponds to incorporation of 4,700 monomers/s. For a cell with a volume of 5 pL, this corresponds to a decrease in soluble monomer concentration (in the absence of replenishment by protein synthesis) of 1.6 nM/s. It can be further assumed that the off-rate of monomers from the assembly is negligible, and that the assembly grows via addition across its entire face. Then the rate of growth of the assembly is:

$$\frac{dL}{dt} = \frac{C}{\lambda}k_{grow}, \qquad [3]$$

where $k_{grow}$ ($M^{-1}$ $s^{-1}$) is the first-order rate constant for monomer addition to the assembly. If protein synthesis at rate $k_{synth}$ (moles/s) and degradation of soluble proteins at rate $k_{deg}$ ($s^{-1}$) is included, and Eq. 3 is inserted into Eq. 2, the following is obtained:

$$\frac{dC}{dt} = \frac{k_{synth}}{V} - k_{deg}C - \frac{A\alpha}{V}Ck_{grow}, \tag{4}$$

Under steady-state conditions $$\left(\frac{dC}{dt} = 0\right),$$

the concentration is $$C_{ss} = \frac{k_{synth}}{Vk_{deg} + A\alpha k_{grow}}, \tag{5}$$

and the growth rate is $$\frac{dL_{ss}}{dt} = \frac{k_{synth}k_{grow}}{V\lambda k_{deg} + A\rho k_{grow}}. \tag{6}$$

Thus at long times, the growth is linear, and the rate is set by the balance of protein synthesis and protein removal from the cytoplasm, either by degradation or incorporation into the assembly.

Time-dependent growth profile. For further analysis, it is assumed that incorporation into the assembly is the only path for removing soluble proteins, i.e., protein degradation is negligible ($k_{deg}\approx 0$). Then $$C_{ss} = \frac{k_{synth}}{A\alpha k_{grow}}.$$

It is assumed that assembly nucleation occurs once the soluble concentration reaches a threshold, $C_{nuc}$. Then, one can solve explicitly for the time-dependent soluble concentration:

$$C(t) = (C_{nuc} - C_{ss})e^{-\frac{A\alpha k_{grow}}{V}t} + C_{ss},$$

and the time-dependent assembly length:

$$L(t) = \frac{k_{grow}}{\lambda}C_{ss}t + \frac{V}{A\rho}(C_{nuc} - C_{ss})\left(1 - e^{-\frac{A\alpha k_{grow}}{V}t}\right), \tag{7a}$$

which can also be written as:

$$L(t) = \frac{k_{synth}}{A\rho}t + \frac{V}{A\rho}(C_{nuc} - C_{ss})\left(1 - e^{-\frac{A\alpha k_{grow}}{V}t}\right). \tag{7b}$$

Eqs. 7a and 7b show that assembly growth has two phases. Initially, there is rapid growth driven by the excess soluble monomers in the cytoplasm. Once the cytoplasmic concentration has decreased, the assembly settles into a linear growth mode.

Multi-color labeling. Multi-color labeling of a growing assembly was considered next. Consider the case of two HALOTAG® dyes, R (red) and G (green), each of which follows a time-dependent intracellular concentration, R(t) and G(t), respectively. These profiles are not fully under user control, particularly in vivo. A user can specify how much dye is added, and when; but the free dye concentrations in the cytoplasm depend on dye pharmacokinetics: permeation across the cell membrane, metabolism, and excretion in vivo. These processes are not explicitly simulated here, but it is instead assumed that R(t) and G(t) are known.

It was further assumed that the HALOTAG® reactions are fast compared to all the other dynamics in the system. This assumption is valid for dye concentrations in the μM range, typical of HALOTAG® experiments in vivo. Finally, it was assumed that the labeling reaction rate constants are the same for the two dyes. If these rate constants differ, the concentrations of the dyes should be replaced by their specific activities.

Under these assumptions, the concentrations of soluble monomers labeled with each color of dye follow the mole fractions of the dyes at the time of protein translation:

$$\frac{dC_R}{dt} = \frac{k_{synth}^{HT}}{V}\frac{R(t)}{R(t)+G(t)} - \frac{k_{deg}^{HT}}{V}C_R - \frac{A\alpha}{V}k_{grow}C_R,$$
$$\frac{dC_G}{dt} = \frac{k_{synth}^{HT}}{V}\frac{G(f)}{R(t)+G(t)} - \frac{k_{deg}^{HT}}{V}C_G - \frac{A\alpha}{V}k_{grow}C_G. \tag{8}$$

Here the HT superscripts indicate that the parameters are for the HALOTAG®-labeled iPAK4 monomers. It is assumed that the labeled and unlabeled iPAK4 monomers incorporate into the assembly with the same rate constant, $k_{grow}$.

Both labeled and unlabeled monomers contribute to the growth of the assembly:

$$\frac{dL}{dt} = (C_R + C_G + C_{blank})\frac{k_{grow}}{\lambda}. \tag{9}$$

The color along the assembly is proportional to the concentration of each fluorescently labeled species (it is assumed that the concentrations of each labeled species are low enough to avoid competition for binding sites in the assembly):

$$R(L(t)) = C_R(t), \text{ and}$$
$$G(L(t)) = C_G(t). \tag{10}$$

This model was integrated with step-function changes in dye concentrations, considering the case where the change in concentration occurred either before or after assembly nucleation (FIG. 7A-7E). These results are in good qualitative agreement with the observed assembly fluorescence profiles.

Calculation 2—Effect of iPAK4 assemblies on cell membrane surface area and cell volume: Next, it was estimated how much an iPAK4 changes the membrane area of a HEK cell or a neuron. Measurements of membrane capacitance in HEK cells typically give ~10 pF, and the measurements in cultured neurons gave ~60 pF (FIG. 5C(ii)). At a specific capacitance of 1 μF/cm$^2$, these capacitance values correspond to surface areas of 1,000 μm$^2$ and 6,000 μm$^2$, respectively. The membrane forms a sheath around the assemblies, so at a typical assembly radius of 1 μm, the additional membrane area is approximately 6.3 μm$^2$ per μm of assembly extension beyond the size of the cell. For an assembly that protrudes by 20 μm, the additional surface area is ~130 μm$^2$. This is a modest perturbation on the starting surface area for HEK cells and is negligible for neurons.

The volume increases can similarly be estimated (though the additional volume is largely occupied by assembly). The volume of a HEK cell is ~5,000 μm$^3$, and for a cultured neuron the volume is somewhat larger. A 1 μm-radius assembly poking out of a cell will introduce additional volume of 3.1 μm$^3$ per micron of length, so for an assembly that protrudes by 20 μm, the additional volume is ~62 μm$^3$. This is an insignificant increase on the baseline. The axons and dendrites of neurons typically contain vastly larger surface areas and volumes than any assemblies poking from the cells.

Figure 24:
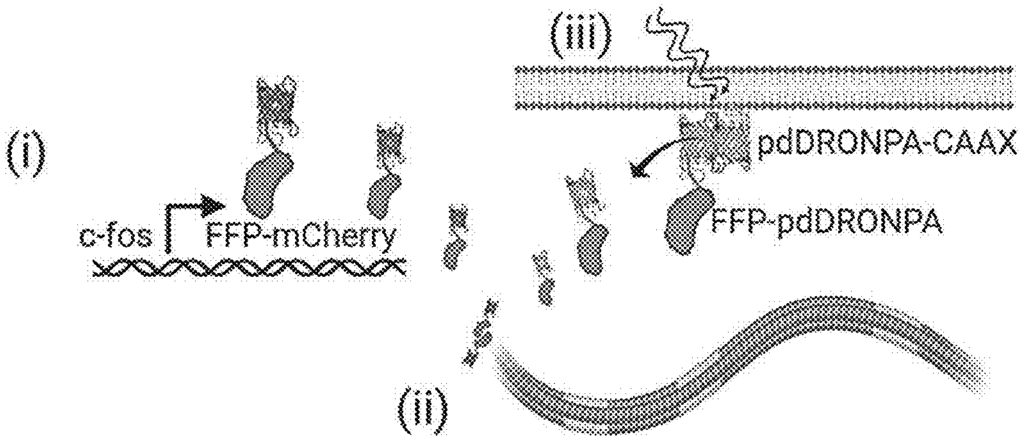
FIG. 24 shows optogenetic writing of fiducial time stamps. This design comprises three components. (i) A filament-forming protein (FFP) is fused to a payload. In the example shown, a fluorescently tagged FFP is expressed under control of an activity-dependent promoter to provide markers of neural activity. (ii) The protein assembles into filaments at a concentration-dependent rate. (iii) An FFP tagged with green-fluorescent photo dissociable dimeric DRONPA (pdDRONPA) is sequestered via binding to the cell membrane. Blue illumination releases the FFP-pdDRONPA, creating a green segment of the filament to mark the time of illumination.

Example 2: Optogenetic Strategies for Fiducial Time-Stamps in Protein Ticker-Tapes An alternative approach to the HALOTAG® strategy for measuring time described in Example 1 is to create an optogenetic system for fiducial time stamps (FIG. 24). An activity-independent promoter (e.g., hSyn) drives expression of a filament-forming protein (FFP) fused to photodissociable dimeric DRONPA (pdDRONPA)[51], and of membrane-bound pdDRONPA-CAAX. This arrangement sequesters the green-fluorescent FFP-pdDRONPA on the cell membrane. Flashes of blue light dissociate the pdDRONPA, enabling it to incorporate into the growing filament, leading to green fiducial timestamps. The pdDRONPA system is one of several possible approaches to optogenetic caging of the timestamp FFPs, comprising variants with different light sensitivities, activation spectra, affinities, and kinetics.[52,53]

This optogenetic approach has the advantage of not requiring exogenous dyes. The pdDRONPA system has a time resolution of ~20 seconds, implying that this system could achieve sub-minute time resolution. Brain-wide light delivery for pdDRONPA dissociation is a well understood problem. In a rodent brain, the whole cortex can be optically addressed via surface illumination,[54] and deeper brain regions can be reached with simple tapered multimode assemblies.[55]

Example 3: Alternative Payloads for Protein Ticker-Tapes

An advantage of the ticker-tape approach is that it can, in principle, accommodate different types of markers by swapping the reporter attached to the FFP. This modular design will facilitate recording of diverse modalities.

Multiple Promoters: Distinct promoters may be used to drive expression of FFPs fused to different-colored fluorescent proteins or epitope tags. Multicolor imaging may then be used to read the history of activity for multiple genes. For instance, recent work suggested that activity of c-fos and npas4 distinguishes ensembles of neurons that play different roles in memory encoding in the hippocampus.[56] Recording the simultaneous histories of both genes could help reveal the distinct roles of these two IEGs.

Figure 25A:
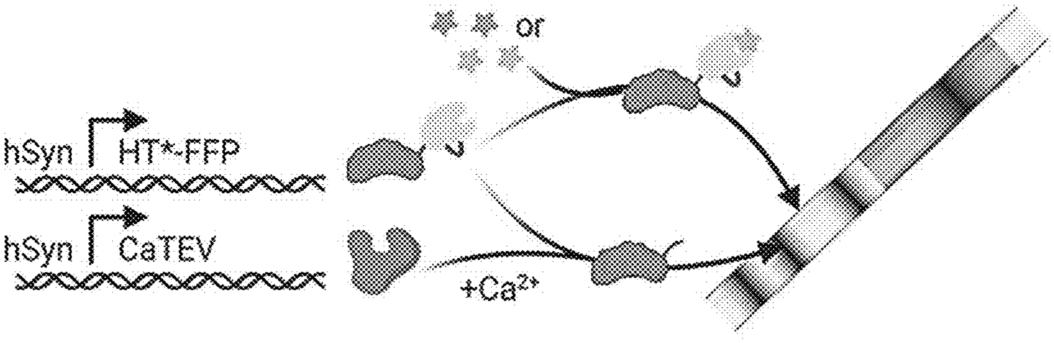
FIGS. 25A-25B show protein ticker tapes for $Ca^{2+}$ and kinase recording.

$Ca^{2+}$ recording: Active neurons have elevated time-average $Ca^{2+}$ concentration, so this modality is particularly compelling to measure via ticker tapes. A recognition site for the TEV protease can be inserted into position 143 in the HALOTAG® receptor, a site recently shown to modulate receptor activity (FIG. 25A).[57] This modified HALOTAG® receptor fused to a FFP (denoted HT*-FFP) and an engineered $Ca^{2+}$-dependent TEV protease (CaTEV) can be co-expressed.[58-60] Activation of the protease will cleave the HT, rendering it nonfunctional and dark. In this way, epochs of elevated $Ca^{2+}$, will appear as dark bands in the filament, and, as above, timestamps will be marked by changes in HT dye color. The pores in the Pak4 protein crystals are too small to admit the CaTEV, so labeled monomers already incorporated into the filament will be protected from proteolysis during later epochs of $Ca^{2+}$ elevation.

Figure 25B:
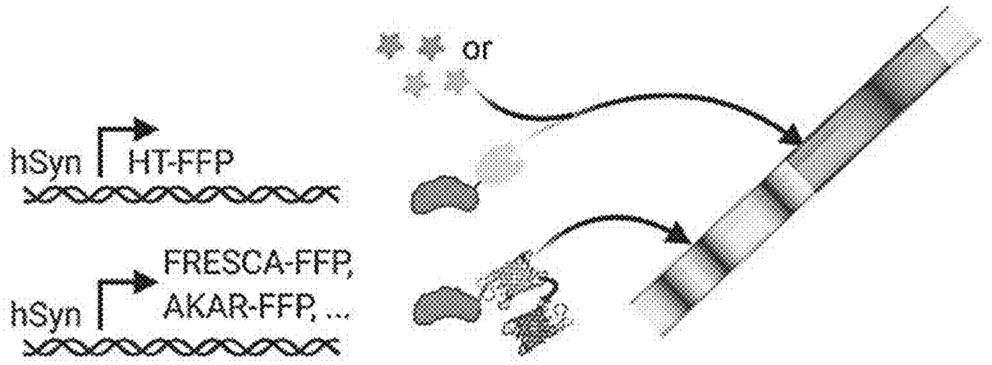

Kinase recording: Kinases mediate diverse signaling pathways in cells and are critical in memory formation because they mediate the effects of many neuromodulators. In fluorescent sensors of kinase activity, phosphorylation affects either the fluorescence of a circularly permuted fluorescent protein, or a fluorescence resonance energy transfer (FRET) signal. HT-FFP and different (kinase sensor)-FFP constructs can be co expressed, both under constitutive promoters (FIG. 25B). The reporter fluorescence signal along the filament will reflect the phosphorylated fraction of the sensors at the time of FFP incorporation. Once inside the assemblies, the sensors will be protected from phosphatases or kinases, so the state of the sensor will be preserved.

There are many possible fluorescent sensors.[61] Examples include: FRESCA (indirectly senses $Ca^2$, via CaMKII), ExRai-AKAR2 (indirectly senses cAMP via protein kinase A; not a FRET sensor but functionally similar), and EKARet (senses ERK activation).

Recording other signaling pathways: There are dozens of other fluorescent sensors that report post-translational covalent modifications.[62] For example, FFPs can be fused with sensors of, e.g., ubiquitination, sumoylation, nitrosylation, or glycosylation to record the dynamics of these important signaling modalities. Provided that the sensors are protected from the reverse process within the protein assembly, these records could be long lasting.

Protein expression: Hollow-assembly FFPs (e.g., iPAK4) may provide a means to record the expression histories of one or more proteins. CRISPR technology can be used to insert short SpyTag peptides into candidate protein-coding sequences. The complementary SpyCatcher protein can be fused to iPAK4. When SpyCatcher_protein encounters SpyTag peptide in solution, they form a covalent bond. In this way, the SpyTagged protein will be linked to the iPAK4 and incorporated into the scaffold. Subsequent immunostaining with antibodies to the target protein will reveal its pattern along the protein filament. Expansion microscopy can be used to open up the iPAK4 scaffold enough to allow antibodies to access the internal epitopes. This approach can be multiplexed by putting the SpyTag_peptide on multiple proteins and then using sequential rounds of antibody staining to map each protein's time-course.

REFERENCES

1. Renier, N. et al. Mapping of Brain Activity by Automated Volume Analysis of Immediate Early Genes. *Cell* 165, 1789-1802 (2016).

2. Vetere, G. et al. Chemogenetic Interrogation of a Brain-wide Fear Memory Network in Mice. *Neuron* 94, 363-374.e4 (2017).
3. DeNardo, L. A. et al. Temporal evolution of cortical ensembles promoting remote memory retrieval. *Nat. Neurosci.* 22, 460-469 (2019).
4. Mahringer, D. et al. Expression of c-Fos and Arc in hippocampal region CA1 marks neurons that exhibit learning-related activity changes. *bioRxiv* 644526 (2019) doi:10.1101/644526.
5. Zamft, B. M. et al. Measuring Cation Dependent DNA Polymerase Fidelity Landscapes by Deep Sequencing. *PloS One* 7, e43876 (2012).
6. Glaser, J. I. et al. Statistical Analysis of Molecular Signal Recording. *PLOS Comput. Biol.* 9, e1003145 (2013).
7. Rodriques, S. G. et al. RNA timestamps identify the age of single molecules in RNA sequencing. *Nat. Biotechnol.* 39, 320-325 (2021).
8. Pond, F. R., Gibson, I., Lalucat, J. & Quackenbush, R. L. R-body-producing bacteria. *Microbiol. Mol. Biol. Rev.* 53, 25-67 (1989).
9. Pélissier, H. C., Peters, W. S., Collier, R., Bel, A. J. E. van & Knoblauch, M. GFP Tagging of Sieve Element Occlusion (SEO) Proteins Results in Green Fluorescent Forisomes. *Plant Cell Physiol.* 49, 1699-1710 (2008).
10. LeVine, H. [18] Quantification of j-sheet amyloid fibril structures with thioflavin T. in *Methods in Enzymology* vol. 309 274-284 (Academic Press, 1999).
11. Barmada, S. J. & Harris, D. A. Visualization of Prion Infection in Transgenic Mice Expressing Green Fluorescent Protein-Tagged Prion Protein. *J. Neurosci.* 25, 5824-5832 (2005).
12. Shukla, S. et al. Molecular farming of fluorescent virus-based nanoparticles for optical imaging in plants, human cells and mouse models. *Biomater. Sci.* 2, 784-797 (2014).
13. Tsutsui, H. et al. A Diffraction-Quality Protein Crystal Processed as an Autophagic Cargo. *Mol. Cell* 58, 186-193 (2015).
14. Shen, H. et al. De novo design of self-assembling helical protein filaments. *Science* 362, 705-709 (2018).
15. Nguyen, T. K. et al. In-Cell Engineering of Protein Crystals with Nanoporous Structures for Promoting Cascade Reactions. *ACS Appl. Nano Mater.* 4, 1672-1681 (2021).
16. Baskaran, Y. et al. An in cellulo-derived structure of PAK4 in complex with its inhibitor Inka1. *Nat. Commun.* 6, 8681 (2015).
17. Abdelfattah, A. S. et al. Bright and photostable chemigenetic indicators for extended in vivo voltage imaging. *Science* 365, 699 (2019).
18. Grimm, J. B. et al. A general method to fine-tune fluorophores for live-cell and in vivo imaging. *Nat. Methods* 14, 987-994 (2017).
19. Grimm, J. B. et al. A general method to optimize and functionalize red-shifted rhodamine dyes. *Nat. Methods* 17, 815-821 (2020).
20. Grimm, J. B. et al. A general method to improve fluorophores for live-cell and single-molecule microscopy. *Nat. Methods* 12, 244-250 (2015).
21. DeNardo, L. & Luo, L. Genetic strategies to access activated neurons. *Curr. Opin. Neurobiol.* 45, 121-129 (2017).
22. Wu, Q. et al. The Temporal Pattern of cfos Activation in Hypothalamic, Cortical, and Brainstem Nuclei in Response to Fasting and Refeeding in Male Mice. *Endocrinology* 155, 840-853 (2014).
23. Sherin, J. E., Shiromani, P. J., McCarley, R. W. & Saper, C. B. Activation of Ventrolateral Preoptic Neurons During Sleep. *Science* 271, 216-219 (1996).
24. Gammie, S. C. & Nelson, R. J. cFOS and pCREB activation and maternal aggression in mice. *Brain Res.* 898, 232-241 (2001).
25. Haller, J., Tóth, M., Halasz, J. & De Boer, S. F. Patterns of violent aggression-induced brain c-fos expression in male mice selected for aggressiveness. Physiol. Behav. 88, 173-182 (2006).
26. Josselyn, S. A. & Tonegawa, S. Memory engrams: Recalling the past and imagining the future. Science 367, (2020).
27. Linghu, C. et al. Recording of cellular physiological histories along optically readable self-assembling protein chains. 2021.10.13.464006 (2021) doi:10.1101/2021.10.13.464006.
28. Das, A. T., Tenenbaum, L. & Berkhout, B. Tet-On Systems For Doxycycline-inducible Gene Expression. *Curr. Gene Ther.* 16, 156-167 (2016).
29. Amemiya, T., Kambe, T., Fukumori, R. & Kubo, T. Role of protein kinase Co in phorbol ester-induced c-fos gene expression in neurons of normotensive and spontaneously hypertensive rat brains. *Brain Res.* 1040, 129-136 (2005).
30. Furth, P. A. et al. Temporal control of gene expression in transgenic mice by a tetracycline-responsive promoter. *Proc. Natl. Acad. Sci.* 91, 9302-9306 (1994).
31. Iwamoto, M., Björklund, T., Lundberg, C., Kirik, D. & Wandless, T. J. A general chemical method to regulate protein stability in the mammalian central nervous system. *Chem. Biol.* 17, 981-988 (2010).
32. Miyamae, Y., Chen, L.-C., Utsugi, Y., Farrants, H. & Wandless, T. J. A Method for Conditional Regulation of Protein Stability in Native or Near-Native Form. *Cell Chem. Biol.* 27, 1573-1581.e3 (2020).
33. Liu, Q. & Tucker, C. L. Engineering genetically-encoded tools for optogenetic control of protein activity. *Curr. Opin. Chem. Biol.* 40, 17-23 (2017).
34. Hertel, F. & Zhang, J. Monitoring of post-translational modification dynamics with genetically encoded fluorescent reporters. *Biopolymers* 101, 180-187 (2014).
35. Specht, E. A., Braselmann, E. & Palmer, A. E. A Critical and Comparative Review of Fluorescent Tools for Live-Cell Imaging. *Annu. Rev. Physiol.* 79, 93-117 (2017).
36. Gibson, D. G. et al. Enzymatic assembly of DNA molecules up to several hundred kilobases. *Nat. Methods* 6, 343-345 (2009).
37. Thomas, P. & Smart, T. G. HEK293 cell line: A vehicle for the expression of recombinant proteins. *J. Pharmacol. Toxicol. Methods* 51, 187-200 (2005).
38. Geraerts, M., Michiels, M., Baekelandt, V., Debyser, Z. & Gijsbers, R. Upscaling of lentiviral vector production by tangential flow filtration. *J. Gene Med.* 7, 1299-1310 (2005).
39. Tomasello, G., Armenia, I. & Molla, G. The Protein Imager: a full-featured online molecular viewer interface with server-side HQ-rendering capabilities. *Bioinformatics* 36, 2909-2911 (2020).
40. Pond, F. R., Gibson, I., Lalucat, J. & Quackenbush, R. L. R-body-producing bacteria. *Microbiol. Mol. Biol. Rev.* 53, 25-67 (1989).
41. Pélissier, H. C., Peters, W. S., Collier, R., Bel, A. J. E. van & Knoblauch, M. GFP Tagging of Sieve Element Occlusion (SEO) Proteins Results in Green Fluorescent Forisomes. *Plant Cell Physiol.* 49, 1699-1710 (2008).

42. LeVine, H. [18] Quantification of j-sheet amyloid fibril structures with thioflavin T. in *Methods in Enzymology* vol. 309 274-284 (Academic Press, 1999).
43. Barmada, S. J. & Harris, D. A. Visualization of Prion Infection in Transgenic Mice Expressing Green Fluorescent Protein-Tagged Prion Protein. *J. Neurosci.* 25, 5824-5832 (2005).
44. Shukla, S. et al. Molecular farming of fluorescent virus-based nanoparticles for optical imaging in plants, human cells and mouse models. *Biomater. Sci.* 2, 784-797 (2014).
45. Tsutsui, H. et al. A Diffraction-Quality Protein Crystal Processed as an Autophagic Cargo. *Mol. Cell* 58, 186-193 (2015).
46. Shen, H. et al. De novo design of self-assembling helical protein filaments. *Science* 362, 705-709 (2018).
47. Nguyen, T. K. et al. In-Cell Engineering of Protein Crystals with Nanoporous Structures for Promoting Cascade Reactions. *ACS Appl. Nano Mater.* 4, 1672-1681 (2021).
48. Zakeri, B. et al. Peptide tag forming a rapid covalent bond to a protein, through engineering a bacterial adhesin. *Proc. Natl. Acad. Sci.* 109, E690-E697 (2012).
49. Sun, F., Zhang, W.-B., Mahdavi, A., Arnold, F. H. & Tirrell, D. A. Synthesis of bioactive protein hydrogels by genetically encoded SpyTag-SpyCatcher chemistry. *Proc. Natl. Acad. Sci.* 111, 11269-11274 (2014).
50. Iwamoto, M., Björklund, T., Lundberg, C., Kirik, D. & Wandless, T. J. A general chemical method to regulate protein stability in the mammalian central nervous system. *Chem. Biol.* 17, 981-988 (2010).
51. Zhou, X. X., Fan, L. Z., Li, P., Shen, K. & Lin, M. Z. Optical control of cell signaling by single-chain photoswitchable kinases. *Science* 355, 836-842 (2017).
52. Guglielmi, G., Falk, H. J. & De Renzis, S. Optogenetic Control of Protein Function: From Intracellular Processes to Tissue Morphogenesis. *Trends Cell Biol.* 26, 864-874 (2016).
53. Gil, A. A. et al. Optogenetic control of protein binding using light-switchable nanobodies. *Nat. Commun.* 11, 4044 (2020).
54. Li, N. et al. Spatiotemporal constraints on optogenetic inactivation in cortical circuits. *eLife* 8, e48622 (2019).
55. Pisanello, F. et al. Dynamic illumination of spatially restricted or large brain volumes via a single tapered optical assembly. *Nat. Neurosci.* 20, 1180-1188 (2017).
56. Sun, X. et al. Functionally Distinct Neuronal Ensembles within the Memory Engram. *Cell* 181, 410-423.e17 (2020).
57. Deo, C. et al. The HaloTag as a general scaffold for far-red tunable chemigenetic indicators. *Nat. Chem. Biol.* 1-6 (2021) doi:10.1038/s41589-021-00775-w.
58. O'Neill, B. K. & Laughlin, S. T. Neuronal Calcium Recording with an Engineered TEV Protease. *ACS Chem. Biol.* 13, 1159-1164 (2018).
59. Sanchez, M. I., Nguyen, Q.-A., Wang, W., Soltesz, I. & Ting, A. Y. Transcriptional readout of neuronal activity via an engineered Ca2+-activated protease. *Proc. Natl. Acad. Sci.* 117, 33186-33196 (2020).
60. Sanchez, M. I. & Ting, A. Y. Directed evolution improves the catalytic efficiency of TEV protease. *Nat. Methods* 17, 167-174 (2020).
61. Mehta, S. et al. Single-fluorophore biosensors for sensitive and multiplexed detection of signalling activities. *Nat. Cell Biol.* 20, 1215-1225 (2018).
62. Ting, A. Y., Kain, K. H., Klemke, R. L. & Tsien, R. Y. Genetically encoded fluorescent reporters of protein tyrosine kinase activities in living cells. *Proc. Natl. Acad. Sci.* 98, 15003-15008 (2001).
63. Ueda, H. R. et al. Whole-Brain Profiling of Cells and Circuits in Mammals by Tissue Clearing and Light-Sheet Microscopy. *Neuron* 106, 369-387 (2020).

INCORPORATION BY REFERENCE

The present application refers to various issued patent, published patent applications, scientific journal articles, and other publications, all of which are incorporated herein by reference. The details of one or more embodiments of the invention are set forth herein. Other features, objects, and advantages of the invention will be apparent from the Detailed Description, the Figures, the Examples, and the Claims.

EQUIVALENTS AND SCOPE

In the articles such as "a," "an," and "the" may mean one or more than one unless indicated to the contrary or otherwise evident from the context. Embodiments or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claims that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the disclosure or aspects of the disclosure consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control.

In addition, any particular embodiment of the present invention that falls within the prior art may be explicitly excluded from any one or more of the embodiments. Because such embodiments are deemed to be known to one of ordinary skill in the art, they may be excluded even if the exclusion is not set forth explicitly herein. Any particular embodiment of the invention can be excluded from any embodiment, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended embodiments. Those of ordinary skill in the art will appreciate that various changes and modifications to this description may be made without departing from the spirit or scope of the present invention, as defined in the following claims.

What is claimed is:

1. A method of profiling one or more cellular events in a cell over time, the method comprising:

incubating a cell for a period of time, wherein the cell comprises:

a first polynucleotide encoding a first protein assembly monomer under control of a first promoter; and a second polynucleotide encoding a second protein assembly monomer under control of a second promoter;

wherein a cellular event leads to expression of the first and/or second protein assembly monomer or a visualizable change or modification of the first and/or second protein assembly monomer in a protein assembly, and wherein activation of the second promoter is dependent on a cellular event being profiled.

2. The method of claim 1, wherein the cellular event comprises gene expression, protein expression, enzymatic activity, metabolic activity, a change in the concentration of an ion, a change in the concentration of a small molecule, the

SEQUENCE LISTING

```
Sequence total quantity: 3
SEQ ID NO: 1           moltype = AA  length = 366
FEATURE                Location/Qualifiers
source                 1..366
                       mol_type = protein
                       organism = synthetic construct
SEQUENCE: 1
MDYKDDDDKS GSEAEDWTAA LLNRGRSRQP LVLGDNCFAD LVHNWMELPE EFPAAPAVPG  60
PPGPRSPQRE PQRVSHEQFR AALQLVVDPG DPRSYLDNFI KIGEGSTGIV CIATVRSSGK  120
LVAVKKMDLR KQQRRELLFN EVVIMRDYQH ENVVEMYNSY LVGDELWVVM EFLEGGALTD  180
IVTHTRMNEE QIAAVCLAVL QALSVLHAQG VIHRDIKSDS ILLTHDGRVK LSDFGFCAQV  240
SKEVPRRKSL VGTPYWMAPE LISRLPYGPE VDIWSLGIMV IEMVDGEPPY FNEPPLKAMK  300
MIRDNLPPRL KNLHKVSPSL KGFLDRLLVR DPAQRATAAE LLKHPFLAKA GPPASIVPLM  360
RQNRTR                                                             366

SEQ ID NO: 2           moltype = AA  length = 656
FEATURE                Location/Qualifiers
source                 1..656
                       mol_type = protein
                       organism = synthetic construct
SEQUENCE: 2
MIGTGFPFDP HYVEVLGERM HYVDVGPRDG TPVLFLHGNP TSSYVWRNII PHVAPTHRCI  60
APDLIGMGKS DKPDLGYFFD DHVRFMDAFI EALGLEEVVL VIHDWGSALG FHWAKRNPER  120
VKGIAFMEFI RPIPTWDEWP EFARETFQAF RTTDVGRKLI IDQNVFIEGT LPMGVVRPLT  180
EVEMDHYREP FLNPVDREPL WRFPNELPIA GEPANIVALV EEYMDWLHQS PVPKLLFWGT  240
PGVLIPPAEA ARLAKSLPNC KAVDIGPGLN LLQEDNPDLI GSEIARWLST LEISGEPTTS  300
GSEAEDWTAA LLNRGRSRQP LVLGDNCFAD LVHNWMELPE EFPAAPAVPG PPGPRSPQRE  360
PQRVSHEQFR AALQLVVDPG DPRSYLDNFI KIGEGSTGIV CIATVRSSGK LVAVKKMDLR  420
KQQRRELLFN EVVIMRDYQH ENVVEMYNSY LVGDELWVVM EFLEGGALTD IVTHTRMNEE  480
QIAAVCLAVL QALSVLHAQG VIHRDIKSDS ILLTHDGRVK LSDFGFCAQV SKEVPRRKSL  540
VGTPYWMAPE LISRLPYGPE VDIWSLGIMV IEMVDGEPPY FNEPPLKAMK MIRDNLPPRL  600
KNLHKVSPSL KGFLDRLLVR DPAQRATAAE LLKHPFLAKA GPPASIVPLM RQNRTR      656

SEQ ID NO: 3           moltype = AA  length = 596
FEATURE                Location/Qualifiers
source                 1..596
                       mol_type = protein
                       organism = synthetic construct
SEQUENCE: 3
MSKGEELFTG VVPILVELDG DVNGYKFSVS GEGEGDATYG KLTLKFICTT GKLPVPWPTL  60
VTTLTYGVQC FSRYPDHMKR HDFFKSAMPE GYVQERTIFF KDDGNYKTRA EVKFEGDTLV  120
NRIELKGIDF KEDGNILGHK LEYNYNSHNV YIMADKQKNG IKANFKTRHN IEDGGVQLAD  180
HYQQNTPIGD DPVLLPDNHY LSTQSALSKD PNEKRDHMVI LEFVTAAGIT HGMDELYKSG  240
GSEAEDWTAA LLNRGRSRQP LVLGDNCFAD LVHNWMELPE EFPAAPAVPG PPGPRSPQRE  300
PQRVSHEQFR AALQLVVDPG DPRSYLDNFI KIGEGSTGIV CIATVRSSGK LVAVKKMDLR  360
KQQRRELLFN EVVIMRDYQH ENVVEMYNSY LVGDELWVVM EFLEGGALTD IVTHTRMNEE  420
QIAAVCLAVL QALSVLHAQG VIHRDIKSDS ILLTHDGRVK LSDFGFCAQV SKEVPRRKSL  480
VGTPYWMAPE LISRLPYGPE VDIWSLGIMV IEMVDGEPPY FNEPPLKAMK MIRDNLPPRL  540
KNLHKVSPSL KGFLDRLLVR DPAQRATAAE LLKHPFLAKA GPPASIVPLM RQNRTR      596
```

presence of a metabolite, exposure to light, cell differentiation, cell growth, or cell division.

3. The method of claim 1, wherein the protein assembly monomers comprise proteins that spontaneously assemble in cells to form a protein assembly.

4. The method of claim 1, wherein the protein assembly monomers are monomers capable of forming polymers selected from the group consisting of endogenous microtubules, bacterial R-bodies, plant forisomes, amyloid fibrils, prions, filamentous viruses, crystals of the fluorescent protein XpA, crystals of the kinase PAK4, engineered fiber-forming or lattice-forming peptides, and polymers of SpyTag and SpyCatcher.

5. The method of claim 4, wherein the protein assembly monomers comprise the catalytic domain of PAK4 fused to the PAK4 inhibitor Inka1 (iPAK4).

6. The method of claim 1, wherein the first promoter is an activity-independent constitutive promoter.

7. The method of claim 1, wherein an inducer of the cellular event or a molecule produced as a result of the cellular event activates the second promoter.

8. The method of claim 1, wherein the cellular event is profiled in multiple cells simultaneously.

9. The method of claim 1, wherein the visualizable change or modification of the first and/or second protein monomer in a protein assembly comprises binding of a dye to the first and/or second protein monomer or post-translational modification of the first and/or second protein monomer.

10. The method of claim 1, wherein the first protein assembly monomer is fused to a visualizable tag.

11. The method of claim 10, wherein the visualizable tag comprises a peptide tag that binds fluorescent dyes or a protein tag that binds fluorescent dyes.

12. The method of claim 10, wherein the cell is incubated for a period of time $t_1$ in the presence of a first fluorescent dye that binds to the visualizable tag.

13. The method of claim 12 further comprising incubating the cell for a period of time $t_2$ in the presence of a second fluorescent dye that binds to the visualizable tag.

14. The method of claim 13, wherein the fluorescent dye used in each period of time produces a colored band in the protein assembly.

15. The method of claim 14, wherein the length of each colored band correlates linearly with time.

16. The method of claim 14, wherein the length of each colored band correlates linearly with wall-clock time.

17. The method of claim 14, wherein the time of a cellular event can be interpolated from the relative location of a visualizable protein fused to the second protein assembly monomer between the start and the end of a colored band.

18. The method of claim 13 further comprising a step of imaging the protein assembly in the cell to determine the location of the second protein assembly monomer fused to a visualizable protein relative to the locations of the first and the second fluorescent dyes bound to the visualizable tag, thereby determining the times at which the cellular event occurs.

19. The method of claim 12 further comprising incubating the cell for one or more additional periods of time in the presence of a fluorescent dye, wherein the same fluorescent dye is not used in adjacent periods of time.

20. The method of claim 10, wherein the visualizable tag comprises a light-gated tag.

21. The method of claim 10, wherein the visualizable tag is susceptible to cleavage by a protease.

22. The method of claim 10, wherein the second protein assembly monomer is fused to a visualizable protein, and wherein the visualizable protein is visualizable only after being modified due to a cellular event.

23. The method of claim 22, wherein the cellular event comprises a post-translational modification.

24. The method of claim 1, wherein the second protein assembly monomer is fused to a visualizable protein.

25. The method of claim 24, wherein the cell comprises one or more additional polynucleotides encoding a protein assembly monomer fused to a distinct visualizable protein under control of a distinct promoter, wherein activation of the distinct promoter is associated with an occurrence of a different cellular event, thereby profiling multiple cellular events simultaneously.

26. The method of claim 1, wherein the second protein assembly monomer is fused to a binding moiety, wherein the binding moiety binds a molecule associated with an occurrence of the cellular event being profiled.

27. A method for profiling a cellular event over time comprising:

a) incubating a cell, wherein the cell comprises:
   - a first polynucleotide encoding a protein assembly monomer fused to a visualizable tag under control of a first promoter; and
   - a second polynucleotide encoding a protein assembly monomer fused to a visualizable protein under control of a second promoter, wherein activation of the second promoter is associated with an occurrence of the cellular event being profiled;

for a period of time $t_1$ in the presence of a first fluorescent dye that binds to the visualizable tag, thereby allowing the protein assembly monomers expressed by the first and second polynucleotides to assemble into a protein assembly;

b) further incubating the cell for a period of time $t_2$ in the presence of a second fluorescent dye that binds to the visualizable tag, thereby allowing the protein assembly monomers expressed by the first and second polynucleotides to further assemble onto the protein assembly; and c) imaging the protein assembly in the cell to determine the location of the protein assembly monomer fused to the visualizable protein relative to the locations of the first and the second fluorescent dyes bound to the visualizable tag, thereby determining the times at which the cellular event occurs.

* * * * *